United States Patent
Ferritto Crespo et al.

(10) Patent No.: US 7,220,880 B2
(45) Date of Patent: May 22, 2007

(54) AMIDE LINKER PEROXISOME PROLIFERATOR ACTIVATED RECEPTOR MODULATORS

(75) Inventors: Rafael Ferritto Crespo, Madrid (ES); Jose Alfredo Martin, Madrid (ES); Maria Dolores Martin-Ortega Finger, Madrid (ES); Isabel Rojo Garcia, Madrid (ES); Quanrong Shen, Fishers, IN (US); Alan M Warshawsky, Carmel, IN (US); Yanping Xu, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 140 days.

(21) Appl. No.: 10/517,581

(22) PCT Filed: Jun. 11, 2003

(86) PCT No.: PCT/US03/16207

§ 371 (c)(1),
(2), (4) Date: Dec. 8, 2004

(87) PCT Pub. No.: WO04/000789

PCT Pub. Date: Dec. 31, 2003

(65) Prior Publication Data

US 2006/0111406 A1 May 25, 2006

Related U.S. Application Data

(60) Provisional application No. 60/390,102, filed on Jun. 19, 2002.

(51) Int. Cl.
C07C 229/28 (2006.01)
A61K 31/195 (2006.01)

(52) U.S. Cl. ............ 562/452; 562/426; 562/441; 562/442

(58) Field of Classification Search .......... 562/441, 562/444, 452, 442, 426; 514/563
See application file for complete search history.

(56) References Cited

U.S. PATENT DOCUMENTS

| 4,999,378 A | 3/1991 | Fujii et al. |
| 5,122,539 A | 6/1992 | Abraham et al. |
| 5,378,716 A | 1/1995 | Hamanaka et al. |

FOREIGN PATENT DOCUMENTS

| EP | 0 558 062 A2 | 2/1993 |
| JP | 2001-261612 * | 9/2001 |
| WO | WO 92/10468 | 6/1992 |
| WO | WO 96/38428 | 12/1996 |
| WO | WO 97/28115 | 8/1997 |
| WO | WO 99/11606 | 3/1999 |
| WO | WO 00 63196 A | 10/2000 |
| WO | WO 01/16120 A1 | 3/2001 |
| WO | WO 01/40207 A1 | 6/2001 |
| WO | WO 02/14291 A1 | 2/2002 |
| WO | WO 02/38553 A2 | 5/2002 |
| WO | WO 02/096893 A1 | 12/2002 |
| WO | WO 03/048130 A2 | 6/2003 |
| WO | WO 03 051821 A | 6/2003 |
| WO | WO 03 051822 A | 6/2003 |
| WO | WO 03/066581 A1 | 8/2003 |

OTHER PUBLICATIONS

Beilstein Registry. No. 5961279 [abstract].
Large, M.S, et al. 1983. 1-[(Substituted-amido)phenoxy]-3-[[(substituted-amido)alkyl]amino]propan-2-ols. J. Med. Chem. 26(3):352-357.
Beilstein Registry. No. 3406655; Journal; Nametkin et al.; ZH. Obshch. Khim., 21, 1951, 2146-47.
Beilstein Registry. No. 8569754 [abstract].
Penning, T.H. et al. 2000. Structure-Activity Relationship Studies on I-[2-(4-Phenylphenoxy)ethyl]pyrrolidine (SC-22716), a Potent Inhibitor of Leukotriene $A_4$ ($LTA_4$) Hydrolase. J. Med. Chem. 43(4):721-35.
Beilstein Registry. No. 5989230 [abstract ].
Barrie, S.E. et al. 1984. A Reappraisal of the Effect upon Thymidine Kinase of Thymidine Derivatives Carrying Large Groups at the 5'-Position. J. Med. Chem. 27(8): 1044-47.
Beilstein Registry. No. 8227222 [abstract].
Adamczyk, M. et al. 1999. Use of Lipase for Regioselective One Pot Amidation and Hydrolysis. Bioorg. Med. Chem. Lett. 9(2): 245-48.
Chem. Abst. No. 135:257231, Kadota, H. et al., *Preparation of catechol propionic acid derivatives as peroxisome proliferator-activated receptor (PPAR) .alpha. and .gamma. agonists*, application of JP 2001261612, Sep. 26, 2001.
Wilson TM, et al. 2000. The PPARs: From Orphan Receptors to Drug Discovery. Journal of Medical Chemistry 43(4): 527-550.
Etgen, GJ, et al. 2003. PPAR Ligands for Metabolic Disorders. Current Topics in Medicinal Chemistry 3(14): 1649-1661.

* cited by examiner

*Primary Examiner*—Shailendra Kumar
(74) *Attorney, Agent, or Firm*—MaCharri Vorndran-Jones

(57) ABSTRACT

The present invention is directed to compounds, compositions, and use of compounds the structural Formula (I)

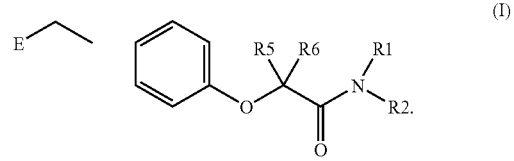

(I)

26 Claims, No Drawings

AMIDE LINKER PEROXISOME PROLIFERATOR ACTIVATED RECEPTOR MODULATORS

This Application claims the benefit of U.S. Provisional Application Ser. No. 60/390,102, filed Jun. 19, 2002, and PCT Application Ser. No. PCT/US03/16207, filed Jun. 11, 2003.

BACKGROUND OF THE INVENTION

Peroxisome Proliferator Activated Receptors (PPARs) are members of the nuclear hormone receptor super family, which are ligand-activated transcription factors regulating gene expression. Various subtypes of PPARs have been discovered. These include, for example, PPARα, NUC1, PPARγ and PPARδ.

PPARα, PPARγ and PPARδ receptors have been implicated in diabetes mellitus, cardiovascular disease, obesity, Syndrome X and gastrointestinal disease, such as, inflammatory bowel disease. Syndrome X is the combination of symptoms which include hyperinsulemia combined with hypertension, elevated body weight, elevated triglycerides and elevated LDL.

Current PPAR agonist treatment for Syndrome X relates to the use of thiazolidinediones (TZDs) or other insulin sensitivity enhancers (ISEs). TZDs are a class of PPAR gamma agonists that have been shown to increase the sensitivity of insulin sensitive cells. Increasing insulin sensitivity rather than the amount of insulin in the blood reduces the likelihood of hypoglycemic coma. However, TZDs and ISEs have been associated undesirable clinical effects and improved clinical profiles are desired. Therefore, a need exists for new pharmaceutical agents having a desirable pharmacological profile. Such PPAR selective or dual selective agonist compounds are especially desirable when associated with a desirable safety profile and the desired effect in the treatment of diabetes and/or related clinical conditions.

SUMMARY OF THE INVENTION

An embodiment of the present invention is directed toward compounds represented by the structural formula I:

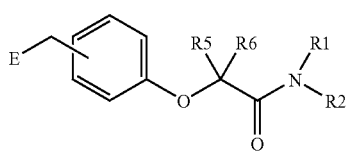

Formula I (a) R1 is selected from the group consisting of hydrogen, $C_1$-$C_8$ alkyl, $C_3$-$C_6$ cycloalkyl, aryl-$C_{0-4}$-alkyl, heteroaryl-$C_{0-4}$-alkyl, amino$C_1$-$C_4$alkyl, $C_3$-$C_6$ cycloalkylaryl-$C_{0-2}$-alkyl, arylhetero$C_1$-$C_8$alkyl, —CHC(O)$C_1$-$C_4$ alkoxy, $C_{0-4}$-alkyl-C(O)hetero$C_1$-$C_8$alkyl, and —CH$_2$—C(O)—R15-R16; and which $C_1$-$C_8$ alkyl, $C_3$-$C_6$ cycloalkyl, aryl-$C_{0-4}$-alkyl, heteroaryl-$C_{0-4}$-alkyl, amino$C_1$-$C_4$alkyl, $C_3$-$C_6$ cycloalkylaryl-$C_{0-2}$-alkyl, arylhetero$C_1$-$C_8$alkyl, —CHC(O)$C_1$-$C_4$ alkoxy, $C_{0-4}$-alkyl-C(O)hetero$C_1$-$C_8$alkyl and —CH$_2$—C(O)—R15-R16 are each independently unsubstituted or substituted with from one to three substituents each independently selected from the group consisting of R1'; and wherein R15 is O or NH and R16 is $C_1$-$C_2$ alkyl or benzyl, which $C_1$-$C_2$ alkyl or benzyl are each unsubstituted or substituted with from one to three substituents each independently selected from the group consisting of R16';

(b) R1' and R2' are each independently a group consisting of $C_1$-$C_5$ alkyl, $C_3$-$C_6$ cycloalkyl, $C_1$-$C_5$ alkoxy, aryl$C_0$-$C_2$alkoxy, halo$C_1$-$C_3$alkyl, halo, aryl, —C(O)$C_1$-$C_5$alkyl, —C(O)-aryl, halo$C_1$-$C_5$alkyloxy, aryl$C_1$-$C_5$alkyl, and biaryl$C_1$-$C_5$alkyl; and which —C(O)-aryl is unsubstituted or substituted with from one to three substituents each independently selected from the group consisting of halo, $C_1$-$C_5$ alkyl, halo$C_1$-$C_5$ alkyl, $C_1$-$C_5$ alkoxy, and —C(O)$C_1$-$C_5$alkyl; and which $C_1$-$C_5$ alkyl, aryl$C_1$-$C_5$alkyl, biaryl$C_1$-$C_5$alkyl, and aryl" are each independently unsubstituted or substituted with from one to three substituents each independently selected from the group consisting of halo, $C_1$-$C_8$alkyl, aryl, halo$C_1$-$C_5$ alkyl, trihalo$C_1$-$C_3$alkyl, $C_1$-$C_5$alkoxy, and aryl$C_1$-$C_5$alkyl; and which aryl is unsubstituted or substituted with from one to three substituents each independently selected from the group consisting of halo, $C_1$-$C_8$alkyl, aryl, halo$C_1$-$C_5$alkyl, trihalo$C_1$-$C_3$alkyl, $C_1$-$C_5$alkoxy, and aryl$C_1$-$C_5$alkyl;

(c) R2 is selected from the group consisting of $C_1$-$C_8$ alkyl, $C_3$-$C_6$ cycloalkyl, aryl-$C_{0-4}$-alkyl, heteroaryl-$C_{0-4}$-alkyl, heto$C_1$-$C_6$ cycloalkylaryl, heto$C_1$-$C_6$cycloalkylaryl$C_1$-$C_4$alkyl, aminono$C_1$-$C_4$alkyl, $C_3$-$C_6$ cycloalkylaryl-$C_{0-2}$-alkyl, arylhetero$C_1$-$C_8$alkyl, $C_{0-4}$-alkyl-C(O)hetero$C_1$-$C_8$alkyl, —CH(C(O)OCH$_3$)benzyl, and —CH$_2$—C(O)—R15"-R16", and which $C_1$-$C_8$ alkyl, $C_3$-$C_6$ cycloalkyl, aryl-$C_{0-4}$-alkyl, heto$C_1$-$C_6$cycloalkylaryl, heto$C_1$-$C_6$cycloalkylaryl$C_1$-$C_4$alkyl, heteroaryl-$C_{0-4}$-alkyl, amino$C_1$-$C_4$alkyl, $C_3$-$C_6$ cycloalkylaryl-$C_{0-2}$-alkyl, arylhetero$C_1$-$C_8$alkyl, $C_{0-4}$-alkyl-C(O)hetero$C_1$-$C_8$alkyl, and —CH$_2$—C(O)—R15"-R16" are each independently unsubstituted or substituted with from one to three substituents each independently selected from the group consisting of R2';

(d) R15" is O or NH;

(e) R16" is $C_1$-$C_2$ alkyl or benzyl which $C_1$-$C_2$ alkyl and benzyl are each unsubstituted or substituted with from one to three substituents each independently selected from the group consisting of R16';

(f) R1 and R2 together may form a heterocyclic ring which heterocyclic ring is unsubstituted or substituted with from one to three substituents each independently selected from the group consisting of R1' and which heterocyclic ring is optionally fused with an aryl;

(g) E is selected from the group consisting of C(R3)(R4) A, (CH$_2$)$_n$ COOR13, aryl-$C_{0-4}$-alkyl, thio-$C_1$-$C_4$-alkyl, thioaryl, aryl$C_1$-$C_4$alkoxy, $C_1$-$C_4$alkoxy $C_1$-$C_4$alkyl, aminoaryl, and amino $C_1$-$C_4$alkyl; and which (CH$_2$)$_n$ COOR13, aryl-$C_{0-4}$-alkyl, thio-$C_1$-$C_4$-alkyl, thioaryl, $C_1$-$C_4$alkoxyaryl, $C_1$-$C_4$alkoxy$C_1$-$C_4$alkyl, aminoaryl, and amino$C_{1-4}$alkyl are each independently unsubstituted or substituted with from one to three substituents each independently selected from the group consisting of E';

(h) R7' and R7" are each independently selected from the group consisting of $C_1$-$C_4$ alkyl and $C_1$-$C_4$ haloalkyl;

(i) n and m are each independently selected from the group consisting of 0, 1, 2 and 3;

(j) A is selected from the group consisting of (CH$_2$)$_m$ COOR14, $C_1$-$C_3$alkylnitrile, carboxamide, sulfonamide, acylsulfonamide and tetrazole, and which sulfonamide, acylsulfonamide and tetrazole are each independently unsubstituted or substituted with from one to three substituents each independently selected from the group consisting of A';

(k) A' is a group consisting of $C_1$-$C_4$alkyl, $C_1$-$C_4$ haloalkyl, heteroaryl, and aryl, and wherein heteroaryl and aryl are each independently unsubstituted or substituted with from one to three substituents each independently selected from the group consisting of halo, $C_1$-$C_5$ alkyl, $C_1$-$C_5$ haloalkyl, $C_1$-$C_5$ alkoxy, and —C(O)$C_1$-$C_5$ alkyl;

(l) R3 is selected from the group consisting of H, $C_1$-$C_5$ alkyl, $C_1$-$C_5$ alkenyl, and $C_1$-$C_6$ alkoxy;

(m) R4 is selected from the group consisting of H, halo, $C_1$-$C_5$ alkyl, $C_1$-$C_6$ alkoxy, $C_3$-$C_6$ cycloalkyl, aryl $C_0$-$C_4$ alkyl, and $C_{0-4}$alkoxyaryl, and which $C_1$-$C_5$ alkyl, $C_1$-$C_5$ alkoxy, $C_3$-$C_6$ cycloalkyl, aryl $C_0$-$C_4$ alkyl, and $C_{0-4}$alkoxyaryl are each independently unsubstituted or each independently substituted with from one to four substituents each independently selected from R4'; or R3 and R4 are combined to form a $C_3$-$C_6$ cycloalkyl;

(n) R5 and R6 are each independently selected from the group consisting of hydrogen, $C_1$-$C_8$ alkyl, aryl-$C_{0-4}$-alkyl, heteroaryl-$C_{0-4}$-alkyl, $C_3$-$C_6$ cycloalkylaryl-$C_{0-2}$-alkyl, $C_3$-$C_6$ cycloalkyl-$C_{0-2}$-alkyl, and —CH$_2$—C(O)—R17-R18, and which $C_1$-$C_8$ alkyl, aryl-$C_{0-4}$-alkyl, heteroaryl-$C_{0-4}$-alkyl, $C_3$-$C_6$ cycloalkylaryl-$C_{0-2}$-alkyl, $C_3$-$C_6$ cycloalkyl-$C_{0-2}$-alkyl; and —CH$_2$—C(O)—R17-R18 are each independently unsubstituted or substituted with from one to four substituents each independently selected from the group consisting of R5';

(o) E', R4', R5', and R13" are each independently a group consisting of C1-C5 alkyl, C1-C5 alkoxy, C1-C5 haloalkyl, C1-C5 haloalkoxy, nitro, cyano, CHO, hydroxy, $C_1$-$C_4$ alkanoic acid, phenyl, aryloxy, SO$_2$R7', SR7", aryl$C_0$-$C_2$alkoxy, C1-C6alkylcarboxamido, and COOH;

(p) R16' is a group consisting of halo, $C_1$-$C_8$alkyl, aryl, haloalkyl, trihalo$C_1$-$C_3$alkyl, $C_1$-$C_5$alkoxy, and aryl$C_1$-$C_5$alkyl;

(q) R17 and R18 are each independently selected from $C_1$-$C_8$ alkyl, aryl-$C_{0-4}$-alkyl, heteroaryl-$C_{0-4}$-alkyl, $C_3$-$C_6$ cycloalkylaryl-$C_{0-2}$-alkyl, and $C_3$-$C_6$ cycloalkyl-$C_{0-2}$-alkyl;

(r) R13 and R14 are each independently selected from the group consisting of hydrogen, C1-C4alkyl, aryl, and arylmethyl, and which C1-C4alkyl are each independently unsubstituted or independently substituted with from one to three substituents each independently selected from the group of R13' and which arylmethyl and aryl are each independently unsubstituted or independently substituted with from one to three substituents each independently selected from the group consisting of R14';

(s) R13' is a group consisting of $C_1$-$C_5$ alkyl, $C_3$-$C_6$ cycloalkyl, $C_1$-$C_5$ haloalkyl, $C_1$-$C_5$ alkoxy, aryloxy, halo, aryl, —C(O)$C_1$-$C_5$alkyl, —C(O)-aryl, halo$C_1$-$C_5$alkyloxy, aryl $C_1$-$C_5$ alkyl, and $C_1$-$C_5$ alkylbiaryl, and which —C(O) aryl, aryl, aryl $C_1$-$C_5$ alkyl, and $C_1$-$C_5$ alkylbiaryl are each independently unsubstituted or subtutited with from one to three substituents each independently selected from the group consisting of R13"; and (t) R14' is a group consisting of halo, C1-C8alkyl, $C_1$-$C_5$ haloalkyl, $C_1$-$C_5$ alkoxy, and aryl$C_0$-$C_4$alkyl; or (u) a pharmaceutically acceptable salt thereof.

An embodiment of the present invention is directed toward compounds represented by the following structural formula:

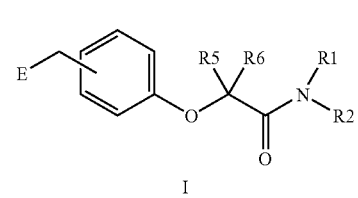

Formula I'

I (a) R1 is selected from the group consisting of hydrogen, $C_1$-$C_8$ alkyl, $C_3$-$C_6$ cycloalkyl, aryl-$C_{0-4}$-alkyl, heteroaryl-$C_{0-4}$-alkyl, amino$C_1$-$C_4$alkyl, $C_3$-$C_6$ cycloalkylaryl-$C_{0-2}$-alkyl, arylhetero$C_1$-$C_8$alkyl, —CHC(O)$C_1$-$C_4$ alkoxy; $C_{0-4}$-alkyl-C(O)hetero$C_1$-$C_8$alkyl, and —CH$_2$—C(O)—R15-R16; wherein said $C_1$-$C_8$ alkyl, $C_3$-$C_6$cycloalkyl, aryl-$C_{0-4}$-alkyl, heteroaryl-$C_{0-4}$-alkyl, amino$C_1$-$C_4$alkyl, $C_3$-$C_6$ cycloalkylaryl-$C_{0-2}$-alkyl, arylhetero$C_1$-$C_8$alkyl, —CHC(O) $C_1$-$C_4$ alkoxy, $C_{0-4}$-alkyl-C(O)hetero$C_1$-$C_8$alkyl, and —CH$_2$—C(O)—R15-R16 are each independently optionally substituted with from one to three substituents each independently selected from the group consisting of R1'; wherein R15 is O or NH and R16 is benzyl optionally substituted with from one to three substituents each independently selected from the group consisting of R16';

(b) R2 is selected from the group consisting of $C_1$-$C_8$ alkyl, $C_3$-$C_6$ cycloalkyl, aryl-$C_{0-4}$-alkyl, heteroaryl-$C_{0-4}$-alkyl, amino$C_1$-$C_4$alkyl, $C_3$-$C_6$ cycloalkylaryl-$C_{0-2}$-alkyl, arylhetero$C_1$-$C_8$alkyl, $C_{0-4}$-alkyl-C(O)hetero$C_1$-$C_8$alkyl, and —CH$_2$—C(O)—R$^{15}$-R$^{16}$; wherein said $C_1$-$C_8$ alkyl, $C_3$-$C_6$ cycloalkyl, aryl-$C_{0-4}$-alkyl, heteroaryl-$C_{0-4}$-alkyl, amino$C_1$-$C_4$alkyl, $C_3$-$C_6$ cycloalkylaryl-$C_{0-2}$-alkyl, arylhetero$C_1$-$C_8$alkyl, $C_{0-4}$-alkyl-C(O)hetero$C_1$-$C_8$alkyl, and —CH$^2$—C(O)—R$^{15}$-R$^{16}$ are each independently optionally substituted with from one to three substituents each independently selected from the group consisting of R2'; wherein R$^{15}$ is O or NH and R$^{16}$ is benzyl optionally substituted with from one to three substituents each independently selected from the group consisting of R16";

(c) R1 and R2 together may form a substituted or unsubstituted heterocyclic ring;

(d) E is selected from the group consisting of C(R3)(R4) A, and a substituted or unsubstituted selected from the group consisting of (CH$_2$)$_n$ COOR13, aryl-$C_{0-4}$-alkyl, thio-$C_{1-4}$-alkyl, thioaryl, $C_{1-4}$alkoxyaryl, $C_{1-4}$alkoxy$C_{1-4}$alkyl, aminoaryl, and amino$C_{1-4}$alkyl;

(e) n and m are each independently selected from the group consisting of 0, 1, 2 and 3;

(f) A is an functional group selected from the group consisting of (CH$_2$)$_m$ COOR14, $C_1$-$C_3$alkylnitrile, carboxamide, substituted or unsubstituted sulfonamide, substituted or unsubstituted acylsulfonamide and substituted or unsubstituted tetrazole;

(g) R3 is H, saturated or unsaturated $C_1$-$C_5$ alkyl, $C_1$-$C_5$ alkoxy;

(h) R4 is H, halo, a substituted or unsubstituted group selected from $C_1$-$C_5$ $_{alkyl,}$ $_{C1}$-$C_5$ alkoxy, $C_3$-$C_6$ cycloalkyl, aryl $C_0$-$C_4$ alkyl, $C_{1-4}$alkoxyaryl, and phenyl, or R3 and R4 are combined to form a $C_3$-$C_6$ cycloalkyl;

(i) R5 and R6 are each independently selected from the group consisting of hydrogen, substituted or unsubstituted group selected from $C_1$-$C_8$ alkyl, aryl-$C_{0-4}$-alkyl, heteroaryl-$C_{0-4}$-alkyl, $C_3$-$C_6$ cycloalkylaryl-$C_{0-2}$-alkyl, $C_3$-$C_6$ cycloalkyl-$C_{0-2}$-alkyl, and —CH$_2$—C(O)—R17-R18;

(j) R17 and R18 are each independently selected from $C_1$-$C_8$ alkyl, aryl-$C_{0-4}$-alkyl, heteroaryl-$C_{0-4}$-alkyl, $C_3$-$C_6$ cycloalkylaryl-$C_{0-2}$-alkyl, and $C_3$-$C_6$ cycloalkyl-$C_{0-2}$-alkyl;

(k) R13 and R14 are each independently selected from the group consisting of hydrogen, optionally substituted C1-C4alkyl and optionally substituted arylmethyl; and pharmaceutically acceptable salts thereof.

Another embodiment of the present invention is a compound of Formula II:

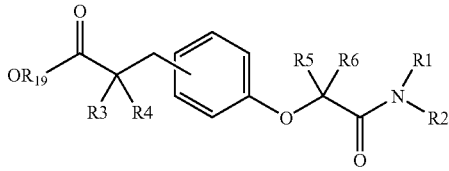

II wherein R19 is selected from the group consisting of hydrogen, C1-C4alkyl, aryl, and arylmethyl, wherein the alkyl, aryl and arylmethyl is unsubstituted or substituted with from one to three substituents each independently selected from R14';

and pharmaceutically acceptable salts thereof, wherein R1, R2, R3, R4, R5, and R6 are as as defined above in Formula I.

Another embodiment of the present invention is a compound of Formula III:

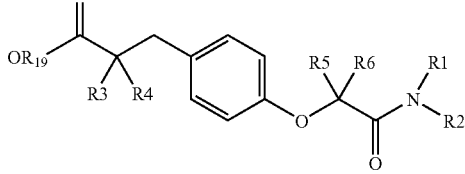

III wherein R19 is selected from the group consisting of hydrogen, wherein R19 is selected from the group consisting of hydrogen, C1-C4alkyl, aryl, and arylmethyl, wherein the alkyl, aryl and arylmethyl is unsubstituted or substituted with from one to three substituents each independently selected from R14'.;

and pharmaceutically acceptable salts thereof, wherein R1, R2, R3, R4, R5, and R6 are as defined above in Formula I.

Another embodiment of this invention is a compound and pharmaceutically acceptable salts of Structural Formula:

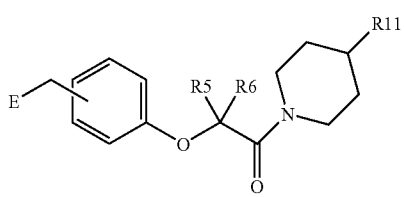

wherein R11 is selected from the group consisting of aryl, aryloxy, —C(O)aryl, halo$C_1$-$C_5$alkyloxy, $C_1$-$C_5$ alkylaryl, $C_1$-$C_5$ alkylbiaryl, and C1-C6 alkyl, wherein the aryl, —C(O)aryl, halo$C_1$-$C_5$alkyloxy, $C_1$-$C_5$ alkylaryl, $C_1$-$C_5$ alkylbiaryl, and C1-C6 alkyl are each independently unsubstituted or each independently substituted with from one to three substituents each independently selected from the group consisting of R1'.

Another preferred embodiment is a compound and pharmaceutically acceptable salts of Structural Formula:

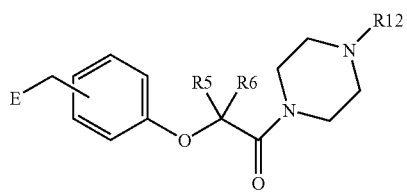

wherein R12 is selected from the group consisting of aryl, aryloxy, —C(O)aryl, halo$C_1$-$C_5$alkyloxy, aryl$C_1$-$C_5$ alkyl, $C_1$-$C_5$ alkylbiaryl, and C1-C6 alkyl, wherein the aryl, —C(O)aryl, aryloxy, halo$C_1$-$C_5$alkyloxy, $C_1$-$C_5$ alkylaryl, $C_1$-$C_5$ alkylbiaryl, and C1-C6 alkyl are each independently unsubstituted or each independently substituted with from one to three substituents each independently selected from the group consisting of R1'.

Another embodiment is a compound of the formula:

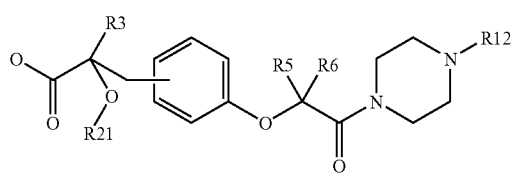

In another feature of this invention, a compound claimed herein is radiolabeled.

In one embodiment, the present invention also relates to pharmaceutical compositions which comprising at least one compound of the present invention, or a pharmaceutically acceptable salt thereof, and a pharmaceutically acceptable carrier.

In another embodiment, the present invention relates to a method of modulating a PPAR alpha receptor by contacting the receptor with at least one compound represented by Structural Formula I, and/or pharmaceutically acceptable salts thereof.

In another embodiment, the present invention relates to a method of modulating a PPAR gamma receptor by contacting the receptor with at least one compound represented by Structural Formula I, and/or pharmaceutically acceptable salts thereof.

In another embodiment, the present invention relates to a method of modulating a PPAR delta receptor by contacting the receptor with at least one compound represented by Structural Formula I, and/or a pharmaceutically acceptable salt thereof.

In another embodiment, the present invention relates to a method of modulating a PPAR alpha receptor and a PPAR gamma receptor by contacting the receptor with at least one compound represented by Structural Formula I, and/or pharmaceutically acceptable salts thereof.

In another embodiment, the present invention relates to a method of modulating a PPAR gamma and a PPAR delta receptor by contacting the receptor with at least one compound represented by Structural Formula I, and/or a pharmaceutically acceptable salt there of.

The compounds of the present invention can be effective in treating and, in patients susceptible thereto, preventing, Syndrome X, Type II diabetes, hyperglycemia, hyperlipidemia, obesity, coagaulopathy, hypertension, atherosclerosis, and other disorders related to Syndrome X and cardiovascular diseases. In addition, the compounds are expected to be associated with more favorable clinical safety and efficacy profile than compounds currently used to treat these conditions. Further, compounds of this invention can be useful for lowering fibrinogen, increasing HDL levels, treating renal disease, controlling desirable weight, treating demyelinating diseases, treating certain viral infections, and treating liver disease.

DETAILED DESCRIPTION OF THE INVENTION

The terms used to describe the instant invention have the following meanings herein.

As used herein, "alkyl" groups include straight chained and/or branched hydrocarbons, which are completely saturated. Thus, such alkyl may be selected from primary, secondary, tertiary and the like. The term "$C_0$-$C_{n'}$ alkyl" means an alkyl group having the stated number of carbon atoms. A preferable $C_0$-$C_{n'}$ alkyl is methyl, ethyl, propyl, or butyl in one preferred embodiment of the present invention. Another preferred C1-C4 alkyl is methyl or ethyl.

As used herein, the term "aminoC1-C4alkyl" means that the amino group is linked to the base molecule through an alkyl having the stated number of carbon atoms.

The term "—C(O)alkyl" means that the alkyl, having the stated number of carbon atoms, is linked to the base molecule through a "—C(O)—" linker. Likewise, —C(O)C1-C5alkyl means an alkyl having from one to five carbon atoms linked to the base molecule via a —C(O) linker.

As used herein, "alkylene" is an unsaturated $C_1$-$C_5$ straight or branched chain hydrocarbon group having at least one double bond.

"Cycloalkyl" groups, and "$C_3$-$C_6$ cycloalkyl" as used herein, include cyclic hydrocarbons having the stated number of carbon atoms in the ring, which are partially or completely saturated. It can be preferred that the cycloalkyl groups are completely saturated. It may be preferred that cyclo alkyl is a ring having $C_3$-$C_7$ alkyl in the ring. Such cycloalkyl includes, but is not limited to cyclpropyl, cyclopentyl, cyclohexyl, and the like.

As used herein, "aryl" groups include carbocyclic aromatic ring systems (e.g. phenyl), fused polycyclic aromatic ring systems (e.g. naphthyl and anthracenyl) and aromatic ring systems fused to carbocyclic non-aromatic ring systems (e.g., 1,2,3,4-tetrahydronaphthyl and benzodioxyl). A preferred aryl group can be phenyl. Another preferred aryl can be naphthyl. As used herein, "arylalkyl" means that the aryl group is linked to the point of attachment through an alkyl linker having the stated number of carbon atoms. It may be preferred that the alkyl is C0-C3 or C1-C3 alkyl. The term "aryl-$C_0$alkyl" means that the aryl group is directly linked at the point of attachment through a bond. As used herein, the term "alkylaryl" and "C1-C5 alkylaryl" also mean that the aryl is linked to the point of attachment though an alkyl linker having the stated number of carbon atoms and said alkyl linker is straight chain or branched. Additionally, said linker and/or aryl can be substituted when said substituent is "substituted". It can be preferred that the alkyl linker is from one to three carbon atoms. A preferred aryl may be a C6-C10 aryl. The term "arylmethyl" means an arylalkyl that is aryl$C_1$alkyl.

As used herein the term "aryl substituent" has the same meaning as "aryl" as defined herein above. The term "—C(O)aryl substituent" means that the aryl group is linked to the base molecule through a —C(O)— linker. Further, as used herein, the term "—C(O)aryl" has the same meaning as "—C(O)aryl substituent".

As used herein, the term "aryloxy" means that an aryl group is linked to the base molecule through an oxygen. The term "aryl$C_0$-$C_2$ alkoxy" means that the arylalkyl is linked to the base molecule through an oxygen. When aryl$C_0$-$C_2$alkoxy is aryl$C_0$alkoxy, then the term means "aryloxy". That is, the alkyl is absent when the term is aryl $C_0$alkoxy.

As used herein, the term "C1-C5alkylbiaryl" means an alkyl having the stated number of carbon atoms is linked to the base molecule and on the terminal end of said alkyl, is substituted with two independent aryl groups. In one preferred embodiment, it is preferred that each of the aryl of the biaryl is phenyl.

The term "cycloalkyaryl" means that a cycloalkyl group is fused with an aryl group to form a bicyclic substituent. Cycloalkylarylalkyl means that the fused bicyclic cycloalkylaryl is linked to the base molecule through an alkyl linker. That is "C3-C6 cycloalkylaryl-C0-C2alkyl" means a cycloalkyl having from 3 to 6 carbon atoms is fused with an aryl and then linked to the base molecule through an alkyl having from zero to 2 carbon atoms. When there are zero carbon atoms, then the aryl is linked directly to the base molecule.

The term "halo" means Cl, F, Br, and I. A preferred halo can be Cl. Another preferred halo can be F. As used herein the term "C1-C4 haloalkyl" and "halo C1-C4alkyl" means the alkyl, having the state number of carbon atoms may be substituted with one or more halogens. For example, but not limited to, $CF_3$, $C_2F_5$, $C_2F_3$, $C_3F_7$, and the like. Likewise, the term "haloC1-C5alkyloxy" means an alkyl oxy having the stated number of carbon atoms substituted with one or more halogens. The haloalkyoxy is linked to the base molecule via the oxygen.

As used herein, "heteroaryl" groups include carbocyclic aromatic ring systems wherein at least one carbon of the aryl group is replaced by at least one independently selected heteroatom, such as nitrogen, oxygen or sulfur (e.g. pyridinyl and the like), fused polycyclic aromatic ring systems having at least one heteroatom replacing a carbon from the ring and aromatic ring systems fused to carbocyclic non-aromatic ring systems having at least one heteroatom replacing a carbon atom from the ring. A preferred heteroaryl may be C5-C10 heteroaryl. A preferred heteroaryl group can be thiophenyl, pyridinyl, piperidinyl, pyrazinyl, and the like. Another preferred heteroaryl group can be oxazole, thiazole, and the like. Another preferred heteroaryl group can be thienyl, thiazole, benzothiazole, thiadiazole, and the like.

As used herein, the term "heteroaryl-$C_0$-$C_n$alkyl" means that the heteroaryl is linked to the base molecule through an alkyl having the stated number of carbon atoms. As used herein, the term "heteroaryl $C_0$alkyl" means that the heteroaryl is linked directed to the base molecule.

As used herein, the term, "$C_{0-4}$-alkyl-C(O)heteroC$_1$-C$_8$alkyl" means that the heteroC$_1$-C$_8$alkyl group, wherein one of the carbon atoms of the alkyl group is replaced with a heteroatom selected from the group consisting of S, O and N, is linked to the base nucleus through a $C_{0-4}$-alkylC(O) group. Embodiments include, but are not limited to when the heteroalkyl is methoxy, ethoxy, propoxy, thiomethyl, thioethyl, thiopropyl, aminomethyl, aminoethyl, aminopropyl, and the like.

As used herein the term "C1-C5alkoxy" or "C1-Cn' alkoxy" means that the alkyl having the stated number of carbon atoms is linked to the base molecule through an oxygen.

As used herein the term "—CHC(O)C1-C4alkoxy" means that the alkoxy having the stated number of carbon atoms is linked to the base molecule through a —CH—C(O)-linker. Likewise, the term "—CH$_2$C(O)R15-R16" means that the R16 is linked to the base molecule through a "—CH$_2$C(O)R15" linker.

As used herein, the term, "arylheteroC$_1$-C$_8$alkyl" means that the aryl group is attached to the base nucleus through a C$_1$-C$_8$alkyl group in which one of the carbon atoms of the alkyl group is replaced with a heteroatom selected from the group consisting of S, O, and N (herein "heteroalkyl linker"). One embodiment is when the heteroatom is an S and the aryl is a phenyl which is unsubstituted or substituted with from one to three substituents each independently selected from the group consisting of PHENYLSUB. Another embodiment is when the heteroatom is an O and the aryl is a phenyl which is unsubstituted or substituted with from one to three substituents each independently selected from the group consisting of PHENYLSUB. Another embodiment is an arylheteroalkyl wherein aryl is unsubstituted or substituted with from one to three substituents each independently selected from PHENYLSUB and the heteroalkyl linker is unsubstituted or substituted with from one to three substituents each independently selected from R1' or R2'. Another embodiment is when the heteroatom is a N and the aryl is a phenyl which is unsubstituted or substituted with from one to three substituents each independently selected from the group consisting of PHENYLSUB. Said embodiments are in no way intended to limit the scope of the claimed invention, and are provided to further illustrate a selection of embodiments claimed herein. As used herein "PHENYLSUB" is a group consisting of halo, C1-C8alkyl, aryl, haloC$_1$-C$_3$alkyl, trihaloC1-C3alkyl, C$_1$-C$_3$ alkoxy, —C(O)C$_1$-C$_4$alkyl, and arylC$_1$-C$_3$alkyl.

"Heterocyclic group", or "heterocyclic ring", as used herein, is a C$_3$-C$_{12}$ ring system having the stated number of carbon atoms wherein from one to three carbon atoms are replaced by a heteroatom such as nitrogen, sulfur or oxygen. Heterocyclic groups include benzofuranyl, benzothiazolyl, benzothienyl, isoquinolyl, isoxazolyl, morpholino, oxadiazolyl, pyridyl, pyrimidinyl, pyrrolyl, quinolyl, tetrahydropyranyl and thienyl. It may be preferred that the heterocyclic ring is a three to six membered the ring. Perferred heterocyclic rings may be

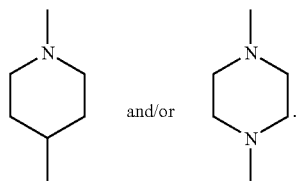

and/or

The term "heterocycloalkylaryl" means that a heterocyclic group, as defined herein above, is fused to an aryl group to form the substituent. Such groups include, but are in no way limited to:

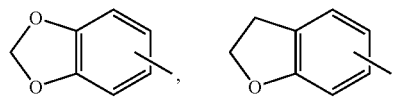

and the like. The term heterocycloaklylarylakyl means that the heterocycloalkylaryl is linked to the base molecule via an alkyl having the stated number of carbon atoms. Thus, hetoC$_1$-C$_6$cycloalkylarylC1-C4alkyl is a C1-C6 heterocyclic ring fused with an aryl and linked to the base molecule via a C1-C4 alkyl linker. A preferred aryl can be phenyl.

The term "thioaryl" means that the aryl ring has at least one carbon atom replaced by a sulfur atom. Such thioaryl groups include, but are not limited to thiophenyl, and the like.

The term "alkoxyaryl" mans that the aryl group is attached to the base molecule through an alkoxy linker. The term "alkoxyalkyl" means that the alkyl chain has one carbon replaced by an oxygen atom. The term "aminoaryl" means that the aryl group is linked to the base molecule through an amino group. The term "aminoalkyl" means that the alkyl chain is attached to the base molecule through an amino group. The term "alkylnitrile" means that the nitrile group is attached to the base molecule through an alkyl linker.

The compounds of Structural Formula I may contain one or more chiral centers, and exist in different optically active forms. When compounds of Structural Formula I contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound represented by Structural Formula I has more than one chiral substituent it may exist in diastereoisomeric forms. The diastereoisomeric pairs may be separated by methods known to those skilled in the art, for example chromatography or crystallization and the individual enantiomers within each pair may be separated as described above. The present invention includes each diastereoisomer of compounds of Structural Formula I and mixtures thereof.

Certain compounds of Structural Formula I may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Structural Formula I and mixtures thereof.

Certain compounds of Structural Formula I may exist in zwitterionic form and the present invention includes each zwitterionic form of compounds of Structural Formula I and mixtures thereof.

"Pharmaceutically-acceptable salt" refers to salts of the compounds of the Structural Formula I that are substantially non-toxic to mammals. Typical, pharmaceutically-acceptable salts include those salts prepared by reaction of the compounds of the present invention with a mineral or organic acid or an organic or inorganic base. Such salts are known as base addition salts, respectively. It should be recognized that the particular counterion forming a part of any salt of this invention is not of a critical nature, so long as the salt as a whole is pharmaceutically-acceptable and as long as the counterion does not contribute undesired qualities to the salt as a whole.

By virtue of its acidic moiety, a compound of Structural Formula I forms salts with pharmaceutically acceptable bases. Some examples of base addition salts include metal salts such as aluminum; alkali metal salts such as lithium, sodium or potassium; and alkaline earth metal salts such as calcium and magnesium; and ammonium or substituted ammonium salts. Examples of substituted ammonium salts include, for instance, those with lower alkylamines such as trimethylamine, triethylamine; hydroxyalkylamines such as 2-hydroxyethylamine, bis-(2-hydroxyethyl)-amine or tri-(2-hydroxyethyl)-amine, cycloalkylamines such as bicyclohexylamine or dibenzylpiperidine, N-benzyl-β-phenethylamine, dehydroabietylamine, N,N'-bisdehydroabietylamine, glucamine, N-methylglucamine; bases of the pyridine type such as pyridine, collidine, quinine or quinoline; and salts of basic amino acids such as lysine and arginine.

These salts may be prepared by methods known to those skilled in the art.

In addition, it is generally not desirable to formulate pharmaceuticals containing substantial amounts of organic solvent (e.g., ethyl acetate) due to potential solvent toxicity to the recipient thereof and changes in potency of the pharmaceutical as a function of the solvent.

The term, "active ingredient" means the compounds generically described by Structural Formula I as well as the salts of such compounds.

The term "pharmaceutically acceptable" means that the carrier, diluent, excipients and salt must be compatible with the other ingredients of the composition. Pharmaceutical compositions of the present invention are prepared by procedures known in the art using well-known and readily available ingredients.

"Preventing" refers to reducing the likelihood that the recipient will incur or develop any of the pathological conditions described herein. It is preferred that the recipient is thought to be susceptible to said condition. A preferred recipient may be a human.

"Treating" refers to mediating a disease or condition and preventing, or mitigating, its further progression or ameliorate the symptoms associated with the disease or condition.

"Pharmaceutically-effective amount" means that amount of a compound, or of its salt thereof, that will elicit the biological or medical response of a tissue, system, or, mammal. Such an amount can be administered prophylactically to a patient thought to be susceptible to development of a disease or condition. Such amount when administered prophylactically to a patient can also be effective to prevent or lessen the severity of the mediated condition. Such an amount is intended to include an amount which is sufficient to modulate a PPAR alpha receptor or to prevent or mediate a disease or condition. Conditions prevented or treated by PPARα receptors include diabetes mellitus, cardiovascular disease, Syndrome X, obesity and gastrointestinal disease.

A "mammal" is an individual animal that is a member of the taxonomic class Mammalia. The class Mammalia includes humans, monkeys, chimpanzees, gorillas, cattle, swine, horses, sheep, dogs, cats, mice, and rats.

Administration to a human is most preferred. The compounds and compositions of the present invention are useful for the treatment and/or prophylaxis of cardiovascular disease, for raising serum HDL cholesterol levels, for lowering serum triglyceride levels and for lower serum LDL cholesterol levels. Elevated triglyceride and LDL levels, and low HDL levels, are risk factors for the development of heart disease, stroke, and circulatory system disorders and diseases.

The compounds and compositions of the present invention are also useful for treating and/or preventing obesity.

Further, these compounds and compositions are useful for the treatment and/or prophylaxis of non-insulin dependent diabetes mellitus (NIDDM) with reduced or no body weight gains by the patients. Furthermore, the compounds and compositions of the present invention are useful to treat or prevent acute or transient disorders in insulin sensitivity, such as sometimes occur following surgery, trauma, myocardial infarction, and the like. The physician of ordinary skill will know how to identify humans who will benefit from administration of the compounds and compositions of the present invention.

The present invention further provides a method for the treatment and/or prophylaxis of hyperglycemia in a human or non-human mammal which comprises administering an effective, non-toxic amount of a compound of the general formula (I), or a tautomeric form thereof and/or a pharmaceutically acceptable salt thereof to a hyperglycemic human or non-human mammal in need thereof.

They are useful as therapeutic substances in preventing or treating Syndrome X, diabetes mellitus and related endocrine and cardiovascular disorders and diseases in human or non-human animals.

The invention also relates to the use of a compound of Formula I as described above, for the manufacture of a medicament for treating a PPARα mediated condition.

A therapeutically effective amount of a compound of Structural Formula I can be used for the preparation of a medicament useful for treating Syndrome X, diabetes, treating obesity, lowering tryglyceride levels, lowering serum LDL levels, raising the plasma level of high density lipoprotein, and for treating, preventing or reducing the risk of developing atherosclerosis, and for preventing or reducing the risk of having a first or subsequent atherosclerotic disease event in mammals, particularly in humans. In general, a therapeutically effective amount of a compound of the present invention typically reduces serum triglyceride levels of a patient by about 20% or more, and increases serum HDL levels in a patient. Preferably, HDL levels will be increased by about 30% or more. In addition, a therapeutically effective amount of a compound, used to prevent or treat NIDDM, typically reduces serum glucose levels, or more specifically HbA1c, of a patient by about 0.7% or more.

Advantageously, compositions containing the compound of Structural Formula I or the salts thereof may be provided in dosage unit form, preferably each dosage unit containing from about 1 to about 500 mg be administered although it will, of course, readily be understood that the amount of the compound or compounds of Structural Formula I actually to be administered will be determined by a physician, in the light of all the relevant circumstances.

When used herein Syndrome X includes pre-diabetic insulin resistance syndrome and the resulting complications thereof, insulin resistance, non-insulin dependent diabetes, dyslipidemia, hyperglycemia obesity, coagulopathy, hypertension and other complications associated with diabetes. The methods and treatments mentioned herein include the above and encompass the treatment and/or prophylaxis of any one of or any combination of the following: pre-diabetic insulin resistance syndrome, the resulting complications thereof, insulin resistance, Type II or non-insulin dependent diabetes, dyslipidemia, hyperglycemia, obesity and the complications associated with diabetes including cardiovascular disease, especially atherosclerosis.

The compositions are formulated and administered in the same general manner as detailed herein. The compounds of the instant invention may be used effectively alone or in combination with one or more additional active agents depending on the desired target therapy. Combination therapy includes administration of a single pharmaceutical dosage composition which contains a compound of Structural Formula I and one or more additional active agents, as well as administration of a compound of Structural Formula I and each active agent in its own separate pharmaceutical dosage formulation. For example, a compound of Structural Formula I or thereof and an insulin secretogogue such as biguanides, thiazolidinediones, sulfonylureas, insulin, or α-glucosidose inhibitors can be administered to the patient together in a single oral dosage composition such as a tablet or capsule, or each agent administered in separate oral dosage formulations. Where separate dosage formulations are used, a compound of Structural Formula I and one or more additional active agents can be administered at essentially the same time, i.e., concurrently, or at separately staggered times, i.e., sequentially; combination therapy is understood to include all these regimens.

An example of combination treatment or prevention of atherosclerosis may be wherein a compound of Structural Formula I or salts thereof is administered in combination with one or more of the following active agents: antihyperlipidemic agents; plasma HDL-raising agents; antihypercholesterolemic agents, fibrates, vitamins, aspirin, and the like. As noted above, the compounds of Structural Formula I can be administered in combination with more than one additional active agent.

Another example of combination therapy can be seen in treating diabetes and related disorders wherein the compounds of Structural Formula I, salts thereof can be effectively used in combination with, for example, sulfonylureas, biguanides, thiazolidinediones, α-glucosidase inhibitors, other insulin secretogogues, insulin as well as the active agents discussed above for treating atherosclerosis.

The compounds of the present invention, and the pharmaceutically acceptable salt thereof, have valuable pharmacological properties and can be used in pharmaceutical compositions containing a therapeutically effective amount of a compound of the present invention, or pharmaceutically acceptable salts thereof, in combination with one or more pharmaceutically acceptable excipients. Excipients are inert substances such as, without limitation carriers, diluents, fillers, flavoring agents, sweeteners, lubricants, solubilizers, suspending agents, wetting agents, binders, disintegrating agents, encapsulating material and other conventional adjuvants. Proper formulation is dependent upon the route of administration chosen. Pharmaceutical compositions typically contain from about 1 to about 99 weight percent of the active ingredient which is a compound of the present invention.

Preferably, the pharmaceutical formulation is in unit dosage form. A "unit dosage form" is a physically discrete unit containing a unit dose, suitable for administration in human subjects or other mammals. For example, a unit dosage form can be a capsule or tablet, or a number of capsules or tablets. A "unit dose" is a predetermined quantity of the active compound of the present invention, calculated to produce the desired therapeutic effect, in association with one or more pharmaceutically-acceptable excipients. The quantity of active ingredient in a unit dose may be varied or adjusted from about 0.1 to about 1000 milligrams or more according to the particular treatment involved.

The dosage regimen utilizing the compounds of the present invention is selected by one of ordinary skill in the medical or veterinary arts, in view of a variety of factors, including, without limitation, the species, age, weight, sex, and medical condition of the recipient, the severity of the condition to be treated, the route of administration, the level of metabolic and excretory function of the recipient, the dosage form employed, the particular compound and salt thereof employed, and the like.

Preferably, the compounds of the present invention are administered in a single daily dose, or the total daily dose may be administered in divided doses, two, three, or more times per day. Where delivery is via transdermal forms, of course, administration is continuous.

Suitable routes of administration of pharmaceutical compositions of the present invention include, for example, oral, eyedrop, rectal, transmucosal, topical, or intestinal administration; parenteral delivery (bolus or infusion), including intramuscular, subcutaneous, intramedullary injections, as well as intrathecal, direct intraven-tricular, intravenous, intraperitoneal, intranasal, or intraocular injections. The compounds of the invention can also be administered in a targeted drug delivery system, such as, for example, in a liposome coated with endothelial cell-specific antibody.

For oral administration, the compounds can be formulated readily by combining the active compounds with pharmaceutically acceptable carriers well known in the art. Such carriers enable the compounds of the invention to be formulated as tablets, pills, powders, sachets, granules, dragees, capsules, liquids, elixers, tinctures, gels, emulsions, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores.

For oral administration in the form of a tablet or capsule, the active ingredient may be combined with an oral, non-toxic, pharmaceutically-acceptable carrier, such as, without limitation, lactose, starch, sucrose, glucose, methyl cellulose, calcium carbonate, calcium phosphate, calcium sulfate, sodium carbonate, mannitol, sorbitol, and the like; together with, optionally, disintegrating agents, such as, without limitation, cross-linked polyvinyl pyrrolidone; maize, starch, methyl cellulose, agar, bentonite, xanthan gum, alginic acid, or a salt thereof such as sodium alginate, and the like; and, optionally, binding agents, for example, without limitation, gelatin, acacia, natural sugars, beta-lactose, corn sweeteners, natural and synthetic gums, acacia, tragacanth, sodium alginate, carboxymethyl-cellulose, polyethylene glycol, waxes, and the like; and, optionally, lubricating agents, for example, without limitation, magnesium stearate, sodium stearate, stearic acid, sodium oleate, sodium benzoate, sodium acetate, sodium chloride, talc, and the like. When a dosage unit form is a capsule, it may contain, in addition to materials of the above type, a liquid carrier such as a fatty oil.

Solid form formulations include powders, tablets and capsules. A solid carrier can be one or more substance which may also act as flavoring agents, lubricants, solubilisers, suspending agents, binders, tablet disintegrating agents and encapsulating material.

In powders, the carrier is a finely divided solid which is in admixture with the finely divided active ingredient. In tablets, the active ingredient is mixed with a carrier having the necessary binding properties in suitable proportions and compacted in the shape and size desired.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Sterile liquid formulations include suspensions, emulsions, syrups, and elixirs. The active ingredient can be dissolved or suspended in a pharmaceutically acceptable carrier, such as sterile water, sterile organic solvent, or a mixture of both sterile water and sterile organic solvent.

The active ingredient can also be dissolved in a suitable organic solvent, for example, aqueous propylene glycol. Other compositions can be made by dispersing the finely divided active ingredient in aqueous starch or sodium carboxymethyl cellulose solution or in a suitable oil.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

All formulations for oral administration should be in dosages suitable for such administration. Particularly suitable compositions for oral administration are unit dosage forms such as tablets and capsules.

For parental administration the compounds of the present invention, or salts thereof, can be combined with sterile aqueous or organic media to form injectable solutions or suspensions. Formulations for injection may be presented in unit dosage form, such as in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that each syringability exists. It must be stable under the conditions of manufacture and storage and must be preserved against any contamination. The carrier can be solvent or dispersion medium containing, for example, water, preferably in physiologically compatible buffers such as Hanks's solution, Ringer's solution, or physiological saline buffer, ethanol, polyol (e.g. glycerol, propylene glycol and liquid polyethylene glycol), propylene glycol and liquid polyethylene glycol), suitable mixtures thereof, and vegetable oils. Under ordinary conditions of storage and use, these preparations contain a preservative to prevent the growth of microorganisms.

The injectable solutions prepared in this manner can then be administered intravenously, intraperitoneally, subcutaneously, or intramuscularly, with intramuscular administration being preferred in humans.

For transmucosal administration, penetrants appropriate to the barrier to be permeated are used in the formulation. Such penetrants are generally known in the art. The active compounds can also be administered intranasally as, for example, liquid drops or spray.

For buccal administration, the compositions may take the form of tablets or lozenges formulated in a conventional manner.

For administration by inhalation, the compounds for use according to the present invention are conveniently delivered in the form of a dry powder inhaler, or an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of gelatin for use in an inhaler or insufflator may be formulated containing a powder mix of the compound and a suitable powder base such as lactose or starch.

Pharmaceutical compositions of the present invention can be manufactured in a manner that is itself known, e.g., by means of conventional mixing, dissolving, granulating, dragee-making, levigating, emulsifying, encapsulating, entrapping or lyophilizing processes.

In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, lyophilized solid or paste, semi-solid, or liquid material which acts as a vehicle, or can be in the form of tablets, pills, powders, lozenges, elixirs, suspensions, emulsions, solutions, syrups, aerosols (as a solid or in a liquid medium), or ointment, containing, for example, up to 10% by weight of the active compound. The compounds of the present invention are preferably formulated prior to administration.

The following pharmaceutical formulations 1 and 2 are illustrative only and are not intended to limit the scope of the invention in any way. "Active Ingredient", refers to a compound according to Structural Formula I or salts thereof.

Formulation 1

Hard gelatin capsules are prepared using the following ingredients:

| | Quantity (mg/capsule) |
|---|---|
| Active Ingredient | 250 |
| Starch, dried | 200 |
| Magnesium stearate | 10 |
| Total | 460 mg |

Formulation 2

A tablet is prepared using the ingredients below:

| | Quantity (mg/tablet) |
|---|---|
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

In yet another embodiment of the compounds of the present invention, the compound is radiolabelled, such as with carbon-14, or tritiated. Said radiolabelled or tritiated compounds are useful as reference standards for in vitro assays to identify new PPARα and or PPARδ agonists.

Synthesis

Compounds of the present invention have been formed as specifically described in the examples. Further, many compounds were prepared as more generally as shown in the following schematic. Alternative synthesis methods may also be effective and are known to the skilled artisan.

Preparation 1

Preparation of (2S)-3-(4-Hydroxy-phenyl)-2-methoxy-propionic acid ethyl ester (2S)-3-(4-Hydroxy-phenyl)-2-methoxy-propionic acid ethyl ester: Sodium bis-(trimethyl-silyl)amide (440 ml, 0.44 mol, 1.0 M in THF) was cooled to −70° C. under a nitrogen atmosphere. A solution of 4-benzyloxybenzaldehyde (85 g, 0.4 mol) and methyl methoxyacetate (52 g, 0.5 mol) in THF (0.5 L) was added dropwise at −70° C. over 2 h, and the mixture was stirred for an hour. A solution of concentrated HCl (85 mL) and water (85 mL) was added at −70° C. The resulting solution was allowed to warm to ambient temperature and was extracted with MTBE (2×0.5 L). The combined extracts were washed with brine (0.5 L), dried (MgSO$_4$), filtered, and concentrated and dissolved in CH$_2$Cl$_2$ (700 mL) and pyridine (129 mL, 1.6 mol). The resulting solution was cooled in a water bath and trifluoroacetic anhydride (85 mL, 0.6 mol) was added dropwise under nitrogen. The bath was removed, and the mixture was stirred at ambient temperature for 16 h. The solution was cooled to 0° C. and concentrated HCl (150 mL) in water (1 L) was added dropwise. The organic layer was separated and concentrated, and ethyl acetate (0.5 L) was added. The resulting solution was treated with hydrogen gas under 50 psi in the presence of 5% Pd—C (80 g, 50% water wet) at ambient temperature for 16 h. The catalyst was filtered, and the filtrate was concentrated under vacuum to give 122 g of Methyl 3-(4-hydroxyphenyl)-2-methoxypropanoate as an oil. $^1$H-NMR (CDCl$_3$) δ 7.1 (d, 2H), 6.7 (d, 2H), 5.4 (s, 1H), 4.0 (m, 1H), 3.7 (s, 3H), 3.4 (s, 3H), 3.0 (m, 1H); MS (ES) m/z 209.2 (M−1).

Methyl 3-(4-hydroxyphenyl)-2-methoxypropanoate (132 g, 0.631 mol) was dissolved in methanol (700 mL) and 5N sodium hydroxide (631 mL, 3.16 mol) was added dropwise at ambient temperature. The solution was stirred for 16 h at ambient temperature. The methanol was removed under vacuum, and water (500 mL) was added. The mixture was extracted with MTBE (2×500 mL). The aqueous solution was brought to pH=1 with concentrated HCl and then extracted with MTBE (2×500 nL). The organic extracts were dried (MgSO$_4$), filtered, and concentrated under vacuum to give racemic 3-(4-hydroxyphenyl)-2-methoxypropanoic acid as an oil (110 g), which crystallized upon standing. $^1$H-NMR (DMSO): 7.0 (d, 2H); 6.6 (d, 2H); 4.0 (m, 1H); 2.8 (m, 2H); MS (ES$^-$) m/z 195.1 (M−1).

A slurry consisting of 3-(4-hydroxyphenyl)-2-methoxypropanoic acid (21.21 g, 0.1081 mol), (−)-cinchonidine (31.83 g, 0.1081 mol), and THF (424 mL) was heated briefly at reflux to give a red-brown solution. The mixture was cooled to ambient temperature and stirred for 3 days. The resulting slurry was cooled to 0° C. for 4 h and filtered to give about 17.06 g of the cinchonidine salt (71.2% ee by chiral HPLC). The cinchonidine salt was slurried in THF, heated to reflux for 1 hour, and cooled to ambient temperature overnight. The mixture was cooled to 0° C. for 2 h and filtered to give about 14.87 g of the cinchonidine salt (83.0% ee by chiral HPLC). The cinchonidine salt was slurried again in THF, and heated to reflux for 1 hour, and cooled to ambient temperature. The mixture was cooled to 0° C. for 2 h and filtered to give about 12.87 g (24%) of the cinchonidine salt of (2S)-3-(4-hydroxyphenyl)-2-methoxypropanoic acid (91.4% ee by chiral HPLC). Repeating the crystallization afforded compound of 98.1% ee. The free acid was obtained by suspending the salt (78 g) in 1N HCl solution (750 mL) and extracted with methyl tert-butyl ether (3×200 mL). The combined extracts were dried (Na$_2$SO$_4$) and concentrated to give about 24.12 g (82%) of (2S)-3-(4-hydroxyphenyl)-2-methoxypropanoic acid (96.7% ee by chiral HPLC). $^1$H NMR (DMSO-d$_6$): δ 2.72-2.89 (m, 2H), 3.21 (s, 3H), 3.8-3.87 (m, 1H), 6.64-6.67 (d, 2H), 6.97-7.02 (d, 2H), 9.15 (s, broad, 1H), 12.62 (s, broad, 1H); MS (ES$^+$) m/z 219.0 ([M+Na]$^+$), (ES$^-$) m/z 195.1 ([M−H]$^-$); [α]$_D$=−2.2° (c=1, MeOH).

A solution of (2S)-3-(4-hydroxyphenyl)-2-methoxypropanoic acid (35 g) in 140 ml of ethanol was mixed with 5.66 ml of concentrated sulfuric acid and stirred at room temperature until complete as indicated by HPLC. The ethanol was removed via vacuum distillation (55° C./28"Hg) and 110 ml of water was added. The pH was adjusted to about 7 to 8 with sodium bicarbonate, and the mixture was extracted with add 50 ml ethyl acetate (3×50 mL). The organic layers were combined, washed with 50 ml 20% NaCl solution, dried with 15 g of magnesium sulfate, and concentrate product to afford ethyl 2S-2-methoxy-3-(4-hydorxyphenyl) propanoate as an oil. $^1$H-NMR (CDCl$_3$) δ 7.1 (d, 2H); 6.7 (d, 2H); 4.2 (m, 2H); 3.9 (m, 1H); 3.6 (s, 3H); 2.95 (m, 2H); 1.25 (t, 3H); MS (ES): 223.2 (M−1).

Preparation 2

Step 1

3-(4-Benzyloxy-phenyl)-2-ethoxy-3-hydroxy-propionic acid ethyl ester

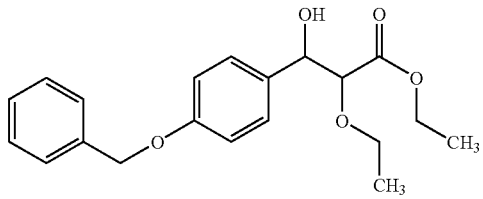

The title compound was prepared from 4-benzyloxybenzaldehyde, lithium diisopropylamide and ethyl 2-ethoxyacetate via the same procedure used for the preparation of 3-(3-benzyloxy-phenyl)-3-hydroxy-2-methoxy propionic acid methyl ester (example 9, step 1). MS (ES) for $C_{20}H_{24}O_5$ $[M+H_2O—H]^+$: 327, $[M+Na]^+$: 367.4.

Step 2

3-(4-Benzyloxy-phenyl)-2-ethoxy-acrylic acid ethyl ester

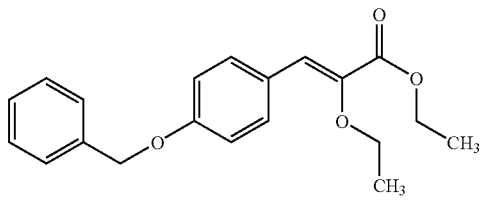

The title compound was prepared from 3-(4-Benzyloxy-phenyl)-2-ethoxy-3-hydroxy-propionic acid ethyl ester (Preparation 2, step 1) via the same procedure used for the preparation of 3-(4-Benzyloxy-phenyl)-2-ethoxy-acrylic acid methyl ester. MS (ES) for $C_{20}H_{22}O_4$ $[M+H]^+$: 327.2.

Step 3

3-(4-Benzyloxy-phenyl)-2-ethoxy-propionic acid methyl ester

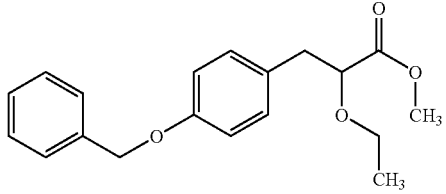

The title compound was prepared from 3-(4-Benzyloxy-phenyl)-2-ethoxy-acrylic acid ethyl ester (Preparation 2, step 2) (3.3 gr, 10.12 mmol) via the same procedure used for the preparation of 3-(3-Benzyloxy-phenyl)-2-methoxy-propionic acid methyl ester (example 9, step 3) to produce an oil that was purified by chromatography (silica gel, hexanes/ethyl acetate 6:1) to produce two compounds: 3-(4-Benzyloxy-phenyl)-propionic acid methyl ester (1.5 gr, Rf aprox. 0.65) and the desired compound (1.5 gr, Rf aprox. 0.2). MS (ES) for $C_{19}H_{22}O_4$ $[M+NH_4]^+$: 332.3.

Step 4

2-Ethoxy-3-(4-hydroxy-phenyl)-propionic acid methyl ester

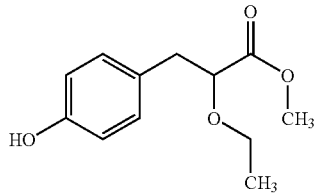

The title compound was prepared from 3-(4-Benzyloxy-phenyl)-2-ethoxy-propionic acid methyl ester (Preparation 2, step 3) via the same procedure used for the preparation of 3-(3-Hydroxy-phenyl)-2-methoxy-propionic acid methyl ester (example 9, step 4) to produce a yellow oil. MS (ES) for $C_{12}H_{16}O_4$ $[M+H]^+$: 225.2, $[M+NH_4]^+$: 242.2, $[+Na]^+$: 247.2.

Preparation 3

(2S)-2-methoxy-3-(4-{2-oxo-2-[4-(4-trifluoromethyl-phenyl)-piperazin-1-yl]-ethoxy}-phenyl)-propionic acid

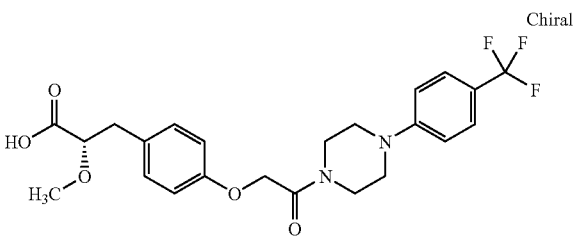

Step 1: (2S)-3-(4-tert-butoxycarbonylmethoxy-phenyl)-2-methoxy-propionic acid ethyl ester

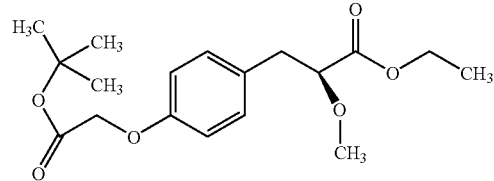

The compound of (2S)-3-(4-hydroxy-phenyl)-2-methoxy-propionic acid ester (Preparation 1), (1.2 g, 5.3 mmol) was dissolved in 25 ml of anhydrous THF and NaH (380 mg, 15.8 mmol) was added portion wise. After about 5 minutes, bromo-acetic acid tert-butyl ester was added dropwise at room temperature. The mixture was stirred for 2 hours at room temperature. The crude was dissolved in ethyl acetate (100 ml) and a solution of 5% HCl was added. The mixture was extracted with ethyl acetate (3×100 ml), and the combined organic layers were dried over (MgSO₄) and then concentrated under vacuum. The crude was purified by column chromatography (silica gel, hexane/ethyl acetate 8.5:1.5) to afford a yellow oil.

Step 2: (2S)-3-(4-carboxymethoxy-phenyl)-2-methoxy-propionic acid ethyl ester

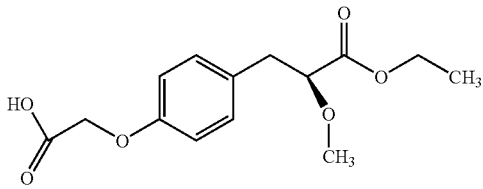

The compound of (2S)-3-(4-tert-butoxycarbonylmethoxy-phenyl)-2-methoxy-propionic acid ethyl ester (PREPARATION 3, step 1) (1.2 gr, 3.5 mmol) was solved in dichloromethane (5 ml) and trifluoroacetic acid was added (5 ml). The mixture was stirred for an hour, and the crude was concentrated to afford a yellow oil. ¹H-NMR (CDCl₃, 200.15 MHz): 7.16 (d, 2H, J=8.3), 6.75 (d, 2H, J=8.3), 4.89 (s, 2H), 4.14 (c, 2H, J=6.9), 3.94 (t, 1H, J=6.9), 3.57 (dc, 1H), 3.35 (dc, 1H), 2.92 (d, 2H, J=6.9), 1.23-1.10 (2t, 6H).

Step 3: (2S)-2-methoxy-3-(4-{2-oxo-2-[4-(4-trifluoromethyl-phenyl)-piperazin-1-yl]-ethoxy}-phenyl)-propionic acid

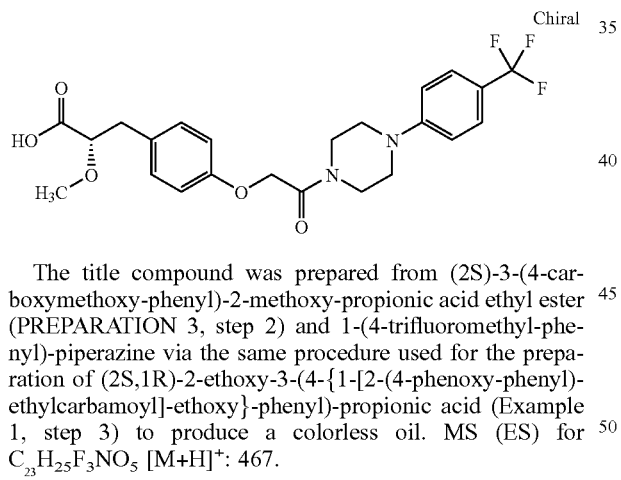

The title compound was prepared from (2S)-3-(4-carboxymethoxy-phenyl)-2-methoxy-propionic acid ethyl ester (PREPARATION 3, step 2) and 1-(4-trifluoromethyl-phenyl)-piperazine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for C₂₃H₂₅F₃NO₅ [M+H]⁺: 467.

Preparation 4

3-(3-{[2-(4-ethyl-phenyl)-ethylcarbamoyl]-methoxy}-phenyl)-2-methoxy-propionic acid (isomer 1)

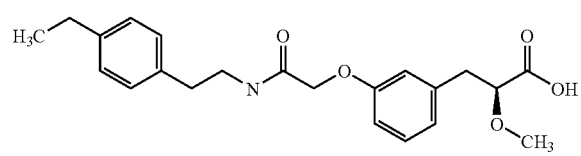

Step 1: 3-(3-tert-butoxycarbonylmethoxy-phenyl)-2-methoxy-propionic acid methyl ester

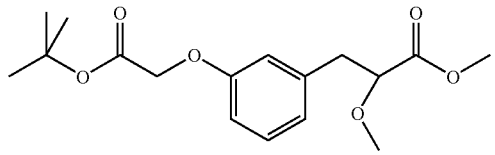

The title compound was prepared from 3-(3-hydroxy-phenyl)-2-methoxy-propionic acid methyl ester (example 9, step 4) via the same procedure used to prepare (2S)-3-(4-tert-butoxycarbonylmethoxy-phenyl)-2-methoxy-propionic acid ethyl ester (PREPARATION 3, step 1) to produce a yellow oil. MS (ES) for C₁₇H₂₄O₆ [M+H]⁺: 325.

Step 2: 3-(3-carboxymethoxy-phenyl)-2-methoxy-propionic acid methyl ester

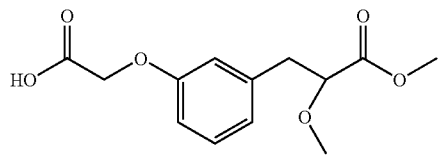

The title compound was prepared from 3-(3-tert-butoxycarbonylmethoxy-phenyl)-2-methoxy-propionic acid methyl ester (PREPARATION 4, step 1) via the same procedure used to prepare (2S)-3-(4-carboxymethoxy-phenyl)-2-methoxy-propionic acid ethyl ester (PREPARATION 3, step 2) to produce a yellow oil. MS (ES) for C₁₃H₁₆O₆ [M+H]⁺: 269.

Step 3: 3-(3-{[2-(4-ethyl-phenyl)-ethylcarbamoyl]-methoxy}-phenyl)-2-methoxy-propionic acid (isomer-1)

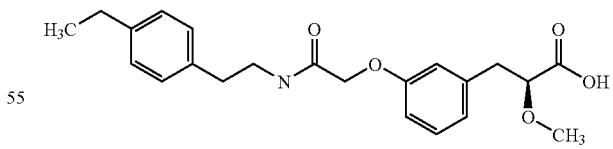

The title compound was prepared from 3-(3-carboxymethoxy-phenyl)-2-methoxy-propionic acid methyl ester (PREPARATION 4, step 2) and 2-(4-ethyl-phenyl)-ethylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for C₂₂H₂₇NO₅ [M+H]⁺: 386.

Preparation 5

(2S)-2-methoxy-3-[4-(1-methyl-1-octylcarbamoyl-ethoxy)-phenyl]-propionic acid

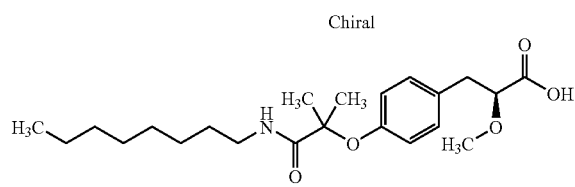

Step 1: (2S)-3-[4-(1-tert-butoxycarbonyl-1-methyl-ethoxy)-phenyl]-2-methoxy-propionic acid ethyl ester

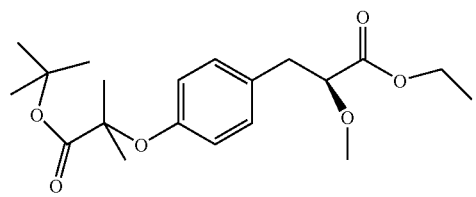

The title compound was prepared from (2S)-3-(4-hydroxy-phenyl)-2-methoxy-propionic acid ester (Preparation 1) and 2-bromo-2-methyl-propionic acid tert-butyl ester via the same procedure used to prepare (2S)-3-(4-tert-butoxycarbonylmethoxy-phenyl)-2-methoxy-propionic acid ethyl ester (example 121, step 1) to produce a yellow oil.

$^1$H-NMR (CDCl$_3$, 200.15 MHz): δ 7.10 (d, 2H, J=8.3), 6.77 (d, 2H, J=8.3), 4.17 (c, 2H, J=6.9), 3.90 (t, 1H, J=6.5), 3.34 (s, 3H), 2.93 (d, 2H, J=6.5), 1.55 (s, 3H), 1.43 (s, 9H), 1.23-1.4 (t, 3H, J=6.9).

Step 2: (2S)-3-[4-(1-carboxy-1-methyl-ethoxy)-phenyl]-2-methoxy-propionic acid ethyl ester

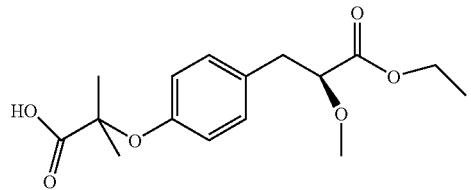

The title compound was prepared from (2S)-3-[4-(1-tert-butoxycarbonyl-1-methyl-ethoxy)-phenyl]-2-methoxy-propionic acid ethyl ester (PREPARATION 5, step 1) via the same procedure used to prepare (2S)-3-(4-carboxymethoxy-phenyl)-2-methoxy-propionic acid ethyl ester (example 121, step 2) to produce a yellow oil. $^1$H-NMR (CDCl$_3$, 200.15 MHz): 7.10 (d, 2H, J=8.3), 6.77 (d, 2H, J=8.3), 4.14 (c, 2H, J=6.9), 3.89 (t, 1H, J=6.5), 3.34 (s, 3H), 2.94 (d, 2H, J=6.5), 1.55 (s, 6H), 1.19 (t, 3H, J=6.9).

Step 3: (2S)-2-methoxy-3-[4-(1-methyl-1-octylcarbamoyl-ethoxy)-phenyl]-propionic acid

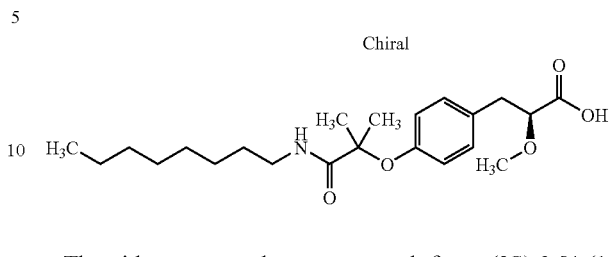

The title compound was prepared from (2S)-3-[4-(1-carboxy-1-methyl-ethoxy)-phenyl]-2-methoxy-propionic acid ethyl ester (PREPARATION 5, step 2) and heptylamine via the same procedure used for the preparation of (2S, 1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for C$_{21}$H$_{33}$NO$_5$ [M+H]$^+$: 380.

EXAMPLE 1

(2S,1'R)-2-Ethoxy-3-(4-{1'-[2-(4-phenoxy-phenyl)-ethylcarbamoyl]-ethoxy}-phenyl)-propionic acid

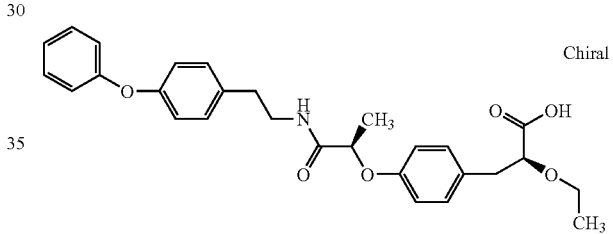

Step 1: (2S,1'R)-3-[4-(1'-benzyloxycarbonyl-ethoxy)-phenyl]-2-ethoxy-propionic acid ethyl ester

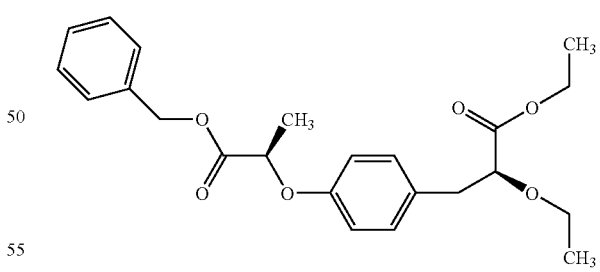

The title compound was prepared from (2S)-2-ethoxy-3-(4-hydroxy-phenyl)-propionic acid methyl ester (isomer 2 of Preparation 2, step 4 after chiral separation) (2.9 mmol) and (2S)-2-hydroxy-propionic acid benzyl ester (4.35 mmol) via the same procedure used for the preparation of (2S)-3-[4-(3-bromo-propoxy)-phenyl]-2-methoxy-propionic acid ethyl ester (Preparation 1, step 2) and purified by chromatography (silica gel, hexanes/ethyl acetate 6:1, Rf 0.27) to produce a colorless oil. MS (ES) for C$_{23}$H$_{28}$O$_6$ [M+NH4]$^+$: 418.2, [M+Na]$^+$: 423.2.

Step 2: (2S,1'R)-3-[4-(1'-carboxy-ethoxy)-phenyl]-2-ethoxy-propionic acid

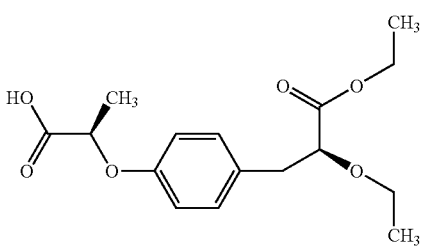

The title compound was prepared from (2S,1R)-3-[4-(1-benzyloxycarbonyl-ethoxy)-phenyl]-2-ethoxy-propionic acid ethyl ester (Preparation 1) via the same procedure used for the preparation of 3-(3-hydroxy-phenyl)-2-methoxy-propionic acid methyl ester (example 9, step 4) to produce a yellow oil. MS (ES) for $C_{16}H_{22}O_6$ $[M+NH_4]^+$: 328.2.

Step 3: (2S,1'R)-2-ethoxy-3-(4-{1'-[2-(4-phenoxy-phenyl)-ethylcarbamoyl]-ethoxy}-phenyl)-propionic acid

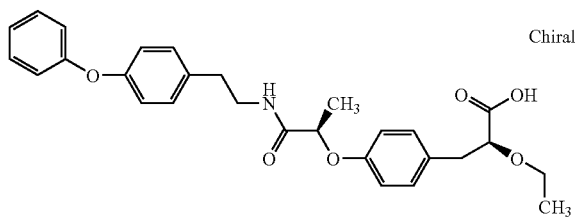

(2S,1'R)-3-[4-(1'-carboxy-ethoxy)-phenyl]-2-ethoxy-propionic acid (Example 1, step 2) (0.1 mmol) was dissolved in dichlromethane in a 16×100 mm tube, triethylamine (0.15 mmol), eimethylaminopyridine (0.01 mmol), PyBroP (0.2 mmol) and 2-(4-phenoxy-phenyl)-ethylamine (0.15 mmol) were added and the mixture was stirred overnight at room temperature. The mixture was concentrated to dryness under vacuum. The crude was dissolved in MeOH and charged into a 500 mg SCX column (previously pre-conditioned with MeOH). The column was washed (2×2 ml) with MeOH. The crude was concentrated, and the residue reconstituted in a mixture of Ethanol (2 ml) and NaOH (1M in water, 1 mL), which was stirred at room temperature until the hydrolysis was completed by HPLC-MS. Then HCl (1M in water) was added (until pH=3) and the solvent was eliminated under vacuum. The residue was reconstituted in $CH_2Cl_2/H_2O$ and filtered through a hydrophobic syringe. The organic layer was separated, concentrated and purified by HPLC-MS to produce the compound as a colorless oil. MS (ES) for $C_{28}H_{31}NO_6$ $[M+H]^+$: 478.2.

EXAMPLE 2

(2S,1'R)-2-Ethoxy-3-(4-{1'-[2-(4-ethyl-phenyl)-ethylcarbamoyl]-ethoxy}-phenyl)-propionic acid

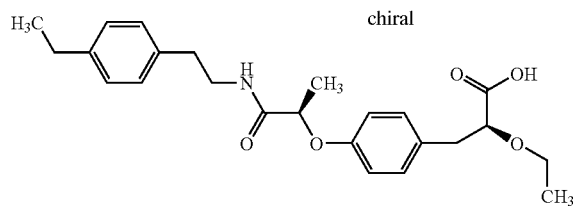

The title compound was prepared from 2-(4-ethyl-phenyl)-ethylamine and (2S,1'R)-3-[4-(1'-carboxy-ethoxy)-phenyl]-2-ethoxy-propionic acid (Example 1, step 2) via the same procedure used for the preparation of (2S,1'R)-2-ethoxy-3-(4-{1'-[2-(4-phenoxy-phenyl)-ethylcarbamoyl]-ethoxy}-phenyl)-propionic acid (Example 1, step 3) to produce a colorless oil. MS (ES) for $C_{24}H_{31}NO_5$ $[M+H]^+$: 414.2.

EXAMPLE 3

(2S,1'R)-2-ethoxy-3-(4-{1'-[2-(4-trifluoromethyl-phenyl)-ethylcarbamoyl]-ethoxy}-phenyl)-propionic acid

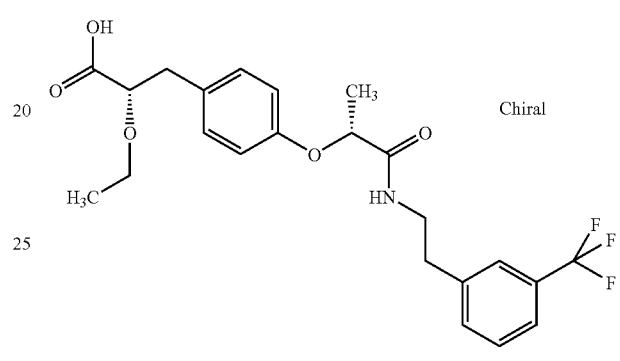

The title compound was prepared from 2-(4-tifluoromethyl-phenyl)-ethylamine and (2S,1'R)-3-[4-(1'-Carboxy-ethoxy)-phenyl]-2-ethoxy-propionic acid (Example 1, step 2) via the same procedure used for the preparation of (2S,1'R)-2-ethoxy-3-(4-{1'-[2-(4-phenoxy-phenyl)-ethylcarbamoyl]-ethoxy}-phenyl)-propionic acid (Example 1, step 3) to produce a colorless oil. MS (ES) for $C_{23}H_{26}F_3NO_5$ $[M+H]^+$: 454.2, $[M-H]^-$: 452.2

EXAMPLE 4

(2S,1'R)-3-{4-[1'-(4-tert-butyl-cyclohexylcarbamoyl)-ethoxy]-phenyl}-2-ethoxy-propionic acid

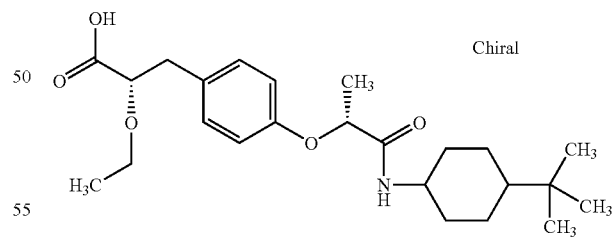

The title compound was prepared from a mixture of cis/trans (2:3) of 4-tert-butyl-cyclohexylamine and (2S,1'R)-3-[4-(1'-carboxy-ethoxy)-phenyl]-2-ethoxy-propionic acid (Example 1, step 2) via the same procedure used for the preparation of (2S,1'R)-2-ethoxy-3-(4-{1'-[2-(4-phenoxy-phenyl)-ethylcarbamoyl]-ethoxy}-phenyl)-propionic acid (Example 1, step 3) to produce a colorless oil.

MS (ES) for $C_{24}H_{37}NO_5$ $[M+H]^+$:420.3, $[M+NH_4]^+$: 442.3, $[M+H]^+$: 4.18.2

EXAMPLE 5

(2S,1'R)-2-ethoxy-3-(4-{1'-[2-(2-ethoxy-phenyl)-ethylcarbamoyl]-ethoxy}-phenyl)-propionic acid

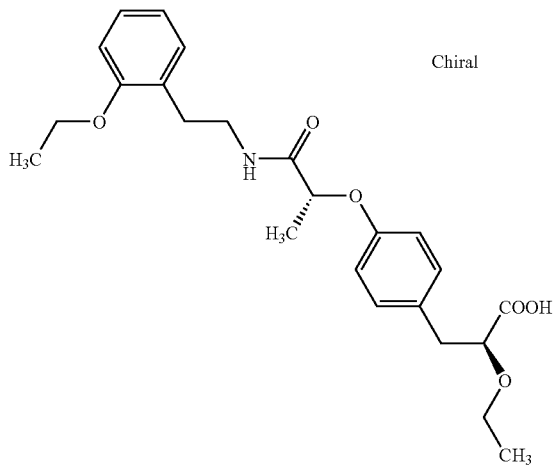

The title compound was prepared from 2-(2-ethoxy-phenyl)-ethylamine and (2S,1'R)-3-[4-(1'-carboxy-ethoxy)-phenyl]-2-ethoxy-propionic acid (Example 1, step 2) via the same procedure used for the preparation of (2S,1'R)-2-ethoxy-3-(4-{1'-[2-(4-phenoxy-phenyl)-ethylcarbamoyl]-ethoxy}-phenyl)-propionic acid (Example 1, step 3) to produce a colorless oil. MS (ES) for $C_{24}H_{31}NO_6$ [M+H]$^+$: 430.2.

EXAMPLE 6

(2S,1'R)-2-ethoxy-3-{4-[1'-(3-trifluoromethyl-benzylcarbamoyl)-ethoxy]-phenyl}-propionic acid

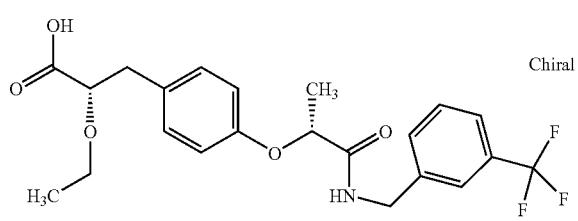

The title compound was prepared from 3-trifluoromethyl-benzylamine and (2S,1'R)-3-[4-(1'-carboxy-ethoxy)-phenyl]-2-ethoxy-propionic acid (Example 1, step 2) via the same procedure used for the preparation of (2S,1'R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{22}H_{24}F_3NO_5$ [M+H]$^+$: 440.2.

EXAMPLE 7

(2S,1'R)-2-ethoxy-3-{4-[1'-(3-fluoro-5-trifluoromethyl-benzylcarbamoyl)-ethoxy]-phenyl}-propionic acid

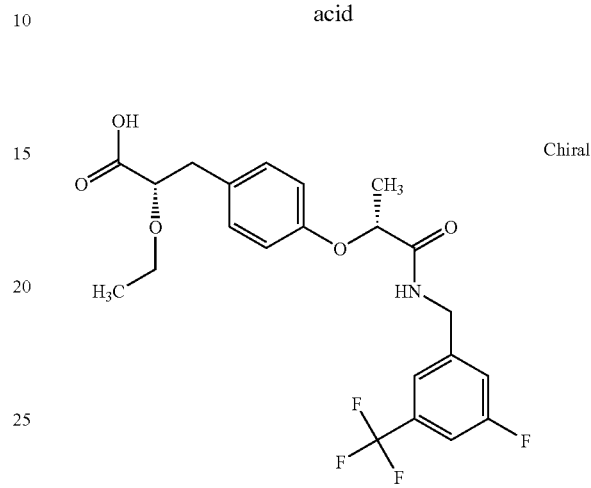

The title compound was prepared from 3-fluoro-5-trifluoromethyl-benzylamine and (2S,1'R)-3-[4-(1'-Carboxy-ethoxy)-phenyl]-2-ethoxy-propionic acid (Example 1, step 2) via the same procedure used for the preparation of (2S,1'R)-2-ethoxy-3-(4-{1'-[2-(4-phenoxy-phenyl)-ethylcarbamoyl]-ethoxy}-phenyl)-propionic acid (Example 1, step 3) to produce a colorless oil. MS (ES) for $C_{22}H_{23}F_4NO_5$ [M−H]$^-$: 456.1.

EXAMPLE 8

(2S,1'R)-3-(4-{1'-[(biphenyl-3-ylmethyl)-carbamoyl]-ethoxy}-phenyl)-2-ethoxy-propionic acid

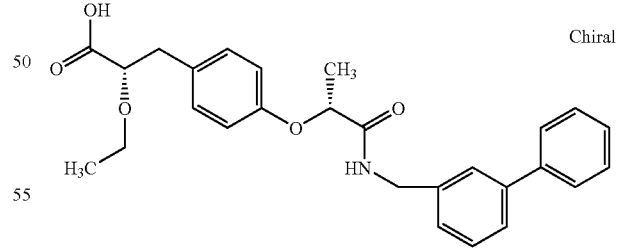

The title compound was prepared from C-biphenyl-3-yl-methylamine and (2S,1'R)-3-[4-(1'-carboxy-ethoxy)-phenyl]-2-ethoxy-propionic acid (Example 1, step 2) via the same procedure used for the preparation of (2S,1'R)-2-Ethoxy-3-(4-{1'-[2-(4-phenoxy-phenyl)-ethylcarbamoyl]-ethoxy}-phenyl)-propionic acid (Example 1, step 3) to produce a colorless oil. MS (ES) for $C_{27}H_{29}NO_5$ [M+H]$^+$: 448.2.

EXAMPLE 9

(2S,1'R)-3-(4-{1'-[2-(3-chloro-phenyl)-ethylcarbamoyl]-ethoxy}-phenyl)-2-ethoxy-propionic acid

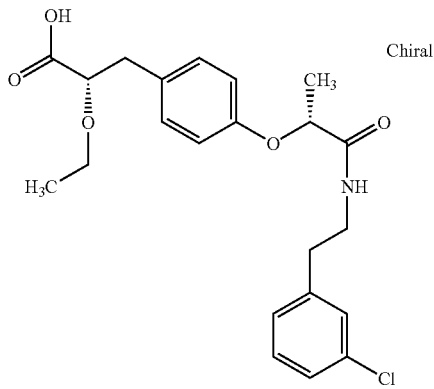

The title compound was prepared from 2-(3-chloro-phenyl)-ethylamine and (2S,1'R)-3-[4-(1'-carboxy-ethoxy)-phenyl]-2-ethoxy-propionic acid (Example 1, step 2) via the same procedure used for the preparation of (2S,1'R)-2-ethoxy-3-(4-{1'-[2-(4-phenoxy-phenyl)-ethylcarbamoyl]-ethoxy}-phenyl)-propionic acid (Example 1, step 3) to produce a colorless oil. MS (ES) for $C_{22}H_{26}ClNO_5$ $[M+H]^+$: 420.2.

EXAMPLE 10

(2S,1'R)-2-ethoxy-3-(4-{1'-[2-(3-fluoro-phenyl)-ethylcarbamoyl]-ethoxy}-phenyl)-propionic acid

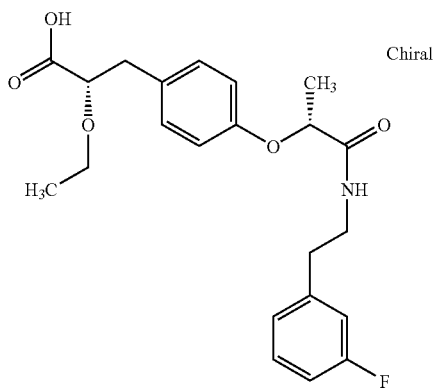

The title compound was prepared from [2-(3-fluoro-phenyl)-ethyl]-methyl-amine and (2S,1'R)-3-[4-(1'-carboxy-ethoxy)-phenyl]-2-ethoxy-propionic acid (Example 1, step 2) via the same procedure used for the preparation of (2S,1'R)-2-ethoxy-3-(4-{1'-[2-(4-phenoxy-phenyl)-ethylcarbamoyl]-ethoxy}-phenyl)-propionic acid (Example 1, step 3) to produce a colorless oil. MS (ES) for $C_{22}H_{26}FNO_5$ $[M+H]^+$: 404.2.

EXAMPLE 11

(2S,1'R)-2-ethoxy-3-(4-{1'-[2-(2-fluoro-phenyl)-ethylcarbamoyl]-ethoxy}-phenyl)-propionic acid

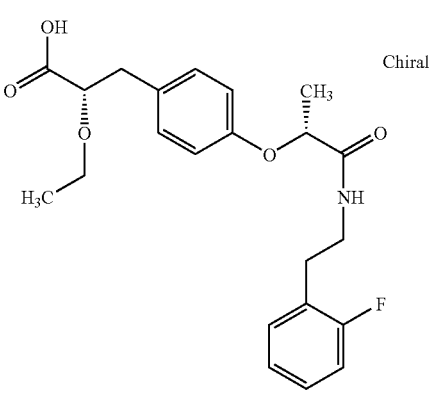

The title compound was prepared from [2-(2-fluoro-phenyl)-ethyl]-methyl-amine and (2S,1'R)-3-[4-(1'-carboxy-ethoxy)-phenyl]-2-ethoxy-propionic acid (Example 1, step 2) via the same procedure used for the preparation of (2S,1'R)-2-ethoxy-3-(4-{1'-[2-(4-phenoxy-phenyl)-ethylcarbamoyl]-ethoxy}-phenyl)-propionic acid (Example 1, step 3) to produce a colorless oil. MS (ES) for $C_{22}H_{26}FNO_5$ $[M+H]^+$: 404.2.

EXAMPLE 12

(2S,1'R)-3-(4-{1'-[2-(2,4-dichloro-phenyl)-ethylcarbamoyl]-ethoxy}-phenyl)-2-ethoxy-propionic acid

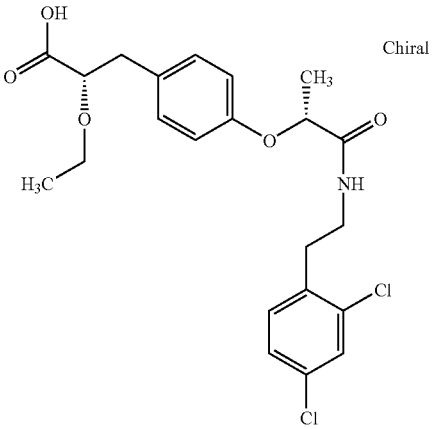

The title compound was prepared from 2-(2,4-dichloro-phenyl)-ethylamine and (2S,1'R)-3-[4-(1'-carboxy-ethoxy)-phenyl]-2-ethoxy-propionic acid (Example 1, step 2) via the same procedure used for the preparation of (2S,1'R)-2-ethoxy-3-(4-{1'-[2-(4-phenoxy-phenyl)-ethylcarbamoyl]-ethoxy}-phenyl)-propionic acid (Example 1, step 3) to produce a colorless oil. MS (ES) for $C_{22}H_{25}Cl_2NO_5$ $[M+H]^+$: 454.1.

EXAMPLE 13

(2S,1'R)-3-(4-{1'-[2-(2,6-dichloro-phenyl)-ethylcarbamoyl]-ethoxy}-phenyl)-2-ethoxy-propionic acid

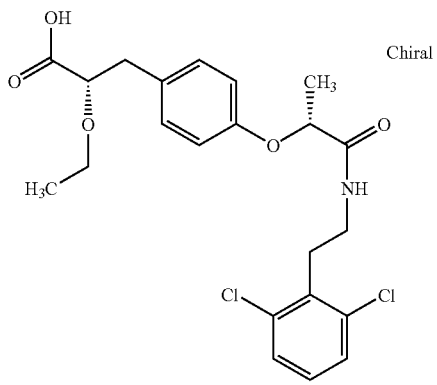

The title compound was prepared from 2-(2,6-dichloro-phenyl)-ethylamine and (2S,1'R)-3-[4-(1'-carboxy-ethoxy)-phenyl]-2-ethoxy-propionic acid (Example 1, step 2) via the same procedure used for the preparation of (2S,1'R)-2-ethoxy-3-(4-{1'-[2-(4-phenoxy-phenyl)-ethylcarbamoyl]-ethoxy}-phenyl)-propionic acid (Example 1, step 3) to produce a colorless oil. MS (ES) for $C_{22}H_{25}Cl_2NO_5$ [M+H]$^+$: 454.1.

EXAMPLE 14

(2S,1'R)-2-ethoxy-3-[4-(1'-heptylcarbamoyl-ethoxy)-phenyl]-propionic acid

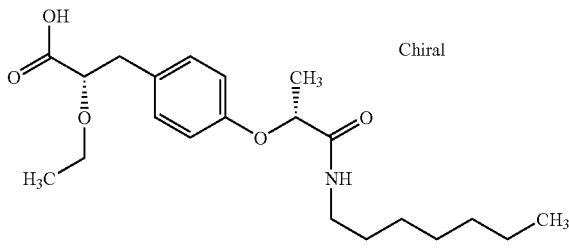

The title compound was prepared from heptylamine and (2S,1'R)-3-[4-(1'-Carboxy-ethoxy)-phenyl]-2-ethoxy-propionic acid (Example 1, step 2) via the same procedure used for the preparation of (2S,1'R)-2-ethoxy-3-(4-{1'-[2-(4-phenoxy-phenyl)-ethycarbmoyl]-ethoxy}-phenyl)-propionic acid (Example 1, step 3) to produce a colorless oil. MS (ES) for $C_{21}H_{33}NO_5$ [M+H]$^+$: 380.3.

EXAMPLE 15

(2S,1'R)-3-(4-{1'-[2-(2-chloro-phenyl)-ethylcarbamoyl]-ethoxy}-phenyl)-2-ethoxy-propionic acid

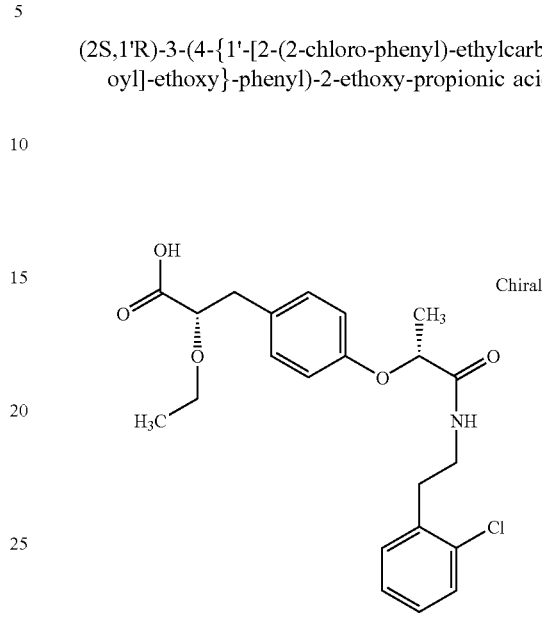

The title compound was prepared from 2-(2-chloro-phenyl)-ethylamine and (2S,1'R)-3-[4-(1'-carboxy-ethoxy)-phenyl]-2-ethoxy-propionic acid (Example 1, step 2) via the same procedure used for the preparation of (2S,1'R)-2-ethoxy-3-(4-{1'-[2-(4-phenoxy-phenyl)-ethylcarbamoyl]-ethoxy}-phenyl)-propionic acid (Example 1, step 3) to produce a colorless oil. MS (ES) for $C_{22}H_{26}ClNO_5$ [M+H]$^+$: 420.2.

EXAMPLE 16

(2S,1'R)-3-(4-{1'-[2-(4-tert-butyl-phenyl)-ethylcarbamoyl]-ethoxy}-phenyl)-2-ethoxy-propionic acid

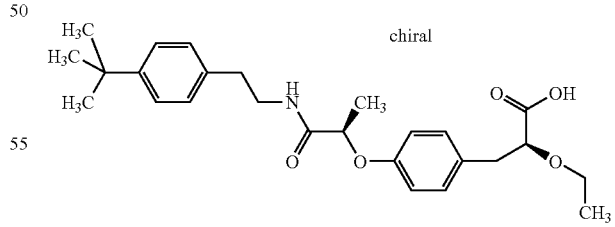

The title compound was prepared from 2-(4-tert-butyl-phenyl)-ethylamine and (2S,1'R)-3-[4-(1'-carboxy-ethoxy)-phenyl]-2-ethoxy-propionic acid (Example 1, step 2) via the same procedure used for the preparation of (2S,1'R)-2-ethoxy-3-(4-{1'-[2-(4-phenoxy-phenyl)-ethylcarbamoyl]-ethoxy}-phenyl)-propionic acid (Example 1, step 3) to produce a colorless oil. MS (ES) for $C_{26}H_{35}NO$ [M+H]$^+$: 442.5.

EXAMPLE 17

(2S,1'R)-2-ethoxy-3-{4-[1'-(4-fluoro-benzylcarbamoyl)-ethoxy]-phenyl}-propionic acid

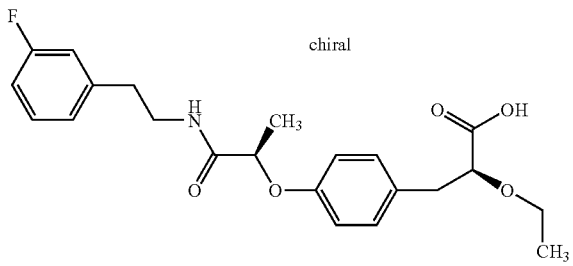

The title compound was prepared from 4-fluoro-benzylamine and (2S,1'R)-3-[4-(1'-carboxy-ethoxy)-phenyl]-2-ethoxy-propionic acid (Example 1, step 2) via the same procedure used for the preparation of (2S,1'R)-2-ethoxy-3-(4-{1'-[2-(4-phenoxy-phenyl)-ethylcarmoyl]-ethoxy}-phenyl)-propionic acid (Example 1, step 3) to produce a colorless oil. MS (ES) for $C_{21}H_{24}FNO_5$ [M+H]$^+$: 390.4.

EXAMPLE 18

(2S,1'R)-2-ethoxy-3-{4-[1'-(4-trifluoromethyl-benzylcarbamoyl)-ethoxy]-phenyl}-propionic acid

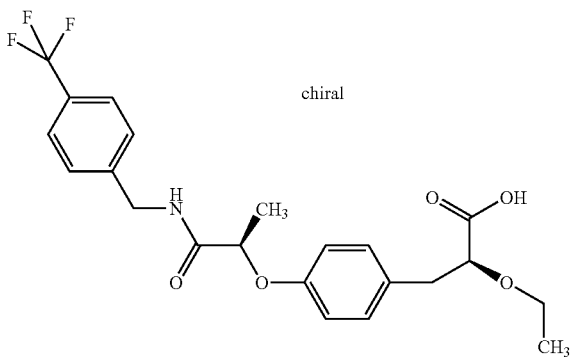

The title compound was prepared from 4-trifluoromethyl-benzylamine and (2S,1'R)-3-[4-(1'-Carboxy-ethoxy)-phenyl]-2-ethoxy-propionic acid (Example 1, step 2) via the same procedure used for the preparation of (2S,1'R)-2-ethoxy-3-(4-{1'-[2-(4-phenoxy-phenyl)-ethylcarbamoyl]-ethoxy}-phenyl)-propionic acid (Example 1, step 3) to produce a colorless oil. MS (ES) for $C_{22}H_{24}F_3NO_5$ [M+H]$^+$: 440.3.

EXAMPLE 19

(2S,1'R)-2-ethoxy-3-{4-[1'-(2-thiophen-2-yl-ethylcarbamoyl)-ethoxy]-phenyl}-propionic acid

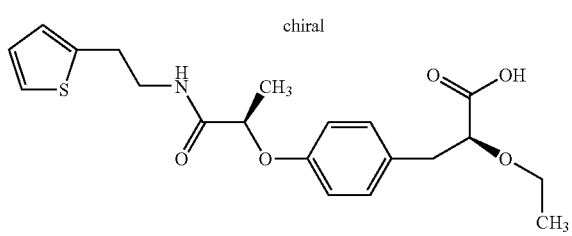

The title compound was prepared from 2-thiophen-2-yl-ethylamine and (2S,1'R)-3-[4-(1'-carboxy-ethoxy)-phenyl]-2-ethoxy-propionic acid (Example 1, step 2) via the same procedure used for the preparation of (2S,1'R)-2-ethoxy-3-(4-{1'-[2-(4-phenoxy-phenyl)-ethycarmoyl]-ethoxy}-phenyl)-propionic acid (Example 1, step 3) to produce a yellow oil. MS (ES) for $C_{20}H_{25}NO_5S$ [M+H]$^+$: 392.3.

EXAMPLE 20

(2S,1'R)-2-ethoxy-3-(4-{1'-[(thiophen-2-ylmethyl)-carbamoyl]-ethoxy}-phenyl)-propionic acid

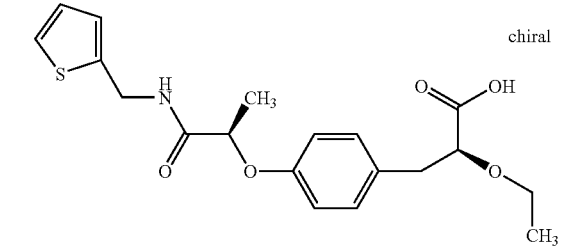

The title compound was prepared from C-thiophen-2-yl-methylamine and (2S,1'R)-3-[4-(1'-carboxy-ethoxy)-phenyl]-2-ethoxy-propionic acid (Example 1, step 2) via the same procedure used for the preparation of (2S,1'R)-2-ethoxy-3-(4-{1'-[2-(4-phenoxy-phenyl)-ethylcarbamoyl]-ethoxy}-phenyl)-propionic acid (Example 1, step 3) to produce a yellow oil. MS (ES) for $C_{19}H_{23}NO_5S$ [M+H]$^+$: 378.3.

EXAMPLE 21

(2S,1'R)-3-{4-[1'-(4-tert-butyl-benzylcarbamoyl)-ethoxy]-phenyl}-2-ethoxy-propionic acid

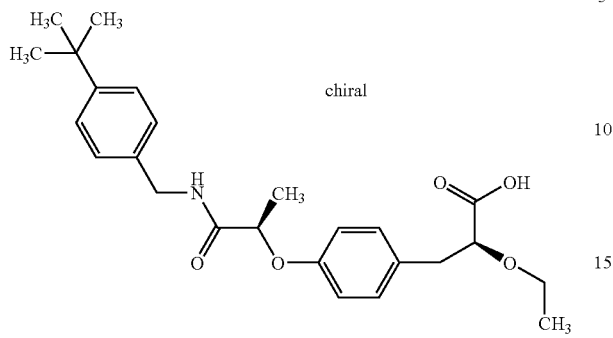

The title compound was prepared from 4-tert-butyl-benzylamine and (2S,1'R)-3-[4-(1'-carboxy-ethoxy)-phenyl]-2-ethoxy-propionic acid (Example 1, step 2) via the same procedure used for the preparation of (2S,1'R)-2-ethoxy-3-(4-{1'-[2-(4-phenoxy-phenyl)-ethycarmoyl]-ethoxy}-phenyl)-propionic acid (Example 1, step 3) to produce a colorless oil. MS (ES) for $C_{25}H_{33}NO_5$ [M+H]$^+$: 428.4.

EXAMPLE 22

(2S,1'R)-3-{4-[1'-(4-tert-butyl-phenylcarbamoyl)-ethoxy]-phenyl}-2-ethoxy-propionic acid

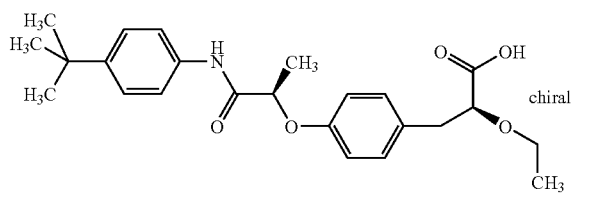

The title compound was prepared from 4-tert-butyl-phenylamine and (2S,1'R)-3-[4-(1'-carboxy-ethoxy)-phenyl]-2-ethoxy-propionic acid (Example 1, step 2) via the same procedure used for the preparation of (2S,1'R)-2-ethoxy-3-(4-{1'-[2-(4-phenoxy-phenyl)-ethylcarmoyl]-ethoxy}-phenyl)-propionic acid (Example 1, step 3) to produce a colorless oil. MS (ES) for $C_{24}H_{31}NO_5$ [M+H]$^+$: 414.4.

EXAMPLE 23

(2S,1'R)-3-{4-[1'-(4-trans-tert-butyl-cyclohexylcarbamoyl-ethoxy]-phenyl}-2-ethoxy-propionic acid

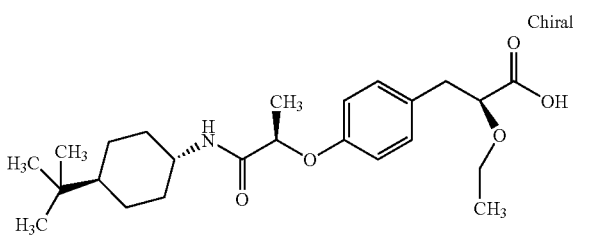

The title compound was prepared from trans 4-tert-butyl-cyclohexylamine and (2S,1'R)-3-[4-(1'-carboxy-ethoxy)-phenyl]-2-ethoxy-propionic acid (Example 1, step 2) via the same procedure used for the preparation of (2S,1'R)-2-ethoxy-3-(4-{1'-[2-(4-phenoxy-phenyl)-ethylcarbamoyl]-ethoxy}-phenyl)-propionic acid (Example 1, step 3) to produce a colorless oil. MS (ES) for $C_{24}H_{37}NO_5$ [M+H]$^+$: 420.3, [M+NH$_4$]$^+$: 442.3.

EXAMPLE 24

(2S)-3-[4-({ethyl-[2-(4-methoxy-phenyl)-1-methyl-ethyl]-carbamoyl}-methoxy)-phenyl]-2-methoxy-propionic acid

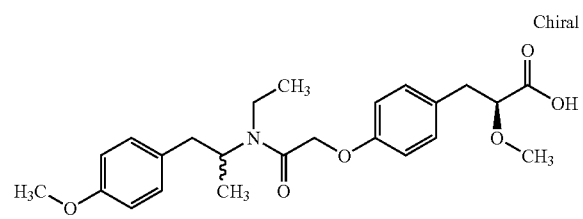

The title compound was prepared from (2S)-3-(4-carboxymethoxy-phenyl)-2-methoxy-propionic acid ethyl ester (PREPARATION 3, step 2) and ethyl-[2-(4-methoxy-phenyl)-1-methyl-ethyl]-amine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{24}H_{31}NO_6$ [M+H]$^+$: 430.

EXAMPLE 25

(2S)-2-methoxy-3-{4-[(1-naphthalen-1-yl-ethylcarbamoyl)-methoxy]-phenyl}-propionic acid

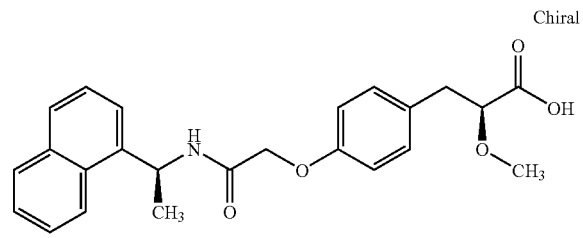

The title compound was prepared from (2S)-3-(4-carboxymethoxy-phenyl)-2-methoxy-propionic acid ethyl ester (PREPARATION 3, step 2) and 1-naphthalen-1-yl-ethylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{24}H_{25}NO_5$ [M+H]$^+$: 408.

EXAMPLE 26

(2S)-2-methoxy-3-{4-[(1-Phenyl-ethylcarbamoyl)-methoxy]-phenyl}-propionic acid

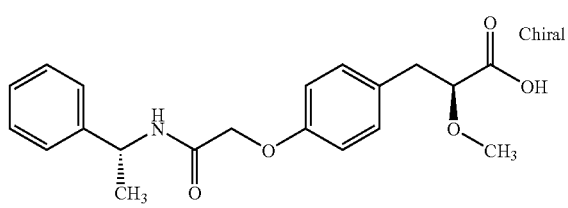

The title compound was prepared from (2S)-3-(4-carboxymethoxy-phenyl)-2-methoxy-propionic acid ethyl ester (PREPARATION 3, step 2) and 1-phenyl-ethylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{20}H_{23}NO_5$ [M+H]$^+$: 358.

EXAMPLE 27

(2S)-2-methoxy-3-(4-{[methyl-(1-phenyl-ethyl)-carbamoyl]-methoxy}-phenyl)-propionic acid

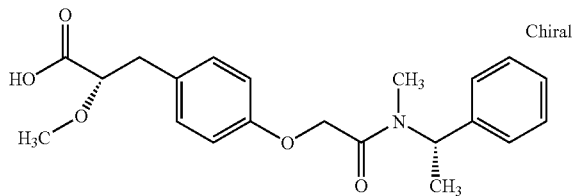

The title compound was prepared from (2S)-3-(4-carboxymethoxy-phenyl)-2-methoxy-propionic acid ethyl ester (PREPARATION 3, step 2) and methyl-(1-phenyl-ethyl)-amine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{21}H_{25}NO_5$ [M+H]$^+$: 372.

EXAMPLE 28

(2S)-3-(4-{2-[4-(4-fluoro-benzoyl)-piperidin-1-yl]-2-oxo-ethoxy}-phenyl)-2-methoxy-propionic acid

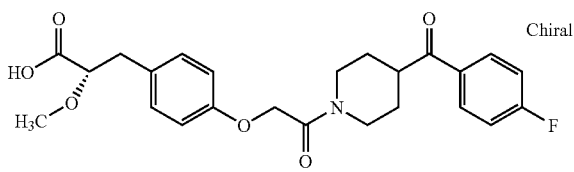

The title compound was prepared from (2S)-3-(4-carboxymethoxy-phenyl)-2-methoxy-propionic acid ethyl ester (PREPARATION 3, step 2) and (4-fluoro-phenyl)-piperidin-4-yl-methanone via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{24}H_{26}FNO_6$ [M+H]$^+$: 444.

EXAMPLE 29

(2S)-3-(4-{2-[4-(4-chloro-benzoyl)-piperidin-1-yl]-2-oxo-ethoxy}-phenyl)-2-methoxy-propionic acid

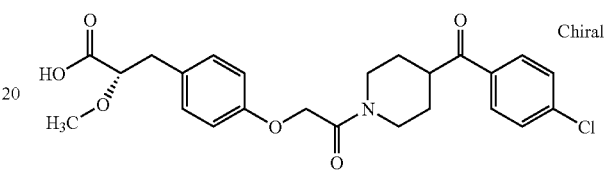

The title compound was prepared from (2S)-3-(4-carboxymethoxy-phenyl)-2-methoxy-propionic acid ethyl ester (PREPARATION 3, step 2) and (4-chloro-phenyl)-piperidin-4-yl-methanone via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a yellow oil. MS (ES) for $C_{24}H_{26}ClNO_6$ [M+H]$^+$: 460.

EXAMPLE 30

(2S)-2-methoxy-3-{4-[(1-methoxycarbonyl-2-phenyl-ethylcarbamoyl)-methoxy]-phenyl}-propionic acid

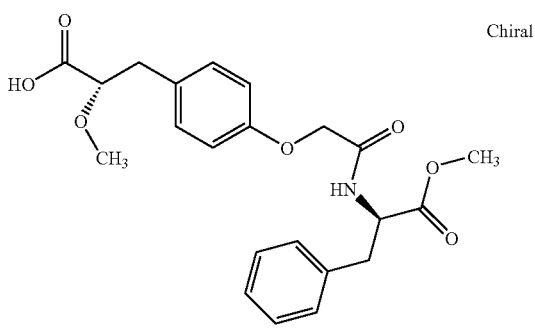

The title compound was prepared from (2S)-3-(4-carboxymethoxy-phenyl)-2-methoxy-propionic acid ethyl ester (PREPARATION 3, step 2) and 2-amino-3-phenyl-propionic acid methyl ester via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{22}H_{25}NO_7$ [M+H]$^+$: 416.

EXAMPLE 31

(2S)-3-[4-(2-{4-[(4-chloro-phenyl)-phenyl-methyl]-piperazin-1-yl}-2-oxo-ethoxy)-phenyl]-2-methoxy-propionic acid

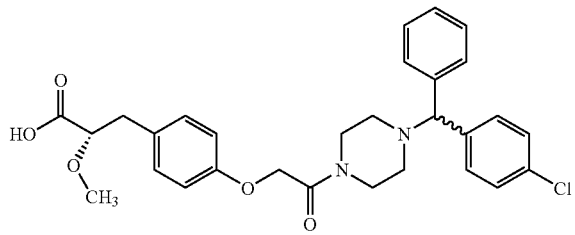

The title compound was prepared from (2S)-3-(4-carboxymethoxy-phenyl)-2-methoxy-propionic acid ethyl ester (PREPARATION 3, step 2) and 1-[(4-chloro-phenyl)-phenyl-methyl]-piperazine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{29}H_{31}ClN_2O_5$ [M+H]$^+$: 524.

EXAMPLE 32

(2S)-3-[4-({[(4-chloro-phenyl)-phenyl-methyl]-carbamoyl}-methoxy)-phenyl]-2-methoxy-propionic acid

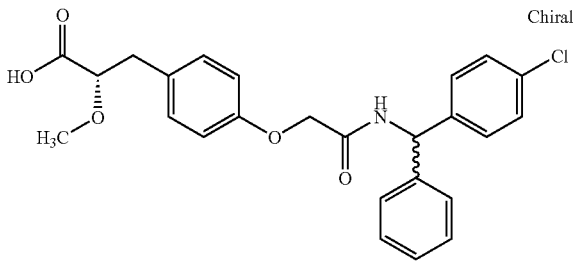

The title compound was prepared from (2S)-3-(4-carboxymethoxy-phenyl)-2-methoxy-propionic acid ethyl ester (PREPARATION 3, step 2) and C-(4-chloro-phenyl)-C-phenyl-methylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a yellow oil. MS (ES) for $C_{25}H_{24}ClNO_5$ [M+H]$^+$: 454.

EXAMPLE 32A (2S)-3-(4-{[butyl-(1-phenyl-ethyl)-carbamoyl]-methoxy}-phenyl)-2-methoxy-propionic acid

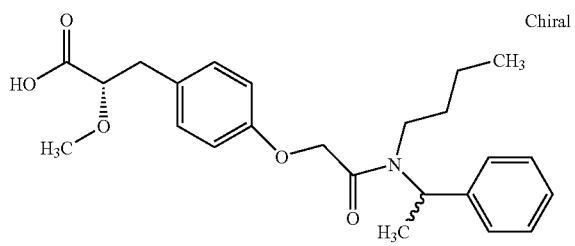

The title compound was prepared from (2S)-3-(4-carboxymethoxy-phenyl)-2-methoxy-propionic acid ethyl ester (PREPARATION 3, step 2) and butyl-(1-phenyl-ethyl)-amine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{24}H_{31}NO_5$ [M+H]$^+$ 414.

EXAMPLE 33

(2S)-3-{4-[(3,3-diphenyl-propylcarbamoyl)-methoxy]-phenyl}-2-methoxy-propionic acid

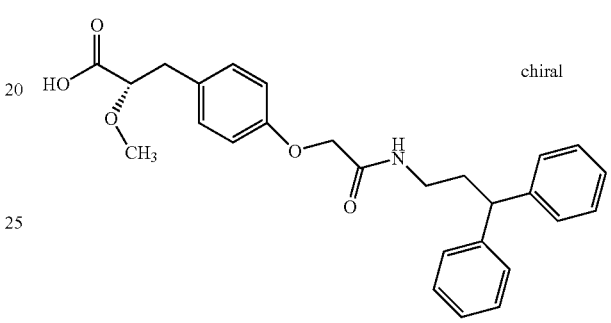

The title compound was prepared from (2S)-3-(4-carboxymethoxy-phenyl)-2-methoxy-propionic acid ethyl ester (PREPARATION 3, step 2) and 3,3-eiphenyl-propylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a yellow oil. MS (ES) for $C_{27}H_{29}NO_5$ [M+H]$^+$: 448.

EXAMPLE 34

(2S)-3-(4-{[benzyl-(2-ethoxycarbonyl-ethyl)-carbamoyl]-methoxy}-phenyl)-2-methoxy-propionic acid

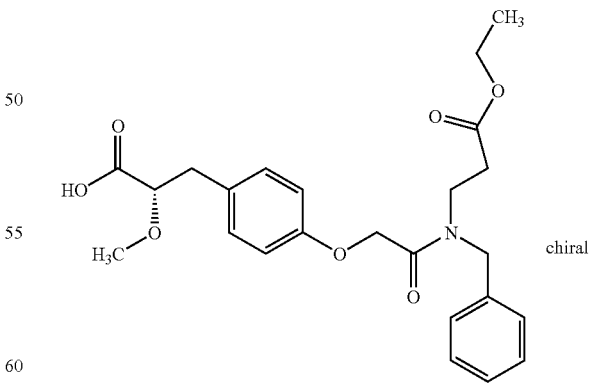

The title compound was prepared from (2S)-3-(4-carboxymethoxy-phenyl)-2-methoxy-propionic acid ethyl ester (PREPARATION 3, step 2) and 3-benzylamino-propionic acid ethyl ester via the same procedure used for the preparation of (2S,1R)-2-ethoxy-3-(4-{1-[2-(4-phenoxy-phenyl)- ethylcarbamoyl]-ethoxy}-phenyl)-propionic acid (Example 1, step 3) to produce a colorless oil. MS (ES) for $C_{24}H_{29}NO_7$ [M+H]$^+$: 444.

EXAMPLE 35

(2S)-2-methoxy-3-(4-{[3-(methyl-phenyl-amino)-propylcarbamoyl]-methoxy}-phenyl)-propionic acid

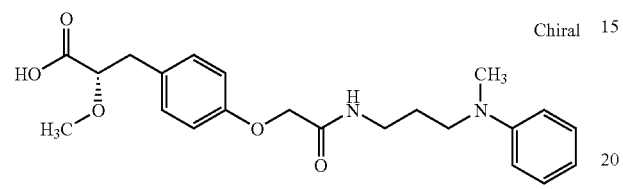

The title compound was prepared from (2S)-3-(4-carboxymethoxy-phenyl)-2-methoxy-propionic acid ethyl ester (PREPARATION 3, step 2) and N1-methyl-N1-phenyl-propane-1,3-diamine via the same procedure used for the preparation of (2S,1R)-2-ethoxy-3-(4-{1-[2-(4-phenoxy-phenyl)-ethylcarbamoyl]-ethoxy}-phenyl)propionic acid (Example 1, step 3) to produce a colorless oil. MS (ES) for $C_{22}H_{28}N_2O_5$ [M+H]$^+$: 401.

EXAMPLE 36

(2S)-2-methoxy-3-(4-{[2-(4-methoxy-phenoxy)-ethylcarbamoyl]-methoxy}-phenyl)-propionic acid

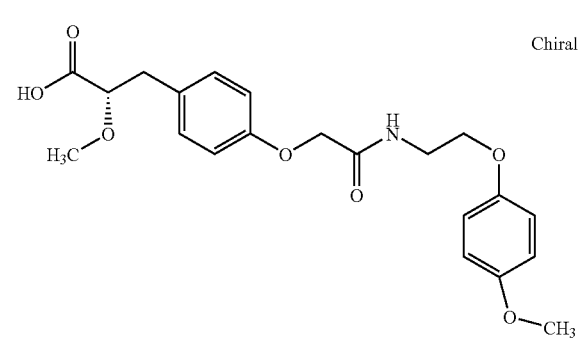

The title compound was prepared from (2S)-3-(4-carboxymethoxy-phenyl)-2-methoxy-propionic acid ethyl ester (PREPARATION 3, step 2) and 2-(4-methoxy-phenoxy)-ethylamine via the same procedure used for the preparation of (2S,1R)-2-ethoxy-3-(4-{1-[2-(4-phenoxy-phenyl)-ethyl-carbamoyl]-ethoxy}-phenyl)-propionic acid (Example 1, step 3) to produce a colorless oil. MS (ES) for $C_{21}H_{25}NO_7$ [M+H]$^+$: 404.

EXAMPLE 37

(2S)-2-methoxy-3-{4-[(4-phenoxy-phenylcarbamoyl)-methoxy]-phenyl}-propionic acid

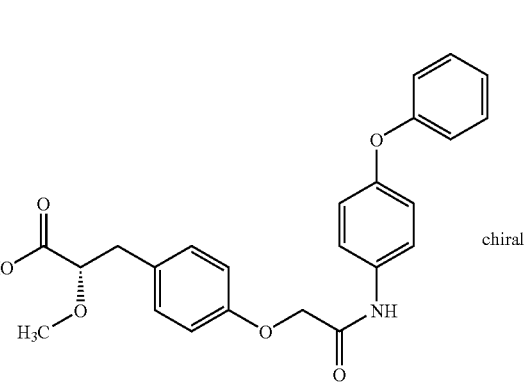

The title compound was prepared from (2S)-3-(4-carboxymethoxy-phenyl)-2-methoxy-propionic acid ethyl ester (PREPARATION 3, step 2) and 4-phenoxy-phenylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{24}H_{23}NO_6$ [M+H]$^+$: 421.

EXAMPLE 38

2-methoxy-3-{3-[(4-phenoxy-phenylcarbamoyl)-methoxy]-phenyl}-propionic acid (isomer 1)

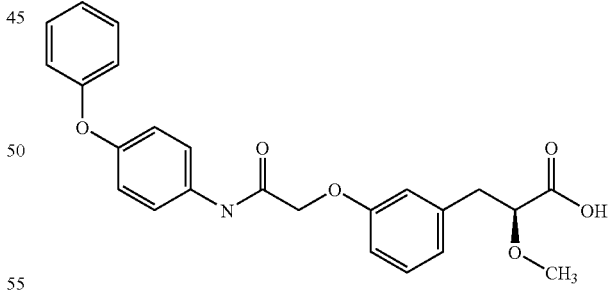

The title compound was prepared from 3-(3-carboxymethoxy-phenyl)-2-methoxy-propionic acid methyl ester (PREPARATION 4, step 2) and 4-phenoxy-phenylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{24}H_{23}NO_6$ [M+H]$^+$: 322.

EXAMPLE 39

(2S)-3-{4-[1-(4-tert-butyl-cyclohexylcarbamoyl)-1-methyl-ethoxy]-phenyl}-2-methoxy-propionic acid

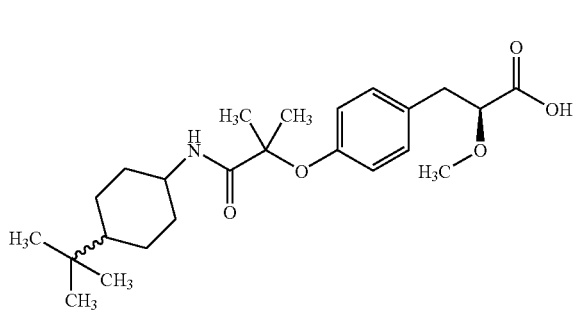

The title compound was prepared from (2S)-3-[4-(1-carboxy-1-methyl-ethoxy)-phenyl]-2-methoxy-propionic acid ethyl ester (PREPARATION 5, step 2) and 4-cis/trans-tert-butyl-cyclohexylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{24}H_{37}NO_5$ [M+H]$^+$: 420.

EXAMPLE 40

(2S)-2-methoxy-3-(4-{1-methyl-1-[2-(4-phenoxy-phenyl)-ethylcarbamoyl]-ethoxy}-phenyl)-propionic acid

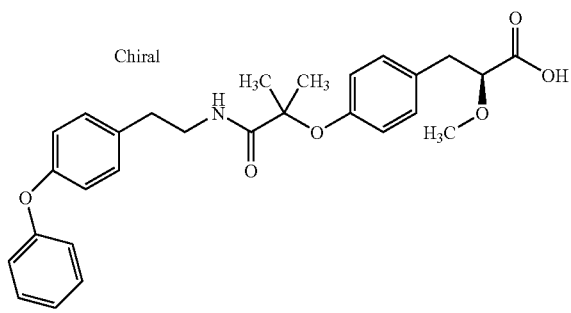

The title compound was prepared from (2S)-3-[4-(1-carboxy-1-methyl-ethoxy)-phenyl]-2-methoxy-propionic acid ethyl ester (PREPARATION 5, step 2) and 4-phenoxy-phenylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{28}H_{31}NO_6$ [M+H]$^+$: 478.

EXAMPLE 41

(2S)-3-(4-{1-[2-(2-ethoxy-phenyl)-ethylcarbamoyl]-1-methyl-ethoxy}-phenyl)-2-methoxy-propionic acid

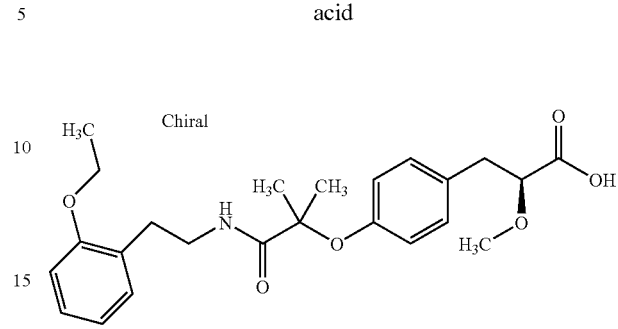

The title compound was prepared from (2S)-3-[4-(1-carboxy-1-methyl-ethoxy)-phenyl]-2-methoxy-propionic acid ethyl ester (PREPARATION 5, step 2) and 2-(2-ethoxy-phenyl)-ethylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{24}H_{31}NO_6$ [M+H]$^+$: 430.

EXAMPLE 42

2-methoxy-2-methyl-3-(4-{[2-(4-phenoxy-phenyl)-ethylcarbamoyl]-methoxy}-phenyl)-propionic acid

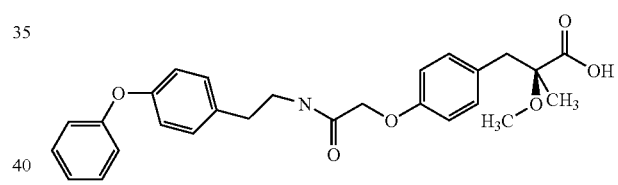

The title compound was prepared from 3-(4-carboxymethoxy-phenyl)-2-methoxy-2-methyl-propionic acid methyl ester 2-(4-phenoxy-phenyl)-ethylamine via the same procedure used for the preparation of (2S,1R)-2-ethoxy-3-(4-{1-[2-(4-phenoxy-phenyl)-ethylcarmoyl]-ethoxy}-phenyl)-propionic acid (Example 1, step 3) to produce a colorless oil. MS (ES) for $C_{27}H_{29}NO_6$ [M+H]$^+$: 464.

EXAMPLE 43

2-methoxy-3-(4-{1-methyl-1-[2-(3-trifluoromethyl-phenyl)-ethylcarbamoyl]-ethoxy}-phenyl)-propionic acid

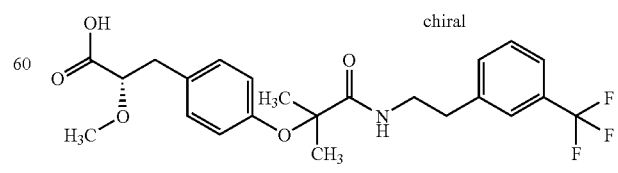

The title compound was prepared from (2S)-3-[4-(1-carboxy-1-methyl-ethoxy)-phenyl]-2-methoxy-propionic acid ethyl ester (PREPARATION 5, step 2) and 2-(3-trifluoromethyl-phenyl)-ethylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{23}H_{26}F_3NO_5$ [M−H]$^-$: 452.

EXAMPLE 44

(2S)-2-methoxy-3-{4-[1-methyl-1-(3-trifluoromethyl-benzylcarbamoyl)-ethoxy]-phenyl}-propionic acid

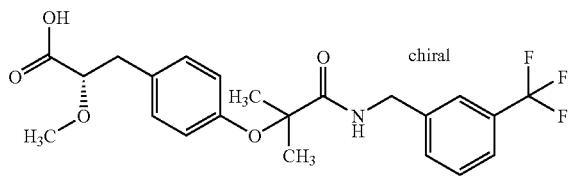

The title compound was prepared from (2S)-3-[4-(1-carboxy-1-methyl-ethoxy)-phenyl]-2-methoxy-propionic acid ethyl ester (PREPARATION 5, step 2) and 3-trifluoromethyl-benzylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{22}H_{24}F_3NO_5$ [M−H]$^-$: 438.

EXAMPLE 45

(2S)-3-(4-{1-[2-(2-chloro-phenyl)-ethylcarbamoyl]-1-methyl-ethoxy}-phenyl)-2-methoxy-propionic acid

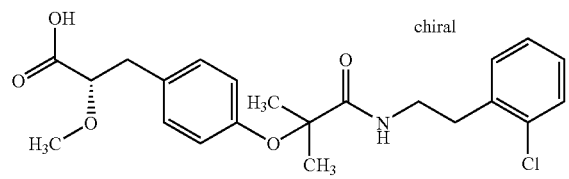

The title compound was prepared from (2S)-3-[4-(1-carboxy-1-methyl-ethoxy)-phenyl]-2-methoxy-propionic acid ethyl ester (PREPARATION 5, step 2) and 2-(2-chloro-phenyl)-ethylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{22}H_{26}ClNO_5$ [M−H]$^-$: 420.

EXAMPLE 46

(2S)-3-(4-{1-[(biphenyl-3-ylmethyl)-carbamoyl]-1-methyl-ethoxy}-phenyl)-2-methoxy-propionic acid

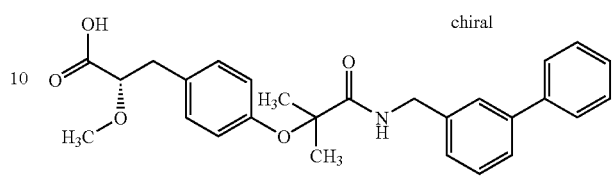

The title compound was prepared from (2S)-3-[4-(1-carboxy-1-methyl-ethoxy)-phenyl]-2-methoxy-propionic acid ethyl ester (PREPARATION 5, step 2) and C-biphenyl-3-yl-methylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{27}H_{29}NO_5$ [M−H]$^-$: 446.

EXAMPLE 47

(2S)-3-(4-{1-[2-(2,5-dimethoxy-phenyl)-ethylcarbamoyl]-1-methyl-ethoxy}-phenyl)-2-methoxy-propionic acid

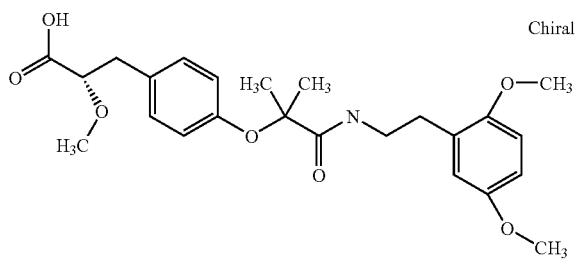

The title compound was prepared from (2S)-3-[4-(1-carboxy-1-methyl-ethoxy)-phenyl]-2-methoxy-propionic acid ethyl ester (PREPARATION 5, step 2) and 2-(2,5-dimethoxy-phenyl)-ethylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{24}H_{31}NO_7$ [M−H]$^-$: 445.

EXAMPLE 48

(2S)-3-(4-{1-[2-(2-fluoro-phenyl)-ethylcarbamoyl]-1-methyl-ethoxy}-phenyl)-2-methoxy-propionic acid

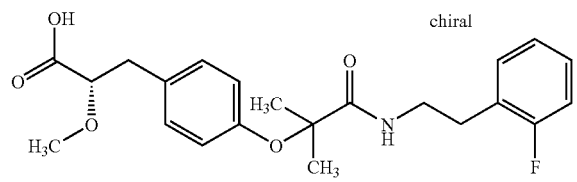

The title compound was prepared from (2S)-3-[4-(1-carboxy-1-methyl-ethoxy)-phenyl]-2-methoxy-propionic acid ethyl ester (PREPARATION 5, step 2) and 2-(2-fluorophenyl)-ethylamine via the same procedure used for the preparation of (2S,1R)-2-ethoxy-3-(4-{1-[2-(4-phenoxyphenyl)-ethylcarbamoyl]-ethoxy}-phenyl)-propionic acid (Example 1, step 3) to produce a colorless oil. MS (ES) for $C_{22}H_{26}FNO_5$ [M−H]$^-$: 402.

EXAMPLE 49

(2S)-2-ethoxy-3-(4-{1-methyl-1-[2-(3-trifluoromethyl-phenyl)-ethylcarbamoyl]-ethoxy}-phenyl)-propionic acid

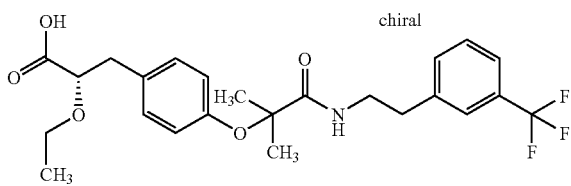

Step 1: (2S)-3-[4-(1-tert-butoxycarbonyl-1-methyl-ethoxy)-phenyl]-2-ethoxy-propionic acid ethyl ester

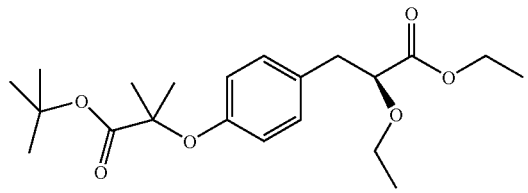

The title compound was prepared (2S)-2-ethoxy-3-(4-hydroxy-phenyl)-propionic acid ethyl ester (example 251, step 3) and 2-bromo-2-methyl-propionic acid tert-butyl ester via the same procedure used to prepare (2S)-3-(4-tert-butoxycarbonylmethoxy-phenyl)-2-methoxy-propionic acid ethyl ester (PREPARATION 3, step 1) to produce a yellow oil.

MS (ES) for $C_{21}H_{32}O_6$ [M+H]$^+$: 381.

Step 2: (2S)-3-[4-(1-carboxy-1-methyl-ethoxy)-phenyl]-2-ethoxy-propionic acid ethyl ester

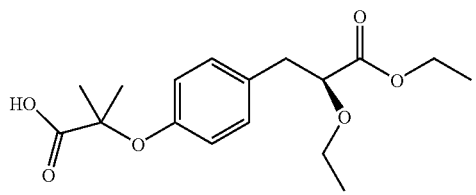

The title compound was prepared from (2S)-3-[4-(1-tert-butoxycarbonyl-1-methyl-ethoxy)-phenyl]-2-ethoxy-propionic acid ethyl ester (EXAMPLE 49, step 1) via the same procedure used to prepare (2S)-3-(4-carboxymethoxy-phenyl)-2-methoxy-propionic acid ethyl ester (PREPARATION 3, step 2) to produce a yellow oil.

MS (ES) for $C_{17}H_{24}O_6$ [M+H]$^+$: 325.

Step 3: (2S)-2-ethoxy-3-(4-{1-methyl-1-[2-(3-trifluoromethyl-phenyl)-ethylcarbamoyl]-ethoxy}-phenyl)-propionic acid

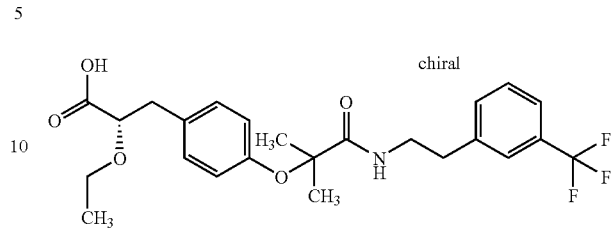

The title compound was prepared from (2S)-3-[4-(1-carboxy-1-methyl-ethoxy)-phenyl]-2-ethoxy-propionic acid ethyl ester (EXAMPLE 49, step 2) and 2-(4-trifluoromethyl-phenyl)-ethylamine via the same procedure used for the preparation of (2S,1R)-2-ethoxy-3-(4-{1-[2-(4-phenoxyphenyl)-ethylcarbamoyl]-ethoxy}-phenyl)-propionic acid (Example 1, step 3) to produce a colorless oil. MS (ES) for $C_{24}H_{28}F_3NO_5$ [M−H]$^-$: 466.

EXAMPLE 50

(2S)-2-ethoxy-3-{4-[1-(3-fluoro-5-trifluoromethyl-benzylcarbamoyl)-1-methyl-ethoxy]-phenyl}-propionic acid

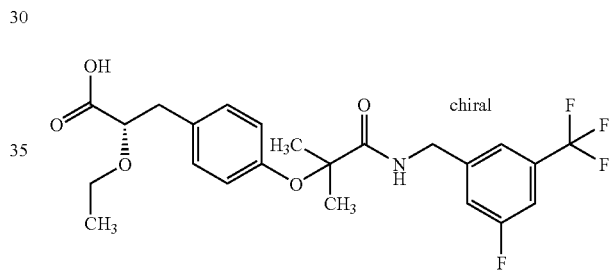

The title compound was prepared from (2S)-3-[4-(1-carboxy-1-methyl-ethoxy)-phenyl]-2-ethoxy-propionic acid ethyl ester (EXAMPLE 49, step 2) and 3-fluoro-5-trifluoromethyl-benzylamine via the same procedure used for the preparation of (2S,1R)-2-ethoxy-3-(4-{1-[2-(4-phenoxyphenyl)-ethylcarbamoyl]-ethoxy}-phenyl)-propionic acid (Example 1, step 3) to produce a colorless oil. MS (ES) for $C_{23}H_{25}F_4NO_5$ [M−H]$^-$: 470.

EXAMPLE 51

(2S)-3-(4-{1-[2-(2-chloro-phenyl)-ethylcarbamoyl]-1-methyl-ethoxy}-phenyl)-2-ethoxy-propionic acid

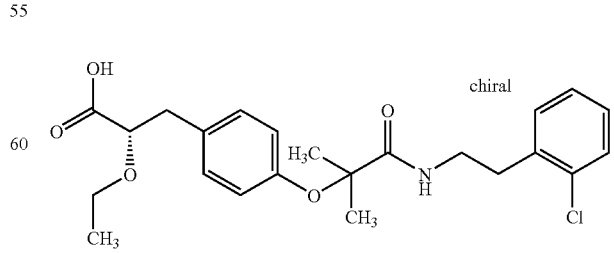

The title compound was prepared from (2S)-3-[4-(1-varboxy-1-methyl-ethoxy)-phenyl]-2-ethoxy-propionic acid ethyl ester (EXAMPLE 49, step 2) and 2-(2-chloro-phenyl)-ethylamine via the same procedure used for the preparation of (2S,1R)-2-ethoxy-3-(4-{1-[2-(4-phenoxy-phenyl)-ethyl-carbamoyl]-ethoxy}-phenyl)-propionic acid (Example 1, step 3) to produce a colorless oil. MS (ES) for $C_{23}H_{28}Cl_4NO_5$ [M–H]$^-$: 434.

EXAMPLE 52

(2S)-3-(4-{1-[(biphenyl-3-ylmethyl)-carbamoyl]-1-methyl-ethoxy}-phenyl)-2-ethoxy-propionic acid

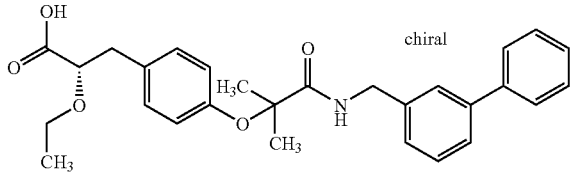

The title compound was prepared from (2S)-3-[4-(1-carboxy-1-methyl-ethoxy)-phenyl]-2-ethoxy-propionic acid ethyl ester (EXAMPLE 49, step 2) and C-biphenyl-3-yl-methylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{28}H_{31}NO_5$ [M–H]$^-$: 462.

EXAMPLE 53

(2S)-3-(4-{1-[2-(3-chloro-phenyl)-ethylcarbamoyl]-1-methyl-ethoxy}-phenyl)-2-ethoxy-propionic acid

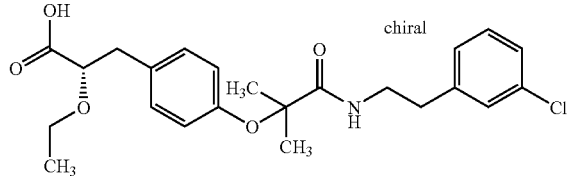

The title compound was prepared from (2S)-3-[4-(1-carboxy-1-methyl-ethoxy)-phenyl]-2-ethoxy-propionic acid ethyl ester (EXAMPLE 49, step 2) and 2-(3-chloro-phenyl)-ethylamine via the same procedure used for the preparation of (2S,1R)-2-ethoxy-3-(4-{1-[2-(4-phenoxy-phenyl)-ethyl-carbamoyl]-ethoxy}-phenyl)-propionic acid (Example 1, step 3) to produce a colorless oil. MS (ES) for $C_{23}H_{28}ClNO_5$ [M–H]$^-$: 434.

EXAMPLE 54

(2S)-3-(4-{1-[2-(2,5-dimethoxy-phenyl)-ethylcar-bamoyl]-methyl-ethoxy}-phenyl)-2-ethoxy-propionic acid

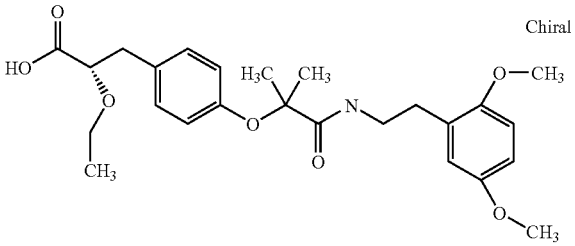

The title compound was prepared from (2S)-3-[4-(1-carboxy-1-methyl-ethoxy)-phenyl]-2-ethoxy-propionic acid ethyl ester (EXAMPLE 49, step 2) and 2-(2,5-dimethoxy-phenyl)-ethylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{25}H_{33}NO_7$ [M–H]$^-$: 458.

EXAMPLE 55

(2S)-2-ethoxy-3-(4-{1-[2-(2-fluoro-phenyl)-ethylcar-bamoyl]-1-methyl-ethoxy}-phenyl)-propionic acid

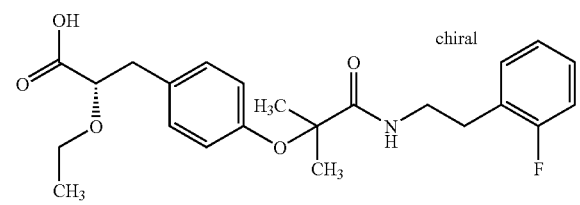

The title compound was prepared from (2S)-3-[4-(1-carboxy-1-methyl-ethoxy)-phenyl]-2-ethoxy-propionic acid ethyl ester (EXAMPLE 49, step 2) and 2-(2-fluoro-phenyl)-ethylamine via the same procedure used for the preparation of (2S,1R)-2-ethoxy-3-(4-{1-[2-(4-phenoxy-phenyl)-ethyl-carbamoyl]-ethoxy}-phenyl)-propionic acid (Example 1, step 3) to produce a colorless oil. MS (ES) for $C_{23}H_{28}FNO_5$ [M–H]$^-$: 416.

EXAMPLE 56

(2S)-3-{3-[1-(4-tert-butyl-cyclohexylcarbamoyl)-1-methyl-ethoxy]-phenyl}-2-methoxy-propionic acid

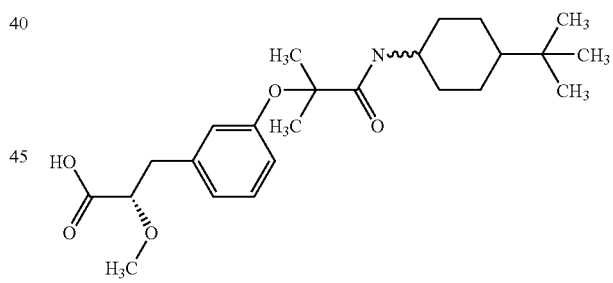

Step 1: (2S)-3-[3-(1-tert-butoxycarbonyl-1-methyl-ethoxy)-phenyl]-2-methoxy-propionic acid methyl ester

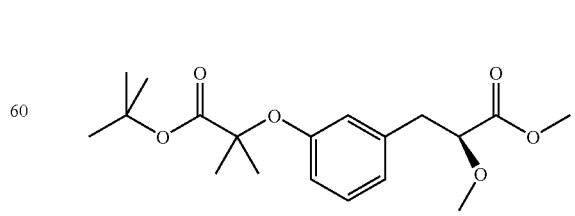

The title compound was prepared from 3-(3-hydroxy-phenyl)-2-methoxy-propionic acid methyl ester (example 9, step 4) and 2-bromo-2-methyl-propionic acid tert-butyl ester via the same procedure used for the preparation of (2S)-3-(4-tert-butoxycarbonyl-methoxy-phenyl)-2-methoxy-propionic acid ethyl ester (PREPARATION 3, step 1) to produce a yellow oil. $^1$H-NMR (CDCl$_3$, 200.15 MHz): δ 7.13-7.09 (m, 1H), 6.84-6.69 (m, 3H), 3.95-3.89 (dd, 1H, J=6.5, 4.4), 3.7 (s, 3H), 3.34 (s, 3H), 2.94-2.90 (m, 2H), 1.50 (s, 6H), 1.43 (s, 9H).

Step 2: (2S)-3-[3-(1-carboxy-1-methyl-ethoxy)-phenyl]-2-methoxy-propionic acid methyl ester

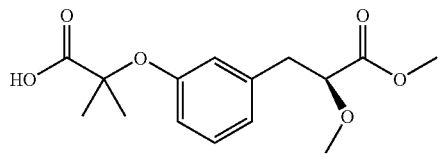

The title compound was prepared from 3-[3-(1-tert-butoxycarbonyl-1-methyl-ethoxy)-phenyl]-2-methoxy-propionic acid methyl ester (EXAMPLE 56, step 1) via the same procedure used to produce (2S)-3-(4-carboxymethoxy-phenyl)-2-methoxy-propionic acid ethyl ester (PREPARATION 3, step 2) to produce a yellow oil. $^1$H-NMR (CDCl3, 200.15 MHz): δ 7.19-7.15 (m, 1H), 6.96-6.79 (m, 3H), 3.96-3.89 (dd, 1H, J=6.5, 4.4), 3.70 (s, 3H), 3.33 (s, 3H), 2.98-2.94 (m, 2H), 1.55 (s, 6H).

Step 3: (2S)-3-{3-[1-(4-tert-butyl-cyclohexylcarbamoyl)-1-methyl-ethoxy]-phenyl}-2-methoxy-propionic acid

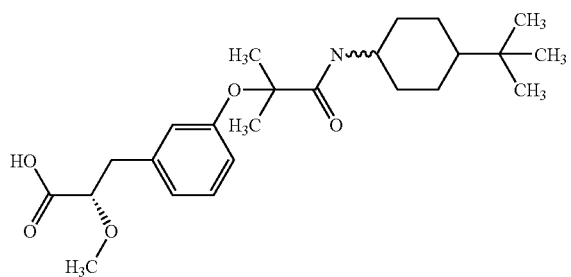

The title compound was prepared from (2S)-3-[3-(1-carboxy-1-methyl-ethoxy)-phenyl]-2-methoxy-propionic acid methyl ester (EXAMPLE 56, step 2) and 4-tert-cis/trans-Butyl-cyclohexylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for C$_{24}$H$_{37}$NO$_5$ [M–H]$^-$: 418.

EXAMPLE 57

(2S)-3-(3-{1-[2-(4-ethyl-phenyl)-ethylcarbamoyl]-1-methyl-ethoxy}-phenyl)-2-methoxy-propionic acid

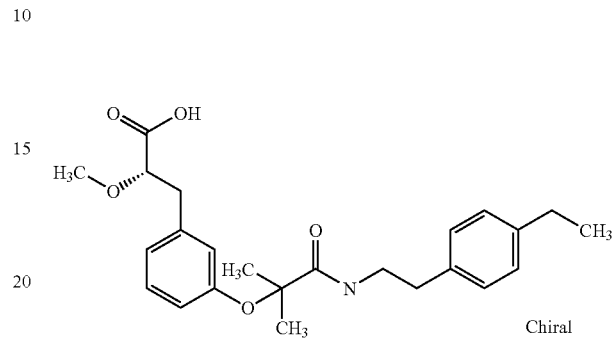

The title compound was prepared from (2S)-3-[3-(1-carboxy-1-methyl-ethoxy)-phenyl]-2-methoxy-propionic acid methyl ester (EXAMPLE 56, step 2) and 2-(4-ethyl-phenyl)-ethylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for C$_{24}$H$_{31}$NO$_5$ [M–H]$^-$: 412.

EXAMPLE 58

(2S)-2-methoxy-3-(3-{1-methyl-1-[2-(4-phenoxy-phenyl)-ethylcarbamoyl]-ethoxy}-phenyl)-propionic acid

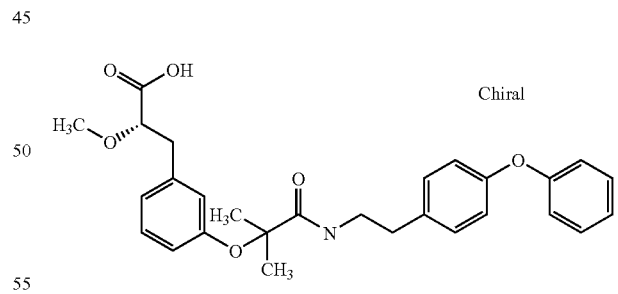

The title compound was prepared from (2S)-3-[3-(1-carboxy-1-methyl-ethoxy)-phenyl]-2-methoxy-propionic acid methyl ester (EXAMPLE 56, step 2) and 4-phenoxy-phenyl amine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for C$_{28}$H$_{31}$NO$_6$ [M–H]$^-$: 476.

EXAMPLE 59

(2S)-3-{3-[1-(3-fluoro-5-trifluoromethyl-benzylcarbamoyl)-1-methyl-ethoxy]-phenyl}-2-methoxy-propionic acid

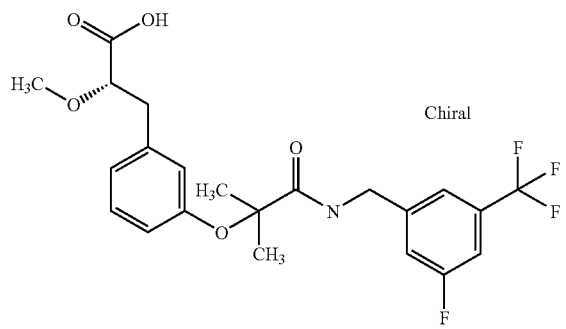

The title compound was prepared from (2S)-3-[3-(1-carboxy-1-methyl-ethoxy)-phenyl]-2-methoxy-propionic acid methyl ester (EXAMPLE 56, step 2) and 3-fluoro-5-trifluoromethyl-benzylamine amine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{22}H_{23}F_4NO_5$ [M−H]−: 456.

EXAMPLE 60

(2S)-3-(3-{1-[(biphenyl-3-ylmethyl)-carbamoyl]-1-methyl-ethoxy}-phenyl)-2-methoxy-propionic acid

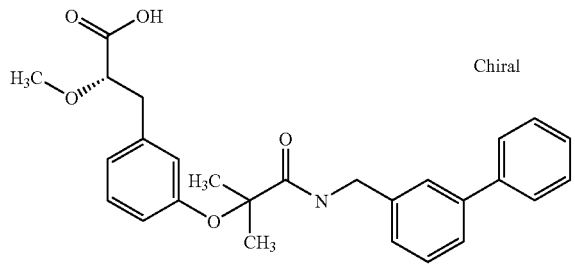

The title compound was prepared from (2S)-3-[3-(1-carboxy-1-methyl-ethoxy)-phenyl]-2-methoxy-propionic acid methyl ester (EXAMPLE 56, step 2) and C-biphenyl-3-yl-methylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{27}H_{28}NO_5$ [M−H]−: 446.

EXAMPLE 61

(2S)-3-(3-{1-[2-(3-chloro-phenyl)-ethylcarbamoyl]-1-methyl-ethoxy}-phenyl)-2-methoxy-propionic acid

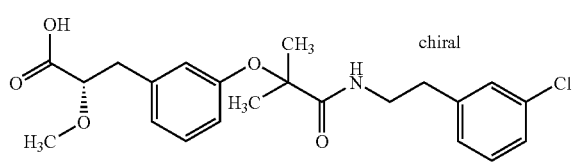

The title compound was prepared from (2S)-3-[3-(1-carboxy-1-methyl-ethoxy)-phenyl]-2-methoxy-propionic acid methyl ester (EXAMPLE 56, step 2) and 2-(3-chlorophenyl)-ethylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{22}H_{29}ClNO_5$ [M−H]−: 418.

EXAMPLE 62

(2S)-2-methoxy-3-{4-[(1-phenyl-ethylcarbamoyl)-methoxy]-phenyl}-propionic acid

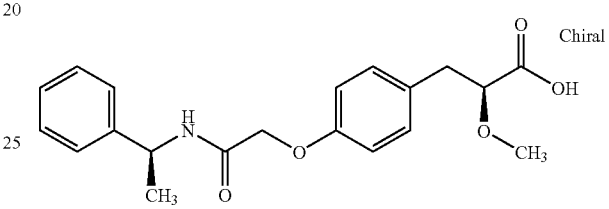

The title compound was prepared from (2S)-3-(4-carboxymethoxy-phenyl)-2-methoxy-propionic acid ethyl ester (PREPARATION 3, step 2) and 1-phenyl-ethylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a yellow oil. MS (ES) For $C_{20}H_{23}NO_5$ [M+H]+: 358.

EXAMPLE 63

(2S)-3-(3-{1-[2-(2,4-dichloro-phenyl)-ethylcarbamoyl]-1-methyl-ethoxy}-phenyl)-2-methoxy-propionic acid

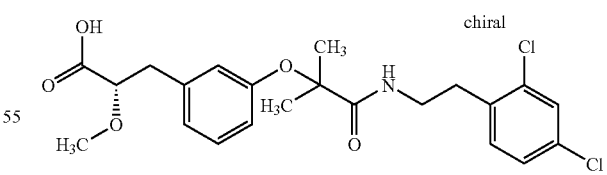

The title compound was prepared from (2S)-3-[3-(1-carboxy-1-methyl-ethoxy)-phenyl]-2-methoxy-propionic acid methyl ester (EXAMPLE 56, step 2) and 2-(2,4-dichloro-phenyl)-ethylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil.
MS (ES) for $C_{22}H_{25}ClNO_5$ [M]+: 454, [M+2]+: 456.

EXAMPLE 64

(2S)-3-(3-{1-[2-(2,6-dichloro-phenyl)-ethylcarbamoyl]-1-methyl-ethoxy}-phenyl)-2-methoxy-propionic acid

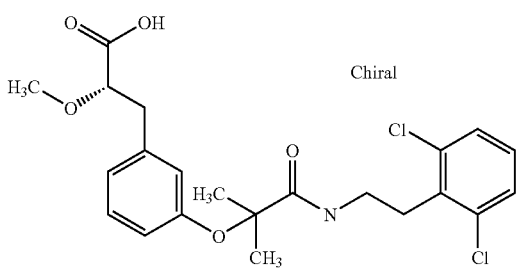

The title compound was prepared from (2S)-3-[3-(1-carboxy-1-methyl-ethoxy)-phenyl]-2-methoxy-propionic acid methyl ester (EXAMPLE 56, step 2) and 2-(2,6-dichloro-phenyl)-ethylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{22}H_{25}ClNO_5$ [M]+: 454, [M+2]+: 456.

EXAMPLE 65

(2S)-3-[3-(1-heptylcarbamoyl-1-methyl-ethoxy)-phenyl]-2-methoxy-propionic acid

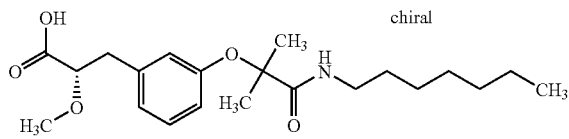

The title compound was prepared from (2S)-3-[3-(1-carboxy-1-methyl-ethoxy)-phenyl]-2-methoxy-propionic acid methyl ester (EXAMPLE 56, step 2) and heptylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{21}H_{33}NO_5$ [M+H]+: 480.

EXAMPLE 66

(2S)-3-(4-{1-[2-(2,4-dichloro-phenyl)-ethylcarbamoyl]-1-methyl-ethoxy}-phenyl)-2-methoxy-propionic acid

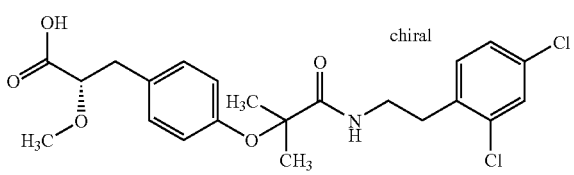

The title compound was prepared from (2S)-3-[4-(1-carboxy-1-methyl-ethoxy)-phenyl]-2-methoxy-propionic acid ethyl ester (PREPARATION 5, step 2) and 2-(2,4-dichloro-phenyl)-ethylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{22}H_{25}Cl_2NO_5$ [M−H]−: 452, [M+H]: 454.

EXAMPLE 67

(2S)-3-(4-{1-[2-(2,4-dichloro-phenyl)-ethylcarbamoyl]-1-methyl-ethoxy}-phenyl)-2-ethoxy-propionic acid

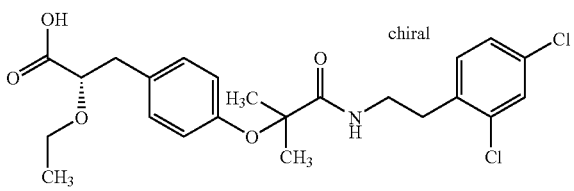

The title compound was prepared from (2S)-3-[4-(1-carboxy-1-methyl-ethoxy)-phenyl]-2-methoxy-propionic acid ethyl ester (PREPARATION 5, step 2) and 2-(2,4-dichloro-phenyl)-ethylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{22}H_{25}Cl_2NO_5$ [M−H]−: 452, [M+H]−: 454.

EXAMPLE 68

(2S)-3-(4-{1-[2-(2,6-dichloro-phenyl)-ethylcarbamoyl]-1-methyl-ethoxy}-phenyl)-2-ethoxy-propionic acid

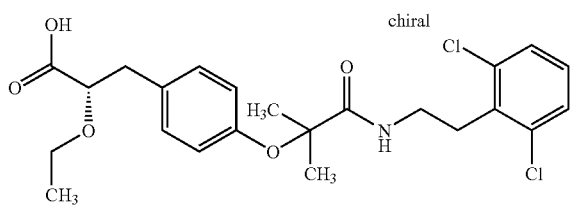

The title compound was prepared from (2S)-3-[4-(1-carboxy-1-methyl-ethoxy)-phenyl]-2-ethoxy-propionic acid ethyl ester (EXAMPLE 49, step 2) and 2-(2,6-dichloro-phenyl)-ethylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{23}H_{27}Cl_2NO_5$ [M−H]−: 466, [M+H]−: 468.

EXAMPLE 69

(2S)-2-ethoxy-3-(4-{1-[2-(4-ethyl-phenyl)-ethylcarbamoyl]-1-methyl-ethoxy}-phenyl)-propionic acid

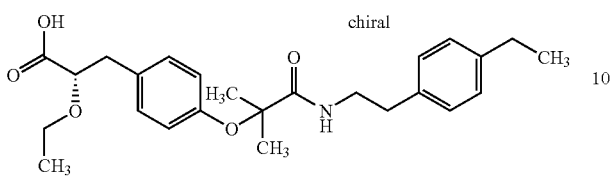

The title compound was prepared from (2S)-3-[4-(1-carboxy-1-methyl-ethoxy)-phenyl]-2-ethoxy-propionic acid ethyl ester (EXAMPLE 49, step 2) and 2-(4-ethyl-phenyl)ethylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{25}H_{33}NO_5$ $[M+H]^+$: 428.

EXAMPLE 70

(2S)-2-ethoxy-3-(4-{1-[2-(2-ethoxy-phenyl)-ethylcarbamoyl]-1-methyl-ethoxy}-phenyl)-propionic acid

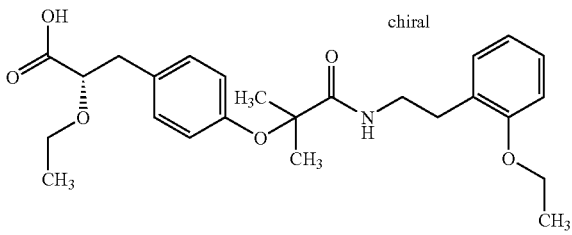

The title compound was prepared from (2S)-3-[4-(1-carboxy-1-methyl-ethoxy)-phenyl]-2-ethoxy-propionic acid ethyl ester (EXAMPLE 49, step 2) and 2-(2-ethoxy-phenyl)-ethylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{25}H_{33}NO_6$ $[M+H]^+$: 444.

EXAMPLE 71

(2S)-2-ethoxy-3-[4-(1-heptylcarbamoyl-1-methyl-ethoxy)-phenyl]-propionic acid

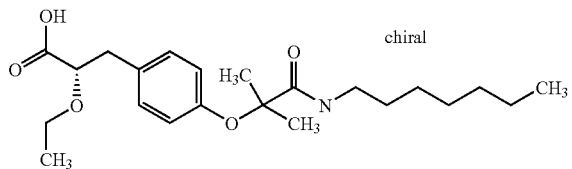

The title compound was prepared from (2S)-3-[4-(1-carboxy-1-methyl-ethoxy)-phenyl]-2-ethoxy-propionic acid ethyl ester (EXAMPLE 49, step 2) and hepthylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{22}H_{33}NO_5$ $[M+H]^+$: 394.

Preparation 6

(R,S)-3-[4-(1-Benzyoxycarbonyl-ethoxy)-phenyl]-2-ethoxy-priopionic acid ethyl ester

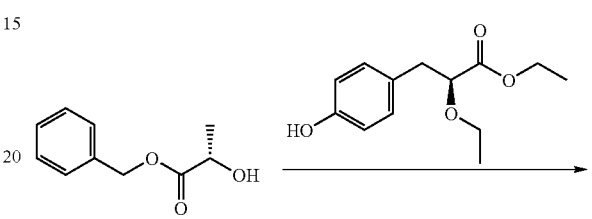

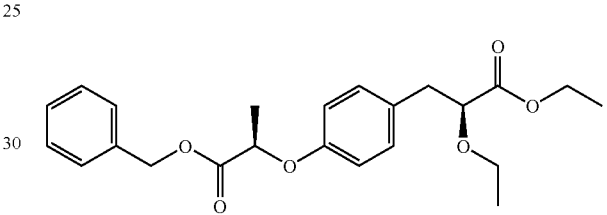

To a solution of 2-(S)-hydroxypropionic acid benzyl ester (0.966 g, 5.36 mmol) and (S)-2-ethoxy-3-(4-hydroxy-phenyl)-propionic acid ethyl ester (1.16 g, 4.88 mmol) in THF (30 ml) was added the triphenyl phosphine (1.66 g, 6.34 mmol). The mixture was cooled to 0° C. and added the DIAD (diisopropyl azodicarboxylate) (1.18 g, 5.86 mmol) dropwise over 5 minutes. The reaction mixture was stirred for 18 hours while warmed to room temperature. The reaction was quenched with water (2 ml) and concentrated to a residue, purified by silica gel chromatography with 20% EtOAc/Hexanes to afford product (1.05 g, 49%) and recovered starting material ((S)-2-ethoxy-3-(4-hydroxy-phenyl)-propionic acid ethyl ester, 0.31 g).

Preparation 7

(R,S)-3-[4-(1-Carboxy-ethoxy)-phenyl]-2-ethoxy-propionic acid ethyl ester

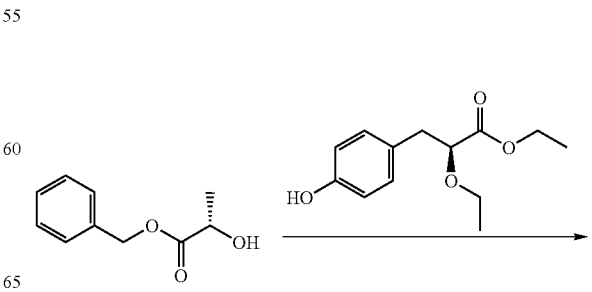

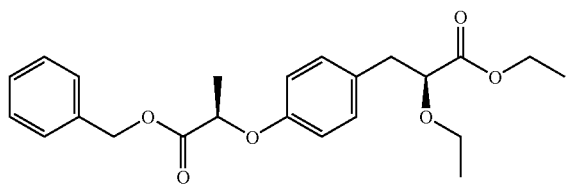

To a solution of (R,S)-3-[4-(1-benzyloxycarbonyl-ethoxy)-phenyl]-2-ethoxy-propionic acid ethyl ester (1.05 g, 2.63 mmol) in EtOH (20 ml) and H₂O (0.5 ml) was added a slurry of Pd—C (5%, 100 mg) in EtOH (10 ml). The suspension was hydrogenated under balloon pressure for 2 hours. The mixture was filtered through a pad of celite and concentrated to a residue, the residue was then purified by silica gel chromatography with EtOAc/Hexanes (25% to 100%) to afford the acid product (550 mg, 68%).

Preparation 8

(R,S)-3-(4-{1-[2-(3-Chloro-phenyl)-ethylcarbamoyl]-ethoxy}-phenyl)-2-ethoxy-propionic acid

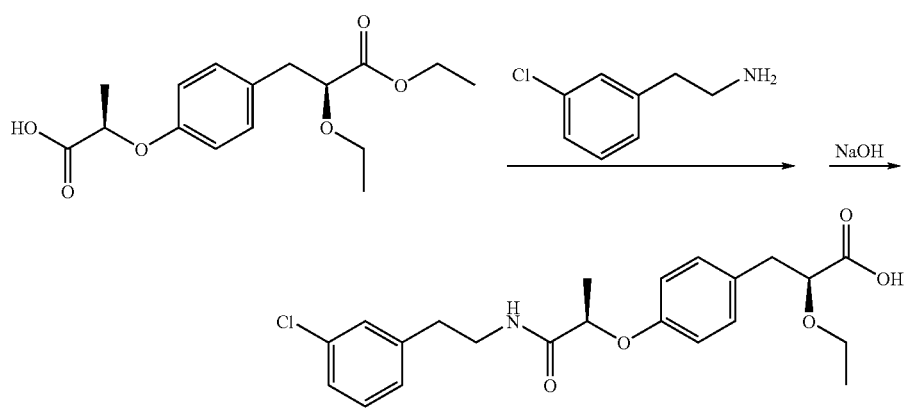

A solution of (R,S)-3-[4-(1-carboxy-ethoxy)-phenyl]-2-ethoxy-propionic acid ethyl ester (310 mg, 1.00 mmol) in CH₂Cl₂ (35 ml) was treated with DMAP (207 mg, 1.70 mmol) and EDC (286 mg, 1.50 mmol). The mixture was stirred at room temperature for 10 minutes and then treated with 3-chlorophenyl ethylamine (201 mg, 1.3 mmol). The reaction mixture was stirred for 2 hours and quenched with NH₄Cl (aq), extracted with CH₂Cl₂ (2×35 ml) and dried over Na₂SO₄, purified on silica gel column with EtOAc/Hexanes (20-35%) to yield the intermediate ester product (291 mg, 65%).

The ethyl ester was then dissolved in methanol (2.0 ml) and THF (1.0 ml), and the solution was treated with NaOH (2.0 N, 3.0 ml). The reaction mixture was stirred at room temperature for 18 hours and neutralized with HCl (1.0 N, 6.0 ml) to pH=7 and concentrated. Extracted with EtOAc (3×20 ml), dried over Na₂SO₄, purified on silica gel column with EtOAc/Hexanes (35%-100%) and MeOH/EtOAc (5%) to yield the final acid product (130 mg, 29% for two steps).

Preparation 9

(S,S)-3-[4-(1-tert-Butoxycarbonyl-ethoxy)-phenyl]-2-ethoxy-propionic acid ethyl ester

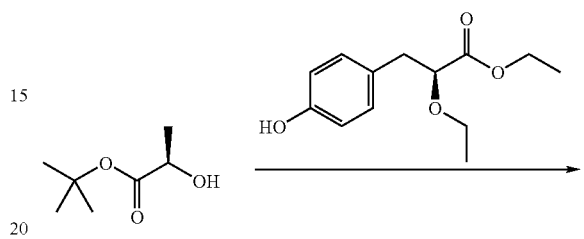

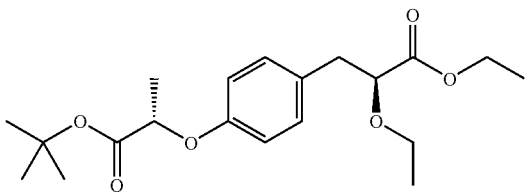

To a solution of 2-(R)-hydroxypropionic acid tert-butyl ester (1.23 g, 8.44 mmol) and (S)-2-ethoxy-3-(4-hydroxyphenyl)-propionic acid ethyl ester (2.01 g, 8.44 mmol) in THF (100 ml) was added the triphenyl phosphine (2.21 g, 8.44 mmol). The mixture was cooled to 0° C. and added the DIAD (diisopropyl azodicarboxylate) (1.70 g, 8.44 mmol) dropwise over 5 minutes. The reaction mixture was stirred for 18 hours while warmed to room temperature. The reaction was quenched with water (2 ml) and concentrated to a residue, purified by silica gel chromatography with 20% EtOAc/Hexanes to afford product (0.99 g, 32%) and recovered starting material ((S)-2-ethoxy-3-(4-hydroxy-phenyl)-propionic acid ethyl ester, 0.85 g).

Preparation 10

(S,S)-3-[4-(1-Carboxy-ethoxy)-phenyl]-2-ethoxy-propionic acid ethyl ester

EXAMPLE 74A (S,S)-3-(4-{1-[2-(2-Chloro-phenyl)-ethylcarbamoyl]-ethoxy}-phenyl)-2-ethoxy-propionic acid

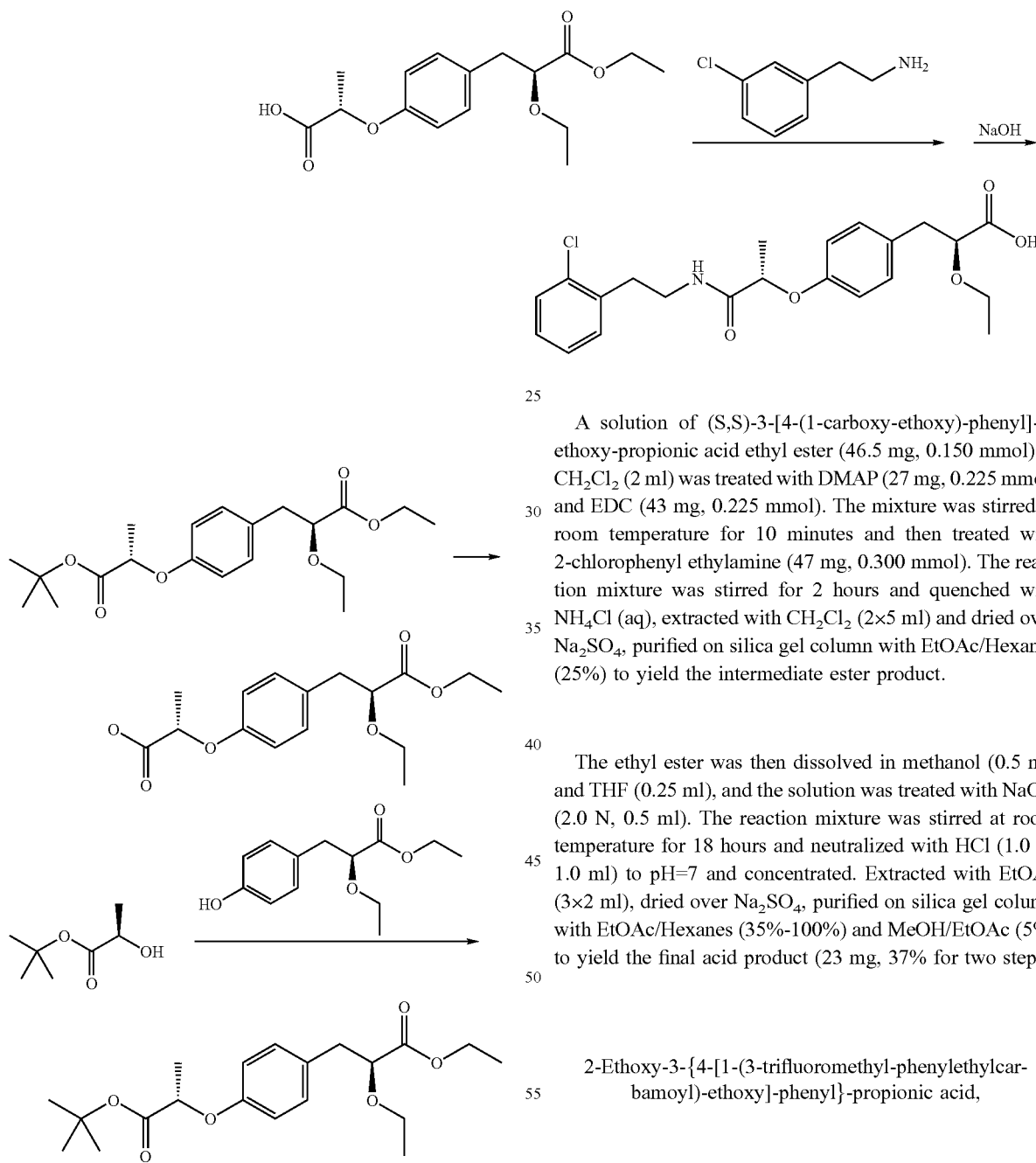

A solution of (S,S)-3-[4-(1-carboxy-ethoxy)-phenyl]-2-ethoxy-propionic acid ethyl ester (46.5 mg, 0.150 mmol) in CH$_2$Cl$_2$ (2 ml) was treated with DMAP (27 mg, 0.225 mmol) and EDC (43 mg, 0.225 mmol). The mixture was stirred at room temperature for 10 minutes and then treated with 2-chlorophenyl ethylamine (47 mg, 0.300 mmol). The reaction mixture was stirred for 2 hours and quenched with NH$_4$Cl (aq), extracted with CH$_2$Cl$_2$ (2×5 ml) and dried over Na$_2$SO$_4$, purified on silica gel column with EtOAc/Hexanes (25%) to yield the intermediate ester product.

The ethyl ester was then dissolved in methanol (0.5 ml) and THF (0.25 ml), and the solution was treated with NaOH (2.0 N, 0.5 ml). The reaction mixture was stirred at room temperature for 18 hours and neutralized with HCl (1.0 N, 1.0 ml) to pH=7 and concentrated. Extracted with EtOAc (3×2 ml), dried over Na$_2$SO$_4$, purified on silica gel column with EtOAc/Hexanes (35%-100%) and MeOH/EtOAc (5%) to yield the final acid product (23 mg, 37% for two steps).

A solution of (S,S)-3-[4-(1-tert-butoxycarbonyl-ethoxy)-phenyl]-2-ethoxy-propionic acid ethyl ester (1.10 g, 3.00 mmol) in CH$_2$Cl$_2$ (5.0 ml) and TFA (4.0 ml) and water (0.2 ml) was stirred for 12 hours. The mixture was concentrated to a residue and purified by silica gel chromatography with EtOAc/Hexanes (50%) to afford the acid product (0.91 g, 98%).

2-Ethoxy-3-{4-[1-(3-trifluoromethyl-phenylethylcarbamoyl)-ethoxy]-phenyl}-propionic acid, $^1$H NMR (400 MHz, CDCl$_3$): δ 1.07 (br s, 3H), 1.46 (d, 3H, J=6.8 Hz), 2.80-3.01 (m, 4H), 3.28-3.32 (m, 1H), 3.48-3.58 (m, 3H), 3.88 (br s, 1H), 4.58 (q, 1H, J=6.4 Hz), 6.57-6.71 (m, 1H), 6.73 (d, 2H, J=7.8 Hz), 6.98-7.18 (m, 5H), 7.28 (d, 1H, J=7.8 Hz).

MS (MH+): 420.2

EXAMPLE 75

2-Ethoxy-3-[4-(1-hexylcarbamoyl-ethoxy)-phenyl]-propionic acid

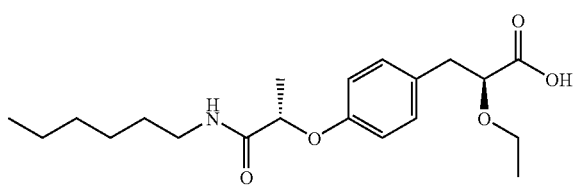

The title compound was prepared using same method for (S,S)-3-(4-{1-[2-(2-Chloro-phenyl)-ethylcarbamoyl]-ethoxy}-phenyl)-2-ethoxy-propionic acid. $^1$HNMR (400 MHz, CDCl$_3$): δ 0.84 (t, 3H, J=6.8 Hz), 1.17 (t, 3H, J=6.7 Hz), 1.22-1.27 (m, 8H), 1.44 (t, 2H, J=6.8 Hz), 1.54 (d, 3H, J=6.8 Hz), 2.93-2.98 (dd, 1H, J=7.3 Hz, 13.7 Hz), 3.04-3.08 (dd, 1H, J=4.2 Hz, 14.3 Hz), 3.41-3.46 (m, 1H), 3.58-3.64 (m, 1H), 4.03 (dd, 1H, J=4.4 Hz, 7.8 Hz), 4.64 (q, 1H, J=6.8 Hz), 6.46 (t, 1H, J=5.4 Hz), 6.82 (d, 2H, J=8.3 Hz), 7.18 (d, 2H, J=8.8 Hz),

MS (MH+): 366.2

EXAMPLE 76

3-{4-[1-(4-tert-Butyl-cyclohexylcarbamoyl)-ethoxy]-phenyl}-2-ethoxy-propionic acid

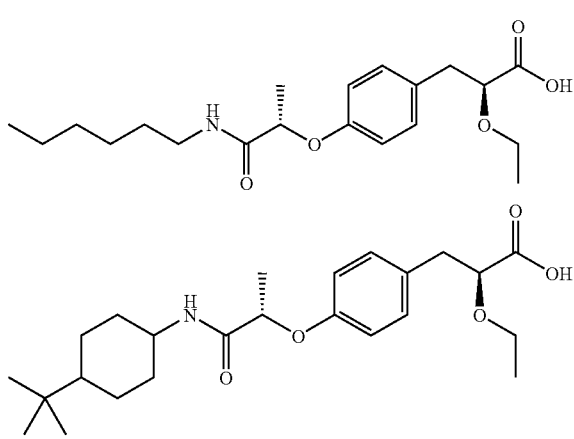

The title compound was prepared using same method for (S,S)-3-(4-{1-[2-(2-Chloro-phenyl)-ethylcarbamoyl]-ethoxy}-phenyl)-2-ethoxy-propionic acid. $^1$H NMR (400 MHz, CDCl$_3$, major isomer): δ 0.81 (s, 9H), 0.88-0.98 (m, 3H), 1.05-1.17 (m, 6H), 1.51 (d, 3H, J=6.8 Hz), 1.70-1.88 (m, 3H), 1.98-2.01 (m, 1H), 2.84-2.90 (dd, 1H, J=7.3 Hz, 13.7 Hz), 2.99-3.04 (dd, 1H, J=4.2 Hz, 14.3 Hz), 3.31 (br s, 1H), 3.54-3.57 (m, 1H), 3.64-3.72 (m, 1H), 3.95 (br s, 1H), 4.60 (q, 1H, J=6.8 Hz), 6.27 (d, 1H, J=8.3 Hz), 6.82 (d, 2H, J=8.3 Hz), 7.18 (d, 2H, J=7.8 Hz),

MS (MH+): 420.3

EXAMPLE 77

2-Ethoxy-3-{4-[1-(3-trifluoromethyl-benzylcarbamoyl)-ethoxy]-phenyl}-propionic acid

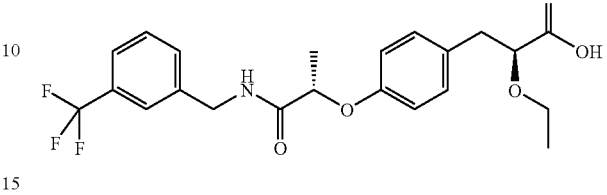

The title compound was prepared using same method for (S,S)-3-(4-{1-[2-(2-Chloro-phenyl)-ethylcarbamoyl]-ethoxy}-phenyl)-2-ethoxy-propionic acid. $^1$H NMR (400 MHz, CDCl$_3$): δ 1.07 (t, 3H, J=6.7 Hz), 1.52 (d, 3H, J=6.8 Hz), 2.82-2.89 (dd, 1H, J=7.3 Hz, 13.7 Hz), 2.95-3.02 (dd, 1H, J=4.2 Hz, 14.3 Hz), 3.27-3.30 (m, 1H), 3.50-3.54 (m, 1H), 3.92 (dd, 1H, J=4.4 Hz, 7.8 Hz), 4.47 (d, 2H, J=5.9 Hz), 4.64 (q, 2H, J=7.3 Hz), 6.76 (d, 2H, J=7.3 Hz), 6.06-7.14 (m, 3H), 7.32-7.46 (m, 4H); MS (MH+): 440.2.

EXAMPLE 78

2-Ethoxy-3-{4-[1-(5-fluoro-3-trifluoromethyl-benzylcarbamoyl)-ethoxy]-phenyl}-propionic acid

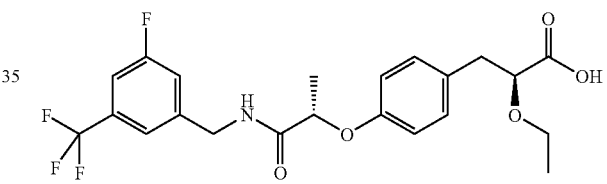

The title compound was prepared using same method for (S,S)-3-(4-{1-[2-(2-Chloro-phenyl)-ethylcarbamoyl]-ethoxy}-phenyl)-2-ethoxy-propionic acid. $^1$H NMR (400 MHz, CDCl$_3$): δ 1.07 (t, 3H, J=6.7 Hz), 1.53 (d, 3H, J=6.8 Hz), 2.82-2.89 (dd, 1H, J=7.3 Hz, 13.7 Hz), 2.95-3.02 (dd, 1H, J=4.2 Hz, 14.3 Hz), 3.27-3.35 (m, 1H), 3.53-3.58 (m, 1H), 3.93 (dd, 1H, J=4.4 Hz, 7.8 Hz), 4.40-4.50 (m, 2H), 4.62 (q, 1H, J=6.8 Hz), 6.76 (d, 2H, J=7.3 Hz), 7.00 (d, 1H, J=8.8 Hz), 7.13-7.20 (m, 5H); MS (MH+): 486.1.

EXAMPLE 79

2-Ethoxy-3-{4-[1-(3-phenyl-benzylcarbamoyl)-ethoxy]-phenyl}-propionic acid

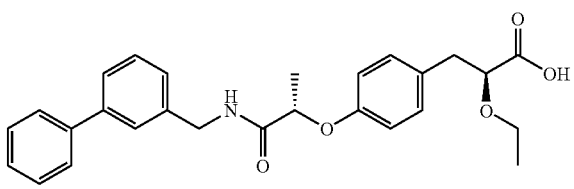

The title compound was prepared using same method for (S,S)-3-(4-{1-[2-(2-Chloro-phenyl)-ethylcarbamoyl]- ethoxy}-phenyl)-2-ethoxy-propionic acid. ¹H NMR (400 MHz, CDCl₃): δ 1.02 (t, 3H, J=6.7 Hz), 1.52 (d, 3H, J=6.8 Hz), 2.78-2.84 (dd, 1H, J=7.3 Hz, 13.7 Hz), 2.95-3.02 (dd, 1H, J=4.2 Hz, 14.3 Hz), 3.22-3.27 (m, 1H), 3.48-3.52 (m, 1H), 3.89 (dd, 1H, J=4.4 Hz, 7.8 Hz), 4.40-4.50 (m, 3H), 6.75 (d, 2H, J=7.3 Hz), 7.00 (br s, 1H), 7.10 (d, 2H, J=7.8 Hz), 7.28-7.49 (m, 9H); MS (MH+): 448.2.

EXAMPLE 80

2-Ethoxy-3-{4-[1-(4-phenoxy-phenylethylcarbamoyl)-ethoxy]-phenyl}-propionic acid

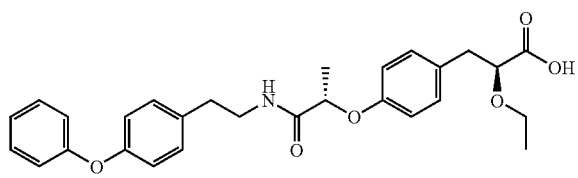

The title compound was prepared using same method for (S,S)-3-(4-{1-[2-(2-Chloro-phenyl)-ethylcarbamoyl]-ethoxy}-phenyl)-2-ethoxy-propionic acid. ¹H NMR (400 MHz, CDCl₃): δ 1.16 (t, 3H, J=6.7 Hz), 1.52 (d, 3H, J=6.8 Hz), 2.65-2.71 (dd, 1H, J=6.9 Hz, 13.7 Hz), 2.74-2.80 (dd, 1H, J=6.3 Hz, 12.7 Hz), 2.96-2.99 (m, 1H), 3.04-3.08 (m, 1H), 3.40-3.44 (m, 2H), 3.56-3.64 (m, 2H), 4.03 (br s, 1H), 4.60 (q, 1H, J=6.4 Hz), 6.48 (br s, 1H), 6.76 (d, 2H, J=7.8 Hz), 6.85-6.88 (m, 2H), 6.96-7.00 (m, 4H), 7.07-7.17 (m, 3H), 7.30-7.35 (m, 2H); MS (MH+): 506.2.

EXAMPLE 81

2-Ethoxy-3-{4-[1-(3-trifluoromethyl-phenylethylcarbamoyl)-ethoxy]-phenyl}-propionic acid

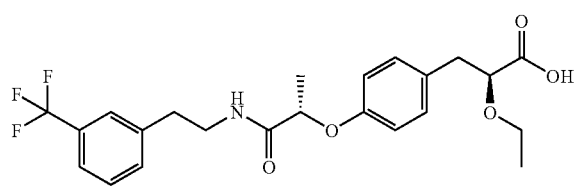

The title compound was prepared using same method for (S,S)-3-(4-{1-[2-(2-Chloro-phenyl)-ethylcarbamoyl]-ethoxy}-phenyl)-2-ethoxy-propionic acid. ¹H NMR (400 MHz, CDCl₃): δ 1.00 (br s, 3H), 1.43 (d, 3H, J=6.8 Hz), 2.73-2.88 (m, 3H), 2.96-3.00 (m, 1H), 3.21-3.26 (m, 1H), 3.46-3.52 (m, 3H), 3.88 (br s, 1H), 4.60 (q, 1H, J=6.4 Hz), 6.63-6.69 (m, 3H), 7.10 (d, 1H, J=7.8 Hz), 7.20 (d, 1H, J=7.8 Hz), 7.29-7.36 (m, 2H), 7.42 (d, 1H, J=7.8 Hz); MS (MH+): 454.2.

EXAMPLE 82

3-(4-{1-[2-(2,6-Dichloro-phenyl)-ethylcarbamoyl]-ethoxy}-phenyl)-2-ethoxy-propionic acid

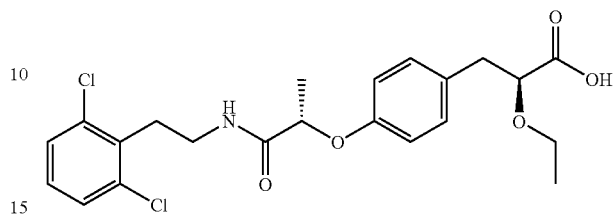

The title compound was prepared using same method for (S,S)-3-(4-{1-[2-(2-Chloro-phenyl)-ethylcarbamoyl]-ethoxy}-phenyl)-2-ethoxy-propionic acid. ¹H NMR (400 MHz, CDCl₃): δ 1.05 (t, 3H, J=6.4 Hz), 1.45 (d, 3H, J=6.8 Hz), 2.80-2.86 (dd, 1H, J=6.9 Hz, 13.7 Hz), 2.97-3.01 (d, 1H, J=13.2 Hz), 3.10-3.18 (m, 2H), 3.22-3.30 (m, 1H), 3.46-3.62 (m, 3H), 3.92 (br s, 1H), 4.56 (q, 1H, J=6.4 Hz), 6.71-6.77 (m, 3H), 7.05 (t, 1H, J=7.8 Hz), 7.12 (d, 2H, J=7.8 Hz), 7.22 (d, 2H, J=7.8 Hz); MS (MH+): 454.1

EXAMPLE 83

2-Ethoxy-3-(4-{1-[2-(4-ethyl-phenyl)-ethylcarbamoyl]-ethoxy}-phenyl)-propionic acid

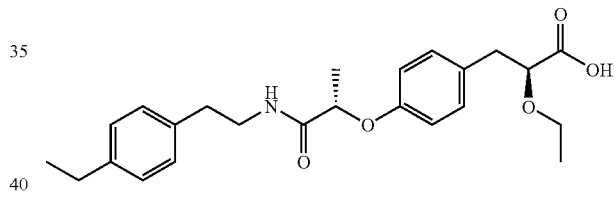

The title compound was prepared using same method for (S,S)-3-(4-{1-[2-(2-Chloro-phenyl)-ethylcarbamoyl]-ethoxy}-phenyl)-2-ethoxy-propionic acid. ¹H NMR (400 MHz, CDCl₃): δ 1.16 (t, 3H, J=6.8 Hz), 1.21 (t, 3H, J=7.6 Hz), 1.49 (d, 3H, J=6.4 Hz), 2.60 (q, 2H, J=6.8 Hz), 2.60-2.68 (m, 1H), 2.73-2.80 (m, 1H), 2.94-3.00 (dd, 1H, J=7.8 Hz, 14.2 Hz), 3.04-3.09 (dd, 1H, J=4.3 Hz, 14.2 Hz), 3.40-3.46 (m, 2H), 3.52-3.65 (m, 2H), 4.03 (dd, 1H, J=4.3 Hz, 7.8 Hz), 4.62 (q, 1H, J=6.8 Hz), 6.52 (t, 1H, J=6.4 Hz), 6.76 (d, 2H, J=8.8 Hz), 6.95 (d, 2H, J=7.8 Hz), 7.06 (d, 2H, J=7.8 Hz), 7.18 (d, 2H, J=8.3 Hz); MS (MH+): 414.2.

EXAMPLE 84

2-Ethoxy-3-(4-{1-[2-(4-ethyl-phenyl)-ethylcarbamoyl]-ethoxy}-phenyl)-propionic acid

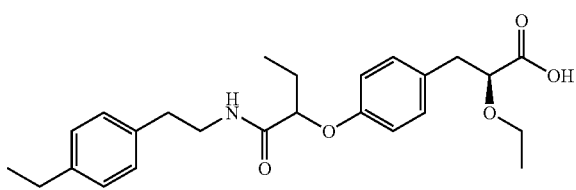

The title compound was prepared using same method for (S,S)-3-(4-{1-[2-(2-Chloro-phenyl)-ethylcarbamoyl]-ethoxy}-phenyl)-2-ethoxy-propionic acid. $^1$H NMR (400 MHz, CDCl$_3$): δ 0.97 (t, 3H, J=7.8 Hz), 1.19 (t, 3H, J=7.6 Hz), 1.21 (t, 3H, J=6.8 Hz), 1.80-1.90 (m, 1H), 1.90-1.98 (m, 1H), 2.60 (q, 2H, J=7.3 Hz), 2.60-2.68 (m, 1H), 2.72-2.79 (m, 1H), 2.99 (dd, 1H, J=7.3 Hz, 14.2 Hz), 3.08 (dd, 1H, J=3.9 Hz, 12.7 Hz), 3.40-3.48 (m, 2H), 3.52-3.64 (m, 2H), 4.02-4.07 (m, 1H), 4.48 (dd, 1H, J=4.8 Hz, 6.8 Hz), 6.54 (t, 1H, J=6.4 Hz), 6.60 (d, 2H, J=8.8 Hz), 6.87 (d, 2H, J=8.3 Hz), 6.96 (d, 2H, J=7.8 Hz), 7.02 (d, 2H, J=8.3 Hz); MS (MH+): 428.2.

EXAMPLE 85

2-Ethoxy-3-(4-{1-[2-(4-ethyl-phenyl)-ethylcarbamoyl]-propoxy}-phenyl)-propionic acid

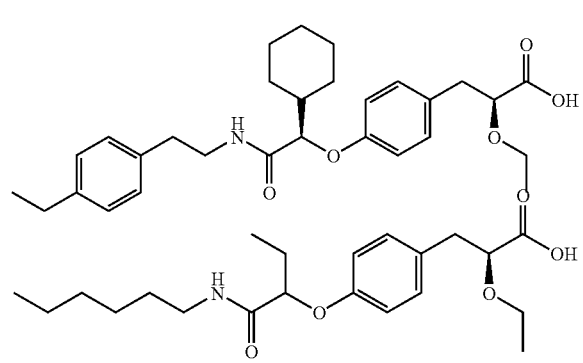

The title compound was prepared using same method for (S,S)-3-(4-{1-[2-(2-Chloro-phenyl)-ethylcarbamoyl]-ethoxy}-phenyl)-2-ethoxy-propionic acid. $^1$H NMR (400 MHz, CDCl$_3$): δ 0.80 (t, 3H, J=6.8 Hz), 1.03 (t, 3H, J=7.6 Hz), 1.10-1.20 (m, 11H), 2.85-2.89 (m, 1H), 2.91 (dd, 1H, J=7.3 Hz, 14.2 Hz), 2.98 (dd, 1H, J=4.8 Hz, 14.2 Hz), 2.96-3.01 (m, 1H), 3.37-3.43 (m, 2H), 3.50-3.57 (m, 2H), 3.99 (dd, 1H, J=4.4 Hz, 7.3 Hz), 4.52 (t, 1H, J=6.4 Hz), 6.54 (t, 1H, J=6.4 Hz), 6.68 (d, 2H, J=8.3 Hz), 7.02 (d, 2H, J=8.3 Hz); MS (MH+): 380.2

EXAMPLE 86

2-Ethoxy-3-(4-{1-[2-(4-phenoxy-phenyl)-ethylcarbamoyl]-propoxy}-phenyl)-propionic acid

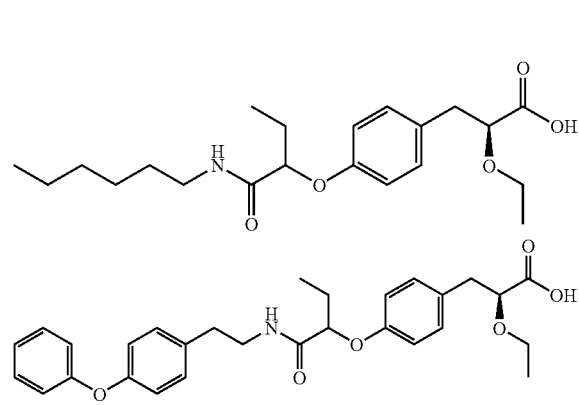

The title compound was prepared using same method for (S,S)-3-(4-{1-[2-(2-Chloro-phenyl)-ethylcarbamoyl]-ethoxy}-phenyl)-2-ethoxy-propionic acid. $^1$H NMR (400 MHz, CDCl$_3$, one diastereomer): δ 0.92 (t, 3H, J=7.3 Hz), 1.10 (t, 3H, J=6.8 Hz), 1.74-1.82 (m, 1H), 1.86-1.891 (m, 1H), 2.56-2.62 (m, 1H), 2.64-2.71 (m, 1H), 2.86 (dd, 1H, J=7.3 Hz, 14.2 Hz), 2.98 (dd, 1H, J=4.4 Hz, 14.2 Hz), 3.33-3.40 (m, 2H), 3.49-3.57 (m, 2H), 3.95-3.99 (m, 1H), 4.41 (dd, 1H, J=4.4 Hz, 6.8 Hz), 6.40 (t, 1H, J=6.4 Hz), 6.70 (d, 2H, J=8.3 Hz), 6.78 (d, 2H, J=8.8 Hz), 6.88-6.94 (m, 4H), 7.01-7.06 (m, 1H), 7.08 (d, 2H, J=8.8 Hz), 7.25(d, 1H, J=7.4 Hz), 7.27 (d, 1H, J=7.8 Hz); MS (MH+): 492.1.

EXAMPLE 87

3-(4-{Cyclohexyl-[2-(4-ethyl-phenyl)-ethylcarbamoyl]-methoxy}-phenyl)-2-ethoxy-propionic acid

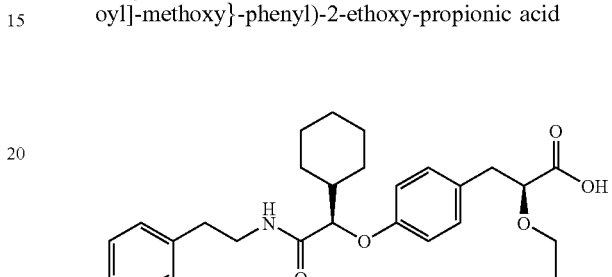

The title compound was prepared using same method for (S,S)-3-(4-{1-[2-(2-Chloro-phenyl)-ethylcarbamoyl]-ethoxy}-phenyl)-2-ethoxy-propionic acid. $^1$H NMR (400 MHz, CDCl$_3$): δ 1.16 (t, 3H, J=7.8 Hz), 1.20 (t, 3H, J=7.6 Hz), 1.20-1.30 (m, 6H), 1.49 (d, 3H, J=6.8 Hz), 2.08 (s, 2H), 2.60 (q, 2H, J=7.3 Hz), 2.64-2.69 (m, 1H), 2.72-2.80 (m, 1H), 2.97 (dd, 1H, J=6.4 Hz, 14.2 Hz), 3.08 (dd, 1H, J=4.4 Hz, 4.4 Hz), 3.38-3.48 (m, 2H), 3.52-3.66 (m, 2H), 3.80-3.90 (m, 1H), 4.02 (dd, 1H, J=4.4 Hz, 7.8 Hz), 4.62 (q, 1H, J=6.9 Hz), 4.93-5.02 (m, 1H), 6.53 (t, 1H, J=5.9 Hz), 6.76 (d, 2H, J=8.8 Hz), 6.95 (d, 2H, J=8.3 Hz), 7.07 (d, 2H, J=7.8 Hz), 7.17(d, 2H, J=8.3 Hz); MS (MH+): 483.2.

EXAMPLE 88

2-Ethoxy-3-(4-{1-[2-(4-ethyl-phenyl)-ethylcarbamoyl]-2-phenyl-ethoxy}-phenyl)-propionic acid

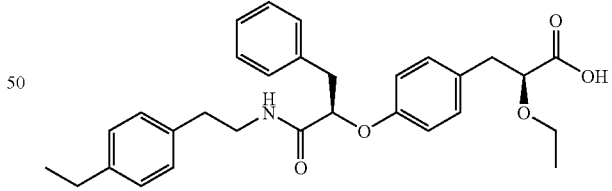

The title compound was prepared using same method for (S,S)-3-(4-{1-[2-(2-Chloro-phenyl)-ethylcarbamoyl]-ethoxy}-phenyl)-2-ethoxy-propionic acid. $^1$H NMR (400 MHz, CDCl$_3$): δ 1.16 (t, 3H, J=7.8 Hz), 1.21 (t, 3H, J=7.3 Hz), 2.55-2.65 (m, 4H), 2.96 (dd, 1H, J=8.3 Hz, 14.2 Hz), 3.04 (dd, 1H, J=3.9 Hz, 14.2 Hz), 3.12 (dd, 1H, J=6.8 Hz, 14.2 Hz), 3.24 (dd, 1H, J=3.4 Hz, 14.2 Hz), 3.39-3.45 (m, 3H), 3.59-3.65 (m, 1H), 4.02 (dd, 1H, J=4.4 Hz, 7.8 Hz), 4.62 (q, 1H, J=3.4 Hz), 6.40 (t, 1H, J=5.8 Hz), 6.69 (d, 2H, J=8.8 Hz), 6.86 (d, 2H, J=7.8 Hz), 7.04 (d, 2H, J=8.3 Hz), 7.13 (d, 2H, J=8.8 Hz), 7.20-7.30 (m, 5H); MS (M+H): 491.4.

Preparation 11

2-Bromo-N-[2-(4-phenoxy-phenyl)-ethyl]-acetamide

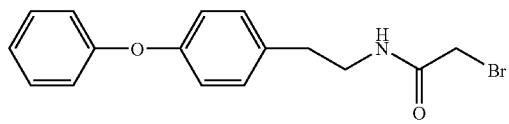

4-phenoxyphenethylamine (213.28 amu, 2.5 g, 1 eq, 10.8 mmol, 1.09 g/mL, 2.3 mL) added to a 3-necked flask. Bromoacetyl bromide (201.86 amu, 1.1 eq, 11.8 mmol, 2.4 g, 2.317 g/mL, 1.03 mL), pyridine (79.10 amu, 5 eq, 4.27 g, 0.978 g/mL, 54 mmol, 4.4 mL) added along with 50 mL CH$_2$Cl$_2$. Reaction stirred for 2 hours at RT. CH$_2$Cl$_2$ removed and mixture taken up in 200 mL EtOAc. Organic layer washed with brine and water (200 mL each). Organics seperated, dried sodium sulfate, and rotovaped to give 1.56 g material. MS [EI+] 334 (M+H)$^+$, MS [EI−] 332 (M−H)$^+$

EXAMPLE 90

2-Methyl-2-phenoxy-3-(4-{[2-(4-phenoxy-phenyl)-ethylcarbamoyl]-methoxy}-phenyl)-propionic acid 3-(4-Hydroxy-phenyl)-2-methyl-2-phenoxy-propionic acid ethyl ester (300.352 amu, 1 eq, 225 mg, 0.76 mmol) added to a 3-necked flask. 20 mL dry dioxane added along with sodium hydride (24 amu, 1.1 eq, 0.82 mmol, 20 mg, 33 mg of 60% dispersion in mineral oil). Mixture stirred at RT for 15 minutes. 2-Bromo-N-[2-(4-phenoxy-phenyl)-ethyl]-acetamide (333.1 amu, 250 mg, 1 eq, 0.76 mmol) added and reaction stirred for 6 hours at 100 deg C. Reaction mixture added to 200 mL EtOAc. Washed with brine and water (twice each, 200 mL). Organics dried sodium sulfate and concentrated to give 250 mg of crude material. Material seperated on chromatatron (10-70% EtOAc/hexanes). Product spot isolated and concentrated to give 25 mg of desired ethyl ester. Material dissolved in 5 mL EtOH. Added to a carousel tube along with 5 mL 5N NaOH. Stirred overnight at 50° C. under nitrogen. Reaction mixture added to 100 mL EtOAc. Acidified with 10 mL concentrated HCl. 100 mL brine added and organic layer removed. Concentrated to give 20 mL product. MS [EI+] 526 (M+H)$^+$, MS [EI−] 524 (M−H)$^+$

EXAMPLE 91

2-Phenoxy-2-(4-{[2-(4-phenoxy-phenyl)-ethylcarbamoyl]-methoxy}-benzyl)-butyric acid

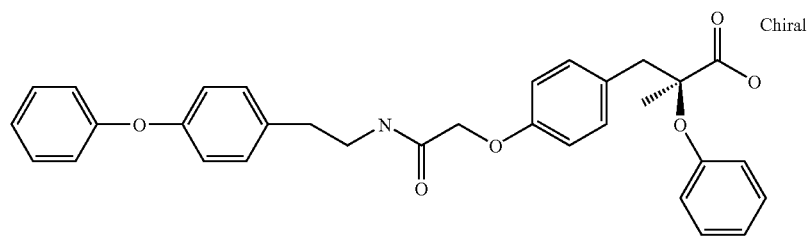

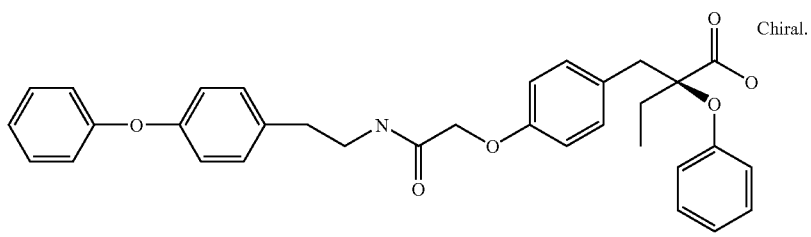

The title compound was prepared using same method for 2-Methyl-2-phenoxy-3-(4-{[2-(4-phenoxy-phenyl)-ethylcarbamoyl]-methoxy}-phenyl)-propionic acid from 2-(4-Hydroxy-benzyl)-2-phenoxy-butyric acid ethyl ester

MS [EI+] 540 (M+H)+, MS [EI−] 538 (M−H)+

EXAMPLE 92

2-Methyl-3-(4-{[2-(4-phenoxy-phenyl)-ethylcarbamoyl]-methoxy}-phenyl)-2-(4-trifluoromethoxy-phenoxy)-propionic acid

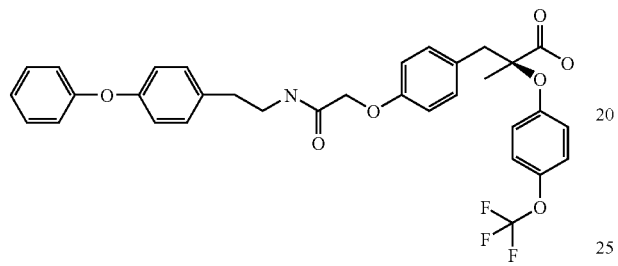

The title compound was prepared using same method for 2-Methyl-2-phenoxy-3-(4-{[2-(4-phenoxy-phenyl)-ethylcarbamoyl]-methoxy}-phenyl)-propionic acid from 3-(4-Hydroxy-phenyl)-2-methyl-2-(4-trifluoromethoxy-phenoxy)-propionic acid ethyl ester.

MS [EI+] 610 (M+H)+, MS [EI−] 608 (M−H)+

EXAMPLE 93

2-(4-Fluoro-phenoxy)-2-methyl-3-(4-{[2-(4-phenoxy-phenyl)-ethylcarbamoyl]-methoxy}-phenyl)-propionic acid

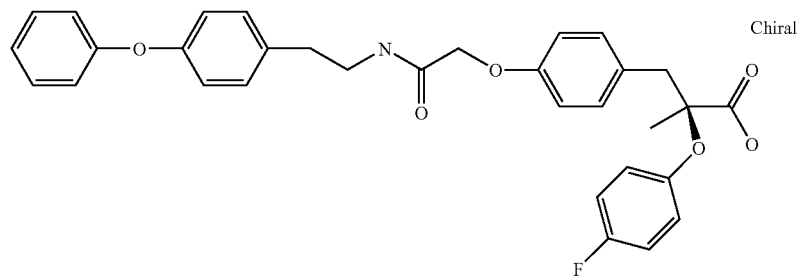

The title compound was prepared using same method for 2-Methyl-2-phenoxy-3-(4-{[2-(4-phenoxy-phenyl)-ethylcarbamoyl]-methoxy}-phenyl)-propionic acid from 2-(4-Fluoro-phenoxy)-3-(4-hydroxy-phenyl)-2-methyl-propionic acid ethyl ester.

MS [EI+] 544 (M+H)+, MS [EI−] 542 (M−H)+

EXAMPLE 94

(2S)-2-methoxy-3-(4-{2-oxo-2-[4-(4-trifluoromethyl-phenyl)-piperazin-1-yl]-ethoxy}-phenyl)-propionic acid

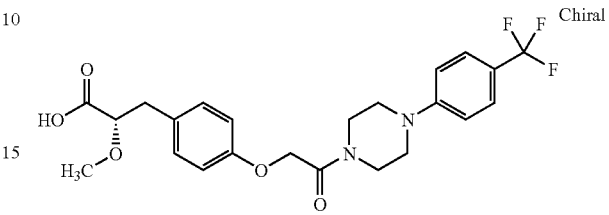

Step 1: (2S)-3-(4-tert-butoxycarbonylmethoxy-phenyl)-2-methoxy-propionic acid ethyl ester

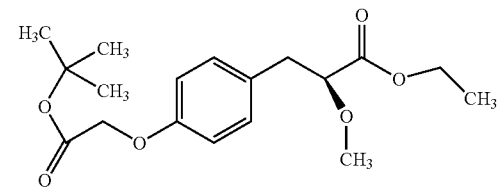

The compound of (2S)-3-(4-hydroxy-phenyl)-2-methoxy-propionic acid ester (Preparation 1), (1.2 g, 5.3 mmol) was dissolved in 25 ml of anhydrous THF and NaH (380 mg, 15.8 mmol) was added portion wise. After about 5 minutes, bromo-acetic acid tert-butyl ester was added dropwise at room temperature. The mixture was stirred for 2 hours at room temperature. The crude was dissolved in ethyl acetate (100 ml) and a solution of 5% HCl was added. The mixture was extracted with ethyl acetate (3×100 ml), and the combined organic layers were dried over (MgSO$_4$) and then concentrated under vacuum. The crude was purified by column chromatography (silica gel, hexane/ethyl acetate 8.5:1,5) to afford a yellow oil.-

Step 2: (2S)-3-(4-carboxymethoxy-phenyl)-2-methoxy-propionic acid ethyl ester

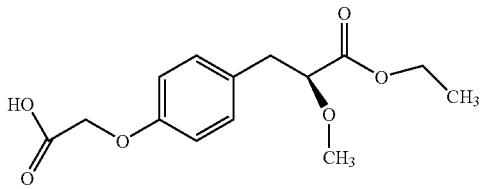

The compound of (2S)-3-(4-tert-butoxycarbonylmethoxy-phenyl)-2-methoxy-propionic acid ethyl ester (PREPARATION 3, step 1) (1.2 gr, 3.5 mmol) was solved in dichloromethane (5 ml) and trifluoroacetic acid was added (5 ml). The mixture was stirred for an hour, and the crude was concentrated to afford a yellow oil. $^{1}$H-NMR (CDCl$_3$, 200.15 MHz): 7.16 (d, 2H, J=8.3), 6.75 (d, 2H, J=8.3), 4.89 (s, 2H), 4.14 (c, 2H, J=6.9), 3.94 (t, 1H, J=6.9), 3.57 (dc, 1H), 3.35 (dc, 1H), 2.92 (d, 2H, J=6.9), 1.23-1.10 (2t, 6H).

Step 3: (2S)-2-methoxy-3-(4-{2-oxo-2-[4-(4-trifluoromethyl-phenyl)-piperazin-1-yl]-ethoxy}-phenyl)-propionic acid

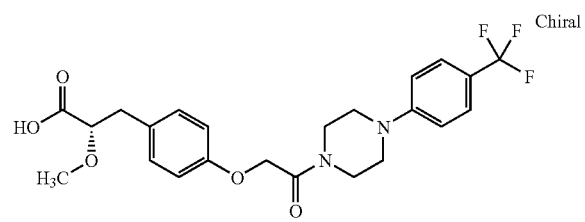

The title compound was prepared from (2S)-3-(4-carboxymethoxy-phenyl)-2-methoxy-propionic acid ethyl ester (PREPARATION 3, step 2) and 1-(4-trifluoromethyl-phenyl)-piperazine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for C$_{23}$H$_{25}$F$_3$NO$_5$ [M+H]$^+$: 467.

EXAMPLE 95

(2S)-3-(4-{[(biphenyl-4-ylmethyl)-carbamoyl]-methoxy}-phenyl)-2-methoxy-propionic acid

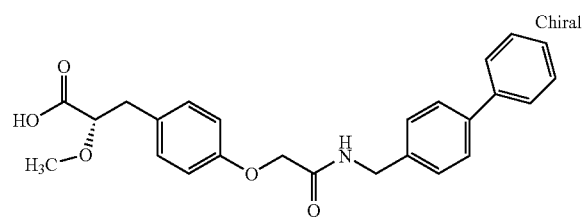

The title compound was prepared from (2S)-3-(4-carboxymethoxy-phenyl)-2-methoxy-propionic acid ethyl ester (PREPARATION 3, step 2) and C-biphenyl-4-yl-methylamine via the same procedure used for the preparation of (2S,1R)-2-ethoxy-3-(4-{1-[2-(4-phenoxy-phenyl)-ethylcarbamoyl]-ethoxy}-phenyl)propionic acid (Example 1, step 3) to produce a colorless oil. MS (ES) for C$_{25}$H$_{25}$NO$_5$ [M+H]$^+$: 420.

EXAMPLE 96

(2S)-2-methoxy-3-{4-[(methyl-naphthalen-1-ylmethyl-carbamoyl)-methoxy]-phenyl}-propionic acid

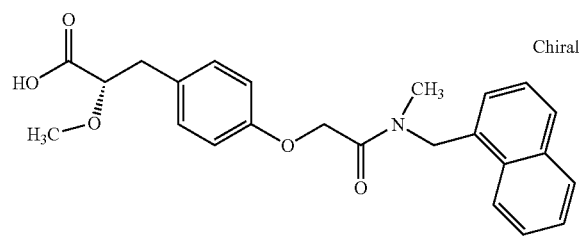

The title compound was prepared from (2S)-3-(4-carboxymethoxy-phenyl)-2-methoxy-propionic acid ethyl ester (PREPARATION 3, step 2) and methyl-naphthalen-1-ylmethyl-amine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for C$_{24}$H$_{25}$NO$_5$ [M+H]$^+$: 408.

EXAMPLE 97

(2S)-3-{4-[2-(4-benzhydryl-piperazin-1-yl)-2-oxoethoxy]-phenyl}-2-methoxy-propionic acid

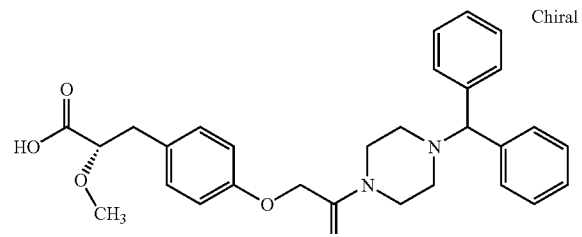

The title compound was prepared from (2S)-3-(4-carboxymethoxy-phenyl)-2-methoxy-propionic acid ethyl ester (PREPARATION 3, step 2) and 1-benzhydryl-piperazine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for C$_{29}$H$_{32}$N$_2$O$_5$ [M+H]$^+$: 489.

EXAMPLE 98

(2S)-3-[4-(2-{4-[bis-(4-fluoro-phenyl)-methyl]-piperazin-1-yl}-2-oxo-ethoxy)-phenyl]-2-methoxy-propionic acid

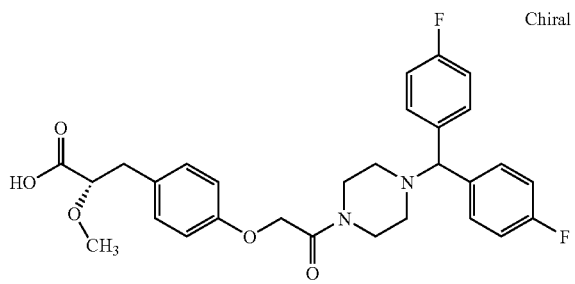

The title compound was prepared from (2S)-3-(4-carboxymethoxy-phenyl)-2-methoxy-propionic acid ethyl ester (PREPARATION 3, step 2) and 1-[bis-4-fluoro-phenyl)-methyl]-piperazine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{29}H_{30}F_2N_2O_5$ [M+H]$^+$: 525.

EXAMPLE 99

(2S)-2-methoxy-3-(4-{[2-(4-phenoxy-phenyl)-ethyl-carbamoyl]-methoxy}-phenyl)-propionic acid

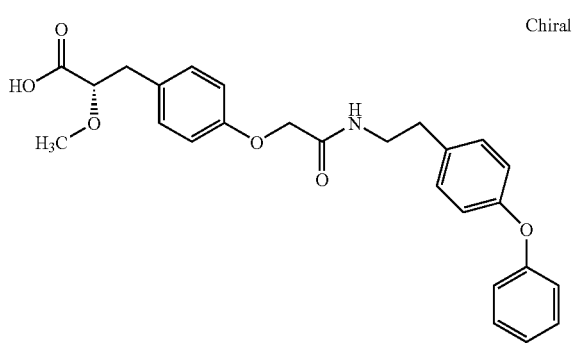

The title compound was prepared from (2S)-3-(4-carboxymethoxy-phenyl)-2-methoxy-propionic acid ethyl ester (PREPARATION 3, step 2) and 2-(4-phenoxy-phenyl)-ethylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{26}H_{27}NO_6$ [M+H]$^+$: 450.

EXAMPLE 100

(2S)-3-{4-[2-(3,4-dihydro-1H-isoquinolin-2-yl)-2-oxo-ethoxy]-phenyl}-2-methoxy-propionic acid

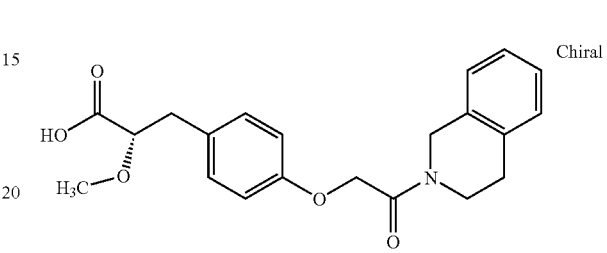

The title compound was prepared from (2S)-3-(4-carboxymethoxy-phenyl)-2-methoxy-propionic acid ethyl ester (PREPARATION 3, step 2) and 1,2,3,4-tetrahydro-isoquinoline via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a yellow oil. MS (ES) for $C_{21}H_{23}NO_5$ [M+H]$^+$: 370.

EXAMPLE 101

(2S)-3-{4-[(benzyl-phenethyl-carbamoyl)-methoxy]-phenyl}-2-methoxy-propionic acid

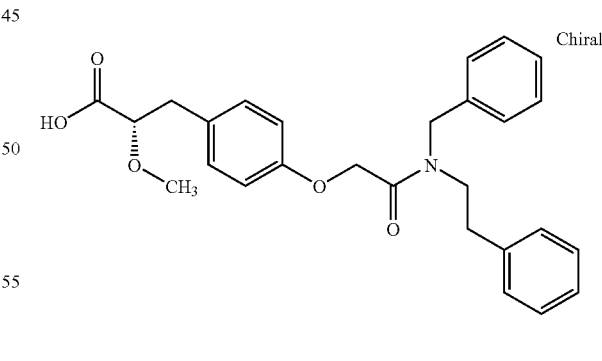

The title compound was prepared from (2S)-3-(4-carboxymethoxy-phenyl)-2-methoxy-propionic acid ethyl ester (PREPARATION 3, step 2) and benzyl-phenethyl-amine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a yellow oil. MS (ES) for $C_{27}H_{29}NO_5$ [M+H]$^+$: 448.

EXAMPLE 102

(2S)-3-(4-{2-[4-(4-fluoro-phenyl)-piperazin-1-yl]-2-oxo-ethoxy}-phenyl)-2-methoxy-propionic acid

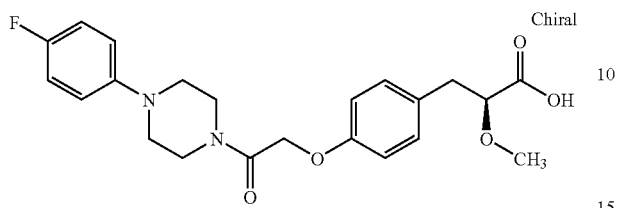

The title compound was prepared from (2S)-3-(4-carboxymethoxy-phenyl)-2-methoxy-propionic acid ethyl ester (PREPARATION 3, step 2) and 1-(4-fluoro-phenyl)-piperazine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{22}H_{25}FN_2O_5$ [M+H]$^+$: 417.

EXAMPLE 103

(2S)-2-methoxy-3-4-{[2-(2-methoxy-phenyl)-ethylcarbamoyl]-methoxy}-phenyl)-propionic acid

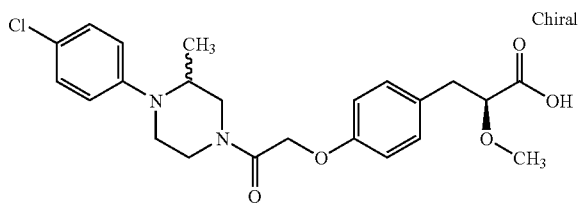

The title compound was prepared from (2S)-3-(4-carboxymethoxy-phenyl)-2-methoxy-propionic acid ethyl ester (PREPARATION 3, step 2) and 1-(4-chloro-phenyl)-2-methyl-piperazine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a yellow oil. MS (ES) for $C_{23}H_{27}ClN_2O_5$ [M+H]$^+$: 447.

EXAMPLE 104

(2S)-3-(4-{2-[4-(3-chloro-phenyl)-piperazin-1-yl]-2-oxo-ethoxy}-phenyl)-2-methoxy-propionic acid

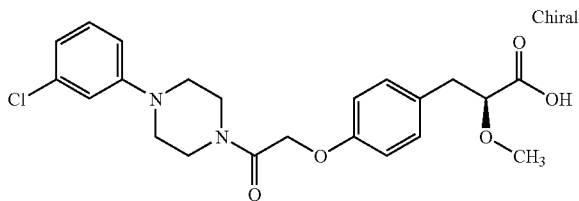

The title compound was prepared from (2S)-3-(4-carboxymethoxy-phenyl)-2-methoxy-propionic acid ethyl ester (PREPARATION 3, step 2) and 1-(3-chloro-phenyl)-piperazine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a yellow oil. MS (ES) for $C_{22}H_{25}ClN_2O_5$ [M+H]$^+$: 433.

EXAMPLE 105

(2S)-3-(4-{2-[4-(4-chloro-benzyl)-piperazin-1-yl]-2-oxo-ethoxy}-phenyl)-2-methoxy-propionic acid

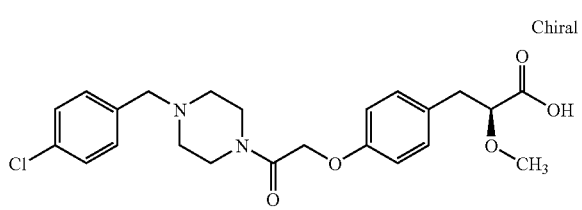

The title compound was prepared from (2S)-3-(4-carboxymethoxy-phenyl)-2-methoxy-propionic acid ethyl ester (PREPARATION 3, step 2) and 1-(4-chloro-benzyl)-piperazine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{23}H_{27}ClN_2O_5$ [M+H]$^+$: 447.

EXAMPLE 106

(2S)-3-(4-{2-[4-(2-fluoro-phenyl)-piperazin-1-yl]-2-oxo-ethoxy}-phenyl)-2-methoxy-propionic acid

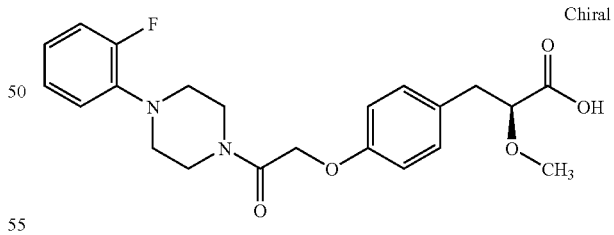

The title compound was prepared from (2S)-3-(4-carboxymethoxy-phenyl)-2-methoxy-propionic acid ethyl ester (PREPARATION 3, step 2) and 1-(2-fluoro-phenyl)-piperazine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a yellow oil. MS (ES) for $C_{22}H_{25}FN_2O_5$ [M+H]$^+$: 417.

EXAMPLE 106A (2S)-3-(4-{[(benzo[1,3]dioxol-5-ylmethyl)-carbamoyl]-methoxy}-phenyl)-2-methoxy-propionic acid

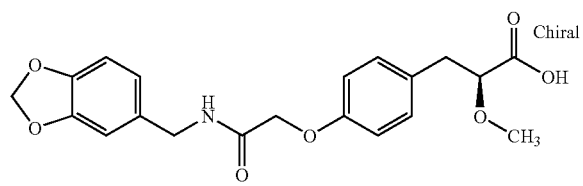

The title compound was prepared from (2S)-3-(4-carboxymethoxy-phenyl)-2-methoxy-propionic acid ethyl ester (PREPARATION 3, step 2) and C-benzo[1,3]dioxol-5-yl-methylamine via the same procedure used for the preparation of (2S,1R)-2-Ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{20}H_{21}NO_7$ $[M+H]^+$: 388.

EXAMPLE 106B (2S)-3-(4-{[2-(4-bromo-phenyl)-ethylcarbamoyl]-methoxy}-phenyl)-2-methoxy-propionic acid

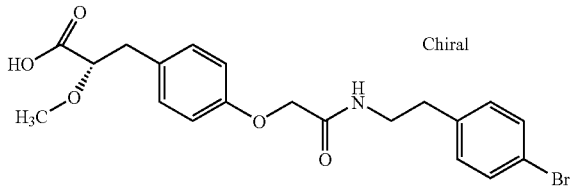

The title compound was prepared from (2S)-3-(4-carboxymethoxy-phenyl)-2-methoxy-propionic acid ethyl ester (PREPARATION 3, step 2) and 2-(4-bromo-phenyl)-ethylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{20}H_{22}BrNO_5$ $[M+H]^+$: 437.

EXAMPLE 107

(2S)-2-methoxy-3-(4-{[(naphthalen-1-ylmethyl)-carbamoyl]-methoxy}-phenyl)-propionic acid

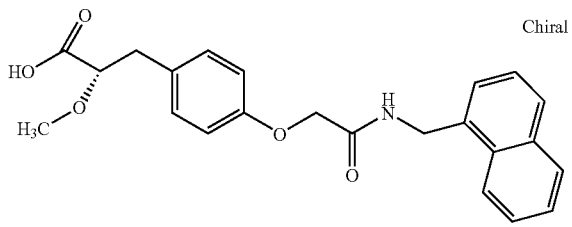

The title compound was prepared from (2S)-3-(4-carboxymethoxy-phenyl)-2-methoxy-propionic acid ethyl ester (PREPARATION 3, step 2) and C-naphthalen-1-yl-methylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{23}H_{23}NO_5$ $[M+H]^+$: 394.

EXAMPLE 108

(2S)-3-(4-{[2-(2,6-dichloro-benzylsulfanyl)-ethyl-carbamoyl]-methoxy}-phenyl)-2-methoxy-propionic acid

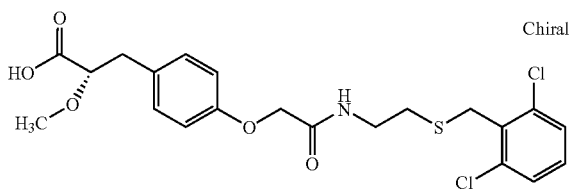

The title compound was prepared from (2S)-3-(4-carboxymethoxy-phenyl)-2-methoxy-propionic acid ethyl ester (PREPARATION 3, step 2) and C-naphthalen-1-yl-methylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a yellow oil. MS (ES) for $C_2]H_{23}Cl_2NO_5S$ $[M+H]^+$: 473.

EXAMPLE 109

(2S)-3-(4-{[benzyl-(1-phenyl-ethyl)-carbamoyl]-methoxy}-phenyl)-2-methoxy-propionic acid

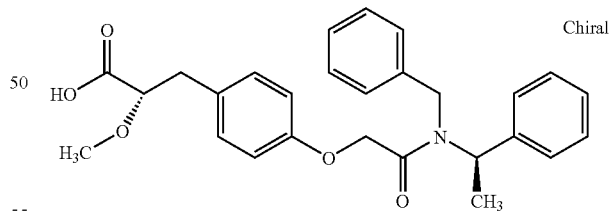

The title compound was prepared from (2S)-3-(4-carboxymethoxy-phenyl)-2-methoxy-propionic acid ethyl ester (PREPARATION 3, step 2) and (1-phenyl-ethyl)-(2-vinyl-hexa-2,4-dienyl)-amine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{27}H_{29}NO_5$ $[M+H]^+$: 448.

EXAMPLE 110

(2S)-3-(4-{2-[4-(4-acetyl-phenyl)-piperazin-1-yl]-2-oxo-ethoxy}-phenyl)-2-methoxy-propionic acid

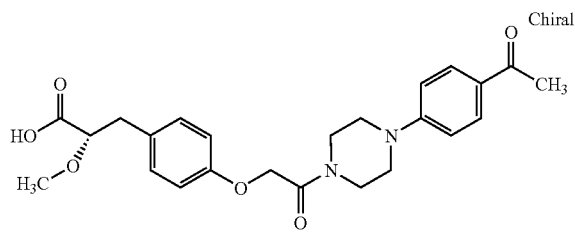

The title compound was prepared from (2S)-3-(4-carboxymethoxy-phenyl)-2-methoxy-propionic acid ethyl ester (PREPARATION 3, step 2) and 1-(4-piperazin-1-yl-phenyl)-ethanone via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{24}H_{28}N_2O_6$ $[M+H]^+$: 441.

EXAMPLE 111

(2S)-2-methoxy-3-{4-[2-oxo-2-(4-p-tolyl-piperazin-1-yl)-ethoxy]-phenyl}-propionic acid

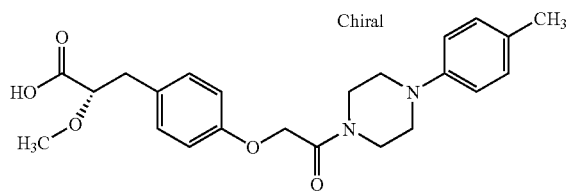

The title compound was prepared from (2S)-3-(4-carboxymethoxy-phenyl)-2-methoxy-propionic acid ethyl ester (PREPARATION 3, step 2) and 1-p-tolyl-piperazine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a yellow oil. MS (ES) for $C_{23}H_{28}N_2O_5$ $[M+H]^+$: 413.

EXAMPLE 112

(2S)-3-(4-{[ethyl-(2-fluoro-benzyl)-carbamoyl]-methoxy}-phenyl)-2-methoxy-propionic acid

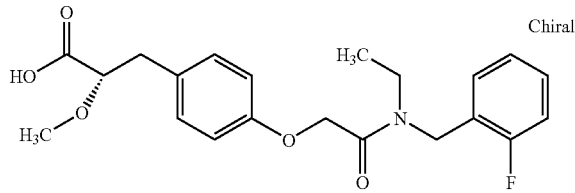

The title compound was prepared from (2S)-3-(4-carboxymethoxy-phenyl)-2-methoxy-propionic acid ethyl ester (PREPARATION 3, step 2) and ethyl-(2-fluoro-benzyl)-amine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{21}H_{24}FNO_5$ $[M+H]^+$:390.

EXAMPLE 113

(2S)-3-(4-{[ethyl-(3-methyl-benzyl)-carbamoyl]-methoxy}-phenyl)-2-methoxy-propionic acid

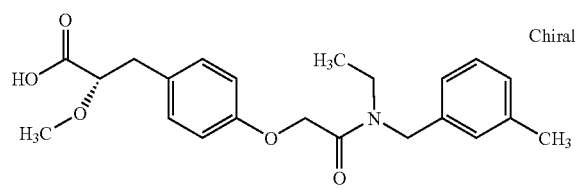

The title compound was prepared from (2S)-3-(4-carboxymethoxy-phenyl)-2-methoxy-propionic acid ethyl ester (PREPARATION 3, step 2) and ethyl-(3-methyl-benzyl)-amine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{22}H_{27}NO_5$ $[M+H]^+$: 386.

EXAMPLE 114

(2S)-3-(4-{2-[4-(4-fluoro-benzyl)-piperazin-1-yl]-2-oxo-ethoxy}-phenyl)-2-methoxy-propionic acid

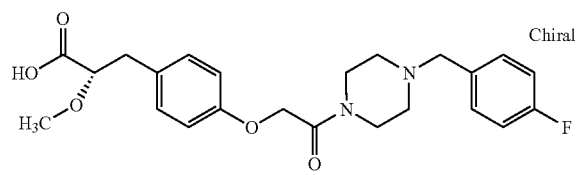

The title compound was prepared from (2S)-3-(4-carboxymethoxy-phenyl)-2-methoxy-ropionic acid ethyl ester (PREPARATION 3, step 2) and 1-(4-fluoro-benzyl)-piperazine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{23}H_{27}FN_2O_5$ $[M+H]^+$: 431.

EXAMPLE 115

(2S)-3-{4-[(6-fluoro-benzothiazol-2-ylcarbamoyl)-methoxy]-phenyl}-2-methoxy-propionic acid

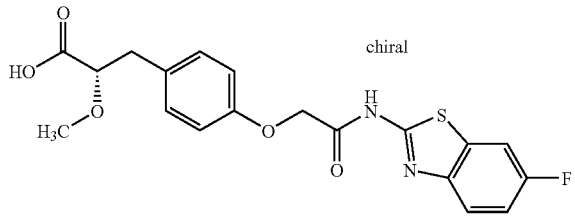

The title compound was prepared from (2S)-3-(4-carboxymethoxy-phenyl)-2-methoxy-propionic acid ethyl ester (PREPARATION 3, step 2) and 6-fluoro-benzothiazol-2-ylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{19}H_{17}FN_2O_5S$ [M+H]$^+$: 405.

EXAMPLE 116

(2S)-3-(4-{[2-(ethyl-m-tolyl-amino)-ethylcarbamoyl]-methoxy}-phenyl)-2-methoxy-propionic acid

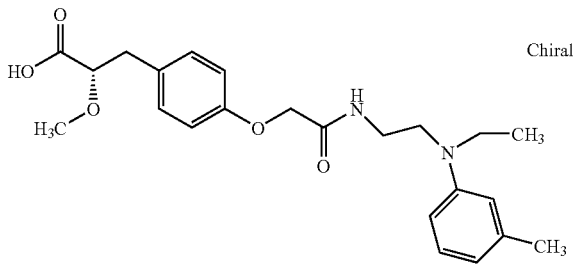

The title compound was prepared from (2S)-3-(4-carboxymethoxy-phenyl)-2-methoxy-propionic acid ethyl ester (PREPARATION 3, step 2) and N1-ethyl-N1-m-tolyl-ethane-1,2-diamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{23}H_{30}N_2O_5$ [M+H]$^+$: 414.

EXAMPLE 117

(2S)-2-methoxy-3-{4-[(2-pyridin-2-yl-ethylcarbamoyl)-methoxy]-phenyl}-propionic acid

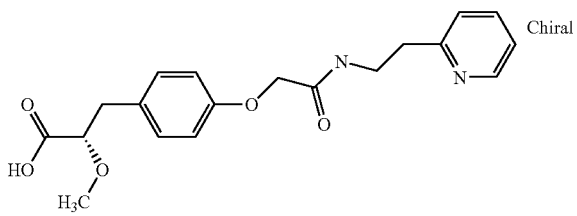

The title compound was prepared from (2S)-3-(4-carboxymethoxy-phenyl)-2-methoxy-propionic acid ethyl ester (PREPARATION 3, step 2) and 2-pyridin-2-yl-ethylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{19}H_{22}N_2O_5$ [M+H]$^+$: 359.

EXAMPLE 118

(2S)-2-methoxy-3-{4-[(2-pyridin-3-yl-ethylcarbamoyl)-methoxy]-phenyl}-propionic acid

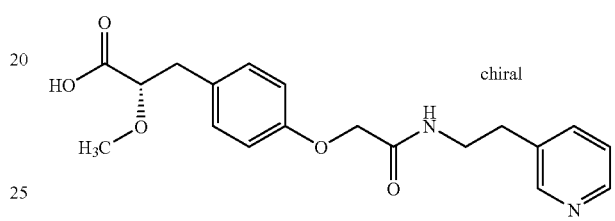

The title compound was prepared from (2S)-3-(4-carboxymethoxy-phenyl)-2-methoxy-propionic acid ethyl ester (PREPARATION 3, step 2) and 2-pyridin-3-yl-ethylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{19}H_{22}N_2O_5$ [M+H]$^+$: 359.

EXAMPLE 119

(2S)-E-3-{4-[(4-tert-butyl-cyclohexylcarbamoyl)-methoxy]-phenyl}-2-methoxy-propionic acid

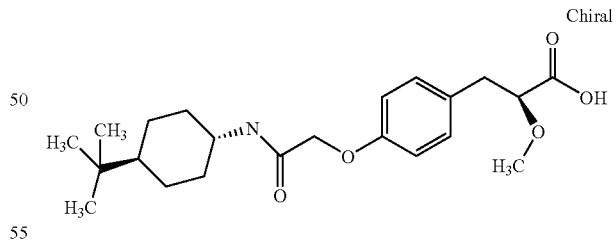

The title compound was prepared from (2S)-3-(4-carboxymethoxy-phenyl)-2-methoxy-propionic acid ethyl ester (PREPARATION 3, step 2) and E-4-tert-butyl-cyclohexylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{22}H_{33}NO_5$ [M+H]$^+$: 392.

EXAMPLE 120

(2S)-Z-3-{4-[(4-tert-butyl-cyclohexylcarbamoyl)-methoxy]-phenyl}-2-methoxy-propionic acid

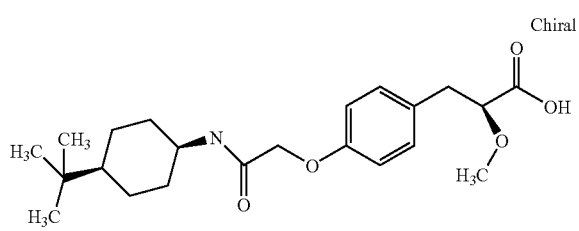

The title compound was prepared from (2S)-3-(4-carboxymethoxy-phenyl)-2-methoxy-propionic acid ethyl ester (PREPARATION 3, step 2) and Z-4-tert-butyl-cyclohexylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{22}H_{33}NO_5$ [M+H]$^+$: 392.

EXAMPLE 121

(2S)-3-(4-cyclobutylcarbamoylmethoxy-phenyl)-2-methoxy-propionic acid

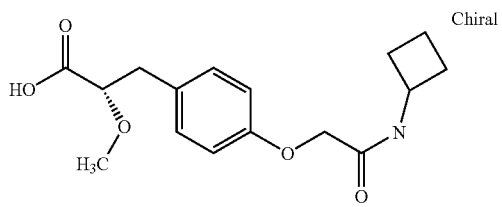

The title compound was prepared from (2S)-3-(4-carboxymethoxy-phenyl)-2-methoxy-propionic acid ethyl ester (PREPARATION 3, step 2) and cyclobutylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{16}H_{21}NO_5$ [M–H]$^-$: 306.

EXAMPLE 122

(2S)-3-{4-[(1,3-dimethyl-butylcarbamoyl)-methoxy]-phenyl}-2-methoxy-propionic acid

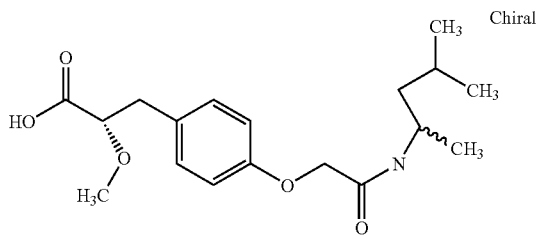

The title compound was prepared from (2S)-3-(4-carboxymethoxy-phenyl)-2-methoxy-propionic acid ethyl ester (PREPARATION 3, step 2) and 1,3-dimethyl-butylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{18}H_{27}NO_5$ [M–H]$^-$: 336.

EXAMPLE 123

(2S)-2-methoxy-3-{4-[(1-methyl-hexylcarbamoyl)-methoxy]-phenyl}-propionic acid

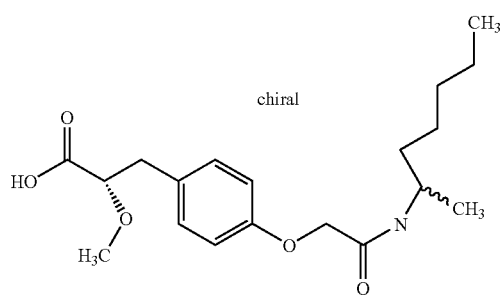

The title compound was prepared from (2S)-3-(4-carboxymethoxy-phenyl)-2-methoxy-propionic acid ethyl ester (PREPARATION 3, step 2) and 1-methyl-hexylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{19}H_{29}NO_5$ [M–H]$^-$: 350.

EXAMPLE 124

(2S)-2-methoxy-3-{4-[(1-methyl-butylcarbamoyl)-methoxy]-phenyl}-propionic acid

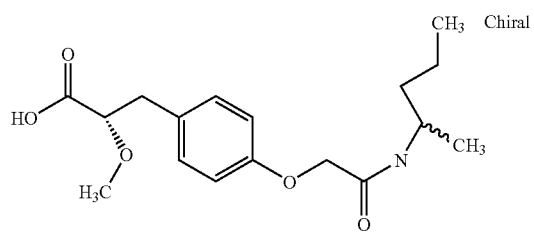

The title compound was prepared from (2S)-3-(4-carboxymethoxy-phenyl)-2-methoxy-propionic acid ethyl ester (PREPARATION 3, step 2) and 1-methyl-butylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{17}H_{25}NO_5$ [M–H]$^-$: 322.

EXAMPLE 125

(2S)-2-methoxy-3-{4-[(3-methyl-butylcarbamoyl)-methoxy]-phenyl}-propionic acid

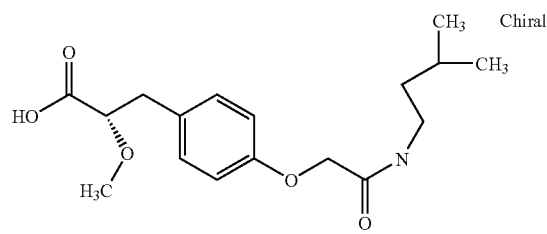

The title compound was prepared from (2S)-3-(4-carboxymethoxy-phenyl)-2-methoxy-propionic acid ethyl ester (PREPARATION 3, step 2) and 3-methyl-butylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{17}H_{25}NO_5$ [M−H]$^-$: 322.

EXAMPLE 126

(2S)-3-(4-cyclopentylcarbamoylmethoxy-phenyl)-2-methoxy-propionic acid

The title compound was prepared from (2S)-3-(4-carboxymethoxy-phenyl)-2-methoxy-propionic acid ethyl ester (PREPARATION 3, step 2) and cyclopentylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{17}H_{23}NO_5$ [M−H]$^-$: 320.

EXAMPLE 127

(2S)-2-methoxy-3-{4-[(1-methyl-3-phenyl-propyl-carbamoyl)-methoxy]-phenyl}-propionic acid

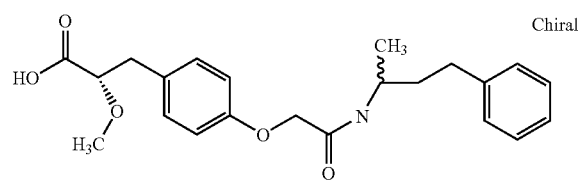

The title compound was prepared from (2S)-3-(4-carboxymethoxy-phenyl)-2-methoxy-propionic acid ethyl ester (PREPARATION 3, step 2) and 1-methyl-3-phenyl-propylamine via the same procedure used for the preparation of (2S,1R)-2-ethoxy-3-(4-{1-[2-(4-phenoxy-phenyl)-ethylcarbamoyl-ethoxy}-phenyl)-propionic acid (Example 1, step 3) to produce a colorless oil. MS (ES) for $C_{22}H_{27}NO_5$ [M−H]$^-$: 384.

EXAMPLE 128

(2S)-3-{4-[(2,2,3,3,4,4,4-heptafluoro-butlcarbamoyl)-methoxy]-phenyl}-2-methoxy-propionic acid

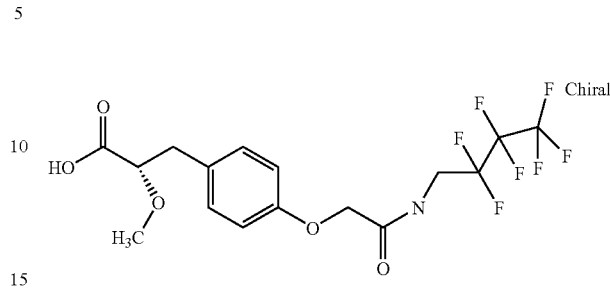

The title compound was prepared from (2S)-3-(4-carboxymethoxy-phenyl)-2-methoxy-propionic acid ethyl ester (PREPARATION 3, step 2) and nonafluorobutylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{16}H_{16}F_7NO_5$ [M−H]$^-$: 434.

EXAMPLE 129

(2S)-3-{4-[(5-tert-butyl-[1,3,4]thiadiazol-2-ylcarbamoyl)-methoxy]-phenyl}-2-methoxy-propionic acid

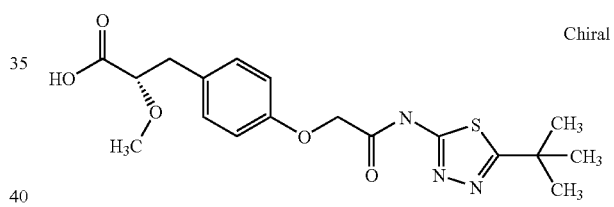

The title compound was prepared from (2S)-3-(4-carboxymethoxy-phenyl)-2-methoxy-propionic acid ethyl ester (PREPARATION 3, step 2) and 5-tert-butyl-[1,3,4]thiadiazol-2-ylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{18}H_{23}N_3O_5S$ [M−H]$^-$: 392.

EXAMPLE 130

(2S)-3-{4-[(5-tert-butyl-[1,3,4]thiadiazol-2-ylcarbamoyl)-methoxy]-phenyl}-2-methoxy-propionic acid

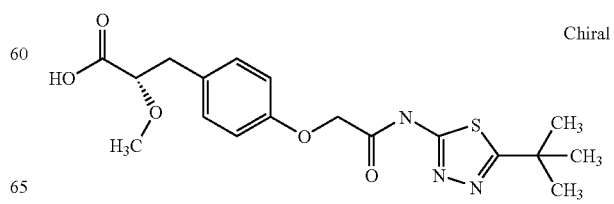

The title compound was prepared from (2S)-3-(4-carboxymethoxy-phenyl)-2-methoxy-propionic acid ethyl ester (PREPARATION 3, step 2) and 5-tert-butyl-[1,3,4]thiadiazol-2-ylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{18}H_{23}N_3O_5S$ [M–H]⁻: 392.

EXAMPLE 131

(2S)-3-{4-[(4-tert-butyl-thiazol-2-ylcarbamoyl)-methoxy]-phenyl}-2-methoxy-propionic acid

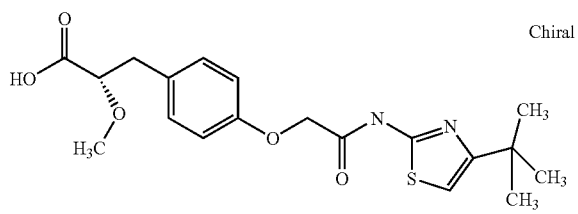

The title compound was prepared from (2S)-3-(4-carboxymethoxy-phenyl)-2-methoxy-propionic acid ethyl ester (PREPARATION 3, step 2) and 4-tert-butyl-3H-114-thiazol-2-ylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{19}H_{24}N_2O_5S$ [M–H]⁻: 391.

EXAMPLE 132

3-{4-[(5-cyclopropyl-[1,3,4]thiadiazol-2-ylcarbamoyl)-methoxy]-phenyl}-2-methoxy-propionic acid

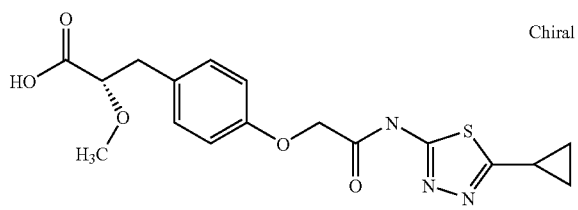

The title compound was prepared from (2S)-3-(4-carboxymethoxy-phenyl)-2-methoxy-propionic acid ethyl ester (PREPARATION 3, step 2) and 5-cyclopropyl-[1,3,4]thiadiazol-2-ylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{17}H_{19}N_3O_5S$ [M–H]⁻: 376.

EXAMPLE 133

(2S)-3-(4-hexylcarbamoylmethoxy-phenyl)-2-methoxy-propionic acid

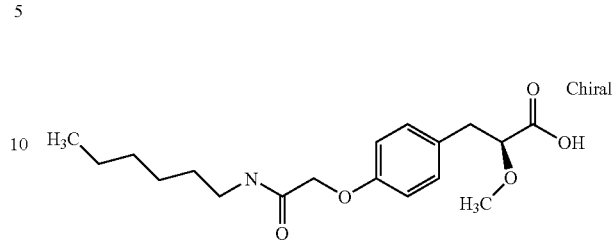

The title compound was prepared from (2S)-3-(4-carboxymethoxy-phenyl)-2-methoxy-propionic acid ethyl ester (PREPARATION 3, step 2) and hexylamine via the same procedure used for the preparation of (2S,1R)-2-Ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{18}H_{27}NO_5$ [M–H]⁻: 338.

EXAMPLE 134

(2S)-3-(4-heptylcarbamoylmethoxy-phenyl)-2-methoxy-propionic acid

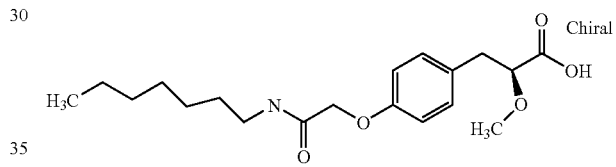

The title compound was prepared from (2S)-3-(4-carboxymethoxy-phenyl)-2-methoxy-propionic acid ethyl ester (PREPARATION 3, step 2) and heptylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{19}H_{29}NO_5$ [M–H]⁻: 352.

EXAMPLE 135

(2S)-3-{4-[(3,3-dimethyl-butylcarbamoyl)-methoxy]-phenyl}-2-methoxy-propionic acid

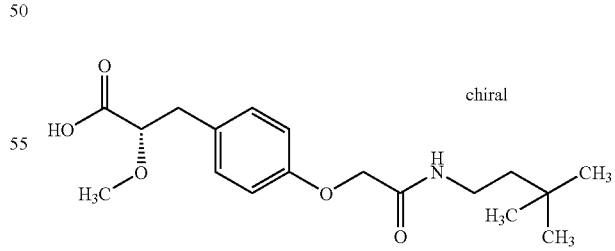

The title compound was prepared from (2S)-3-(4-carboxymethoxy-phenyl)-2-methoxy-propionic acid ethyl ester (PREPARATION 3, step 2) and 3,3-dimethyl-butylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{18}H_{27}NO_5$ [M–H]⁻: 338.

EXAMPLE 136

3-{3-[(4-cis-tert-butyl-cyclohexylcarbamoyl)-methoxy]-phenyl}-2-methoxy-propionic acid (isomer 1)

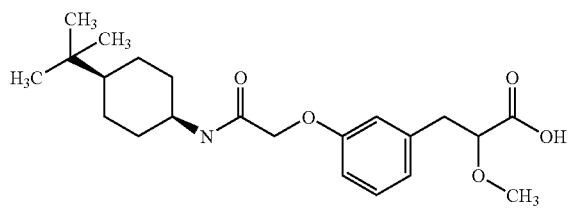

The title compound was prepared from 3-(3-carboxymethoxy-phenyl)-2-methoxy-propionic acid methyl ester (PREPARATION 4, step 2) and 4-cis-tert-butyl-cyclohexylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{22}H_{33}NO_5$ [M+H]$^+$: 392.

EXAMPLE 137

3-{3-[(4-trans-tert-butyl-cyclohexylcarbamoyl)-methoxy]-phenyl}-2-methoxy-propionic acid (isomer 2)

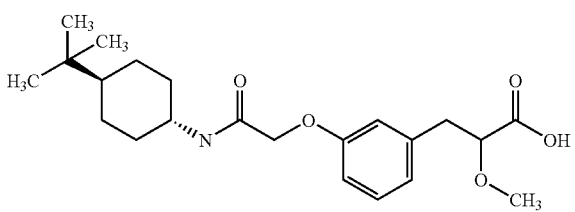

The title compound was prepared from 3-(3-carboxymethoxy-phenyl)-2-methoxy-propionic acid methyl ester (PREPARATION 4, step 2) and 4-trans-tert-butyl-cyclohexylamine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil. MS (ES) for $C_{22}H_{33}NO_5$ [M+H]$^+$: 392.

EXAMPLE 138

3-(4-heptylcarbamoylmethoxy-phenyl)-2-methoxy-2-methyl-propionic acid

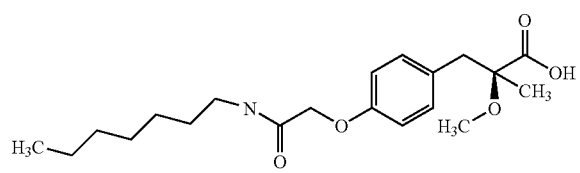

The title compound was prepared from 3-(4-carboxymethoxy-phenyl)-2-methoxy-2-methyl-propionic acid methyl ester heptyl amine via the same procedure used for the preparation of (2S,1R)-2-ethoxy-3-(4-{1-[2-(4-phenoxy-phenyl)-ethylcarbamoyl]-ethoxy}-phenyl)-propionic acid (Example 1, step 3) to produce a colorless oil.

MS (ES) for $C_{20}H_{31}NO_5$ [M+H]$^+$: 366.

EXAMPLE 139

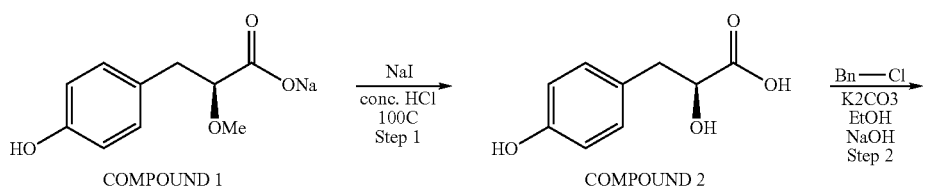

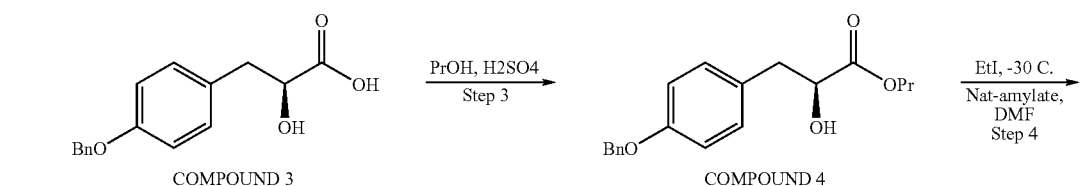

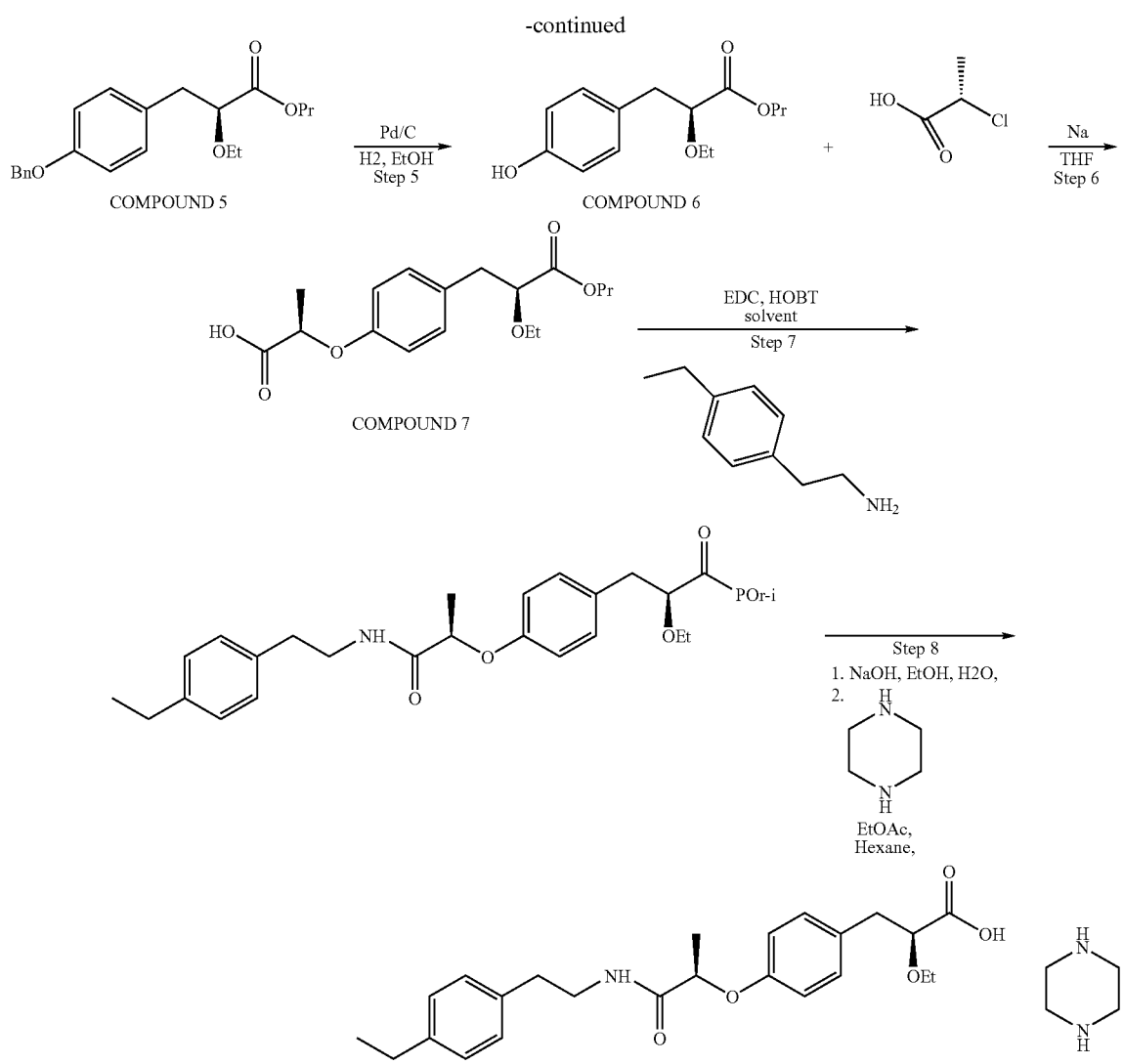

EXPERIMENTALS

Procedure: Compound 1 (204 g, 1 mole) and sodium iodide (375 g, 2.5 mole) was dissolved in 1 L of concentrated hydrochloric acid at ambient temperature. The solution was heated to reflux for 6 hr and then cooled in an ice-water bath for 2 hr. The slurry was filtered and the filter cake was washed with 300 ml cold water. The white solid was collected and dried in a vacuum oven at 60° C. to provide 178.7 g crude solid. The crude solid was stirred in 2 L of acetonitrile for 1 hr at ambient temperature. The solution was filtered and the filtrate was concentrated under vacuum to provide 123 g of Compound 2 as an off-white solid.

Synthesis of Compound 3

To the solution of Compound 2 (43.32, 0.238 mole) in absolute ethanol (950 mL) was added $K_2CO_3$ (65.73 g, 0.476 mole) and the benzyl chloride (55 mL, 0.476 mole). The suspension was refluxed for 12 hours and turned into a slurry suspension. Then ethanol was removed (65% of the total quantity), water (1 L) and sodium hydroxide (44 mL) were added until pH=13-14 in order to hydrolyse the ethyl ester formed during the reaction. After 2 h, the hydrolysis was complete.

The rest of ethanol was removed before the second addition of water (500 mL). Then the aqueous phase was extracted twice with diethylether (1000 mL) before acidifying dropwise with HCl 37% (88 mL). At this moment a yellow precipitate and an emission of $CO_2$ were observed. The solid was filtered, rinsed with water (500 mL) and dried overnight under reduced pressure at 50° C. to give COMPOUND 3 as an off white solid (60.81 g, 94%).

Synthesis of Compound 4

The solid starting material COMPOUND 3 (20 g, 73.5 mmol) is suspended in 400 ml of isopropanol and 2.2 ml of $H_2SO_4$ (41.3 mmol) is added. After 1 hour of stirring at RT, we didn't observe any dissolution of the product. The mixture is then heated at 43° C. overnight. The HPLC showed 11% (area) of remaining starting material. We added 300 ml of toluene and 200 ml of $NaHCO_3$ (saturated solution). The layers are separated, the organic one is dried over MgSO4 followed by a filtration and the evaporation on a rotavapor. We obtained 17.1 g of crude product which is 94% (HPLC area) of the desired COMPOUND 4 (yield: 74%).

The product is dissolved in toluene, filtered to clarify the solution and azeotroped twice with toluene before use in the following step.

Synthesis of Compound 5

Charge in a carefully dried and inerted 6 L reactor COMPOUND 4 (105 g; 0,334 moles) and 1000 ml anhydrous DMF. Cool the so obtained solution down to −30° C. Add at −30° C. ethyl iodide (261 g; 1,674 moles) and start than addition over 45' of a 1M solution of sodium t-amylate in toluene (420 ml; 0.42 moles) keeping T° at −27° C. to −30° C. Reaction mixture gradually changes to a suspension. After 1.5H stirring at −30° C., in-process control still indicates presence of 6% COMPOUND 4. An additional portion of 1M sodium t-amylate (30 ml, 0.03 moles) is than added and reaction mixture stirred 1H. Acetic acid (32.5 g; 1.54 moles) is than added drop-wise and temperature allowed to increase to room temperature. 2 L toluene are than added and 1.5 L DI water added at 10° C. (exothermic dissolution with temperature increasing up to 22° C.). The upper organic layer is isolated and the lower aqueous layer is diluted with 0.5 L water and re-extracted by 0.5 L toluene. The combined organic layers are washed twice with 0.5 L DI water and once with 15% NaCl solution. Solvent is than evaporated under reduced pressure up to 50° C. in order to isolate 111.9 g crude COMPOUND 5.

Crude material is than purified on 330 g silica using a cyclohexane/ethyl acetate 90/10 mixture as eluent. Purified COMPOUND 5 is isolated as a pale yellow oil, with a 90% molar yield (122.8 g; 0.3 moles).

Synthesis of Compound 6

Charge in a dried and inertised 2 L Parr hydrogenator Pd/C 10% anhydrous (8 g) and add COMPOUND 5 (80 g; 0.232 moles) dissolved in 800 ml absolute ethanol. Purge 5× with 1.5 bar Nitrogen and set under 40 PSI hydrogen pressure keeping the temperature lower than 27° C. When no more Hydrogen uptake is observed, In process sample is taken and reaction mixture is filtred on 20 g celite. Pd/C cake is rinsed twice with 50 ml ethanol, and combined solutions are concentrated under reduced pressure up to 50° C. Fresh 200 ml toluene are than added and distilled under 80 mbar at about 40° C. in order to strip out the residual ethanol. When nearly completed, distillation of the solvent is then persued at 50° C. down to 10 mbar pressure. LY2195369 is isolated as a yellowish oil (59.7 g, 0.236 moles, 100% molar yield) and stored under nitrogen and protected from light.

Synthesis of Compound 7

A 250 ml Schlenk flask equipped with a condenser and a magnetic stirrer is flushed under nitrogen. This system is dried with the heat gun.

The flask is loaded with fresh cut pieces of Na (1.4 g, 60.9 mmol, 3.0 eq). The starting material (5.1 g; 20.21 mmol; 1.0 eq.) is loaded with 100 ml of anhydrous THF. The flask that contained the starting material is rinsed with 50 ml of anhydrous THF and also adding to the reaction vessel. We immediately observed a gas evolution started on the Na surface that has a metallic aspect. The brownish red mixture is stirred at ambient temperature for 1 hour.

The chloropropionic acid (1.86 ml; 21.2 mmol, 1.05 eq, 1% $H_2O$ by KF) is added neat dropwise. The sodium surface cleaned again and about halfway trough the addition a gel formed at the top of the reaction mixture. However the bottom portion is stirred without trouble. The mixture is heated in a 55° C. oil bath; the gel can be broken, the stirring is now easy and the addition is accomplished.

The evolution of the reaction is controlled by HPLC. The reaction mixture is heated at about 50° C. during 5 hours for an almost complete conversion of the starting material. The mixture is cooled to RT and poured on 130 ml of a 5% aqueous solution of $NaH_2PO_4$ (pH=4.15). The pH after the quench is 5.8. We added 75 ml of toluene and the pH of the aqueous layer is adjusted to 2.15 with 6.5 ml of 6N HCl. By this way, all the products go to the organic layer. The layers are separated, the organic one is concentrated on a rotavapor to give 7.4 g of a crude oil (90.3 area % of the desired compound). The aqueous layer contains no products.

The crude oil (7.4 g) is taken in 50 ml of toluene and washed with aqueous saturated $NaHCO_3$ solution (2×50 ml) to remove unreacted SM. The pH of the aqueous layer is 8.3. Fresh toluene (75 ml) is added and the mixture is acidified with 6 N HCl (20 ml) to pH=2.5.

The layers are separated and the organic one is evaporated on a rotavapor to get 6 g of an oil with a crude yield of 92%.

Biological Assays

Binding and Cotransfection Studies

The in vitro potency of compounds in modulating PPARγ and PPARα receptors are determined by the procedures detailed below. DNA-dependent binding (ABCD binding) is carried out using SPA technology with PPAR receptors. Tritium-labeled PPARα and PPARγ agonists are used as radioligands for generating displacement curves and $IC_{50}$ values with compounds of the invention. Cotransfection assays are carried out in CV-1 cells. The reporter plasmid contains an acylCoA oxidase (AOX) PPRE and TK promoter upstream of the luciferase reporter cDNA. Appropriate PPARs and RXRα are constitutively expressed using plasmids containing the CMV promoter. For PPARα and PPARβ, interference by endogenous PPARγ in CV-1 cells is an issue. In order to eliminate such interference, a GAL4 chimeric system is used in which the DNA binding domain of the transfected PPAR is replaced by that of GAL4, and the GAL4 response element is utilized in place of the AOX PPRE. Cotransfection efficacy is determined relative to PPARα agonist and PPARγ agonist reference molecules. Efficacies are determined by computer fit to a concentration-response curve, or in some cases at a single high concentration of agonist (10 μM). For binding or cotransfection studies with receptors other than PPARs, similar assays are carried out using appropriate ligands, receptors, reporter constructs, etc., for that particular receptor.

These studies are carried out to evaluate the ability of compounds of the invention to bind to and/or activate various nuclear transcription factors, particularly huPPARα ("hu" indicates "human") and huPPARγ. These studies provide in vitro data concerning efficacy and selectivity of compounds of the invention. Furthermore, binding and cotransfection data for compounds of the invention are compared with corresponding data for marketed compounds that act on either huPPARα or huPPARγ.

Binding and cotransfection data for representative compounds of the invention are compared with corresponding data for reference to determine the binding.

The binding and cotransfection efficacy values found, for compounds of this invention which are useful for modulating a PPAR alpha receptor, are about $\leq 100$ nM and $\geq 50\%$, respectively. When coagoanist modulators are desired, the values may be balanced against selectivity for the gamma or another desired PPAR receptor subtype.

Evaluation of Triglyceride Reduction and HDL Cholesterol Elevation in HuapoAI

Transgenic Mice

Seventeen different series of studies are performed to evaluate the effect of compounds of the present invention upon HDL and triglyceride levels in human apoAI mice. For each compound tested, seven to eight week old male mice, transgenic for human apoAI (for example, C57BL/6-tgn (apoa1)1rub, Jackson Laboratory, Bar Harbor, Me.) are acclimated in individual cages for two weeks with standard chow diet and water provided ad libitum. After the acclimation, mice and chow are weighed and assigned to test groups (n=5) with randomization by body weight. Mice are dosed daily by oral gavage for 8 days using a 29 gauge, 1½ inch curved feeding needle. The vehicle for the controls, test compounds and the positive control is 1% carboxymethylcellulose (w/v) with 0.25% tween 80 (w/v). All mice are dosed daily between 6 and 8 a.m. with a dosing volume of 0.2 ml. Prior to termination, animals and diets are weighed and body weight change and food consumption are calculated. Three hours after last dose, mice are euthanized with $CO_2$ and blood is removed (0.5-1.0 ml) by cardiac puncture. After sacrifice, the liver, heart, and epididymal fat pad are excised and weighed. Blood is permitted to clot and serum is separated from the blood by centrifugation.

Cholesterol and triglycerides are measured colorimetrically using commercially prepared reagents (for example, as available from Sigma #339-1000 and Roche #450061 for triglycerides and cholesterol, respectively). The procedures are modified from published work (see, McGowan M. W. et al., Clin Chem 29:538-542, 1983; Allain C. C. et al., Clin Chem 20:470-475, 1974. Commnercially available standards for triglycerides and total cholesterol, respectively, commercial quality control plasma, and samples are measured in duplicate using 200 µl of reagent. An additional aliquot of sample, added to a well containing 200 µl water, provides a blank for each specimen. Plates are incubated at room temperature on a plate shaker and absorbance is read at 500 nm and 540 nm for total cholesterol and triglycerides, respectively. Values for the positive control are always within the expected range and the coefficient of variation for samples is below 10%. All samples from an experiment are assayed at the same time to minimize inter-assay variability.

Serum lipoproteins are separated and cholesterol quantitated by fast protein liquid chromatography (FPLC) coupled to an in line detection system. Cholesterol reagent (Roche Diagnostics Chol/HP 704036) is eluted at 0.16 ml/min mixed with the column effluent through a T-connection and the mixture passed through a 15 m×0.5 mm id knitted tubing reactor immersed in a 37 C water bath. The colored product produced in the presence of cholesterol is monitored in the flow strem at 505 nm and the analog voltage from the monitor is converted to a digital signal for collection and analysis. The change in voltage corresponding to change in cholesterol concentration is plotted vs time and the area under the curve corresponding to the elution of very low density lipoprotein (VLDL), low density lipoprotein (LDL) and high density lipoprotein (HDL) is calculated using Perkin Elmer Turbochrome software.

Triglyceride Serum Levels in mice dosed with a Compound of the Invention is compared to mice receiving the vehicle to identify compounds which could be particularly useful for lowering triglycerides. Generally, triglyceride decreases of greater than or equal to 30% (thirty percent) compared to control following a 30 mg/kg dose suggests a compound that can be especially useful for lowering triglyceride levels.

The percent increase of HDLc serum levels in mice receiving a compound of the invention is compared to mice receiving vehicle to identify compounds of the invention that could be particularly useful for elevating HDL levels. Generally, an increase of greater than or equal to 25% (twenty five percent) increase in HDLc level following a 30 mg/kg dose suggests a compound that can be especially useful for elevating HDLc levels.

It may be particularly desirable to select compounds of this invention that both lower triglyceride levels and increase HDLc levels. However, compounds that either lower triglyceride levels or increase HDLc levels may be desirable as well.

Evaluation of Glucose Levels in db/db Mice

The effects, upon plasma glucose of administering various dose levels of five different compounds of the present invention and a known PPAR gamma agonist or a known PPAR alpha agonist, and the control, to male db/db mice, are studied.

Five week old male diabetic (db/db) mice [for example, C57BlKs/j-m +/+ Lepr(db), Jackson Laboratory, Bar Harbor, Me.] or lean littermates are housed 6 per cage with food and water available at all times. After an acclimation period of 2 weeks, animals are individually identified by ear notches, weighed, and bled via the tail vein for determination of initial glucose levels. Blood is collected (100 µl) from unfasted animals by wrapping each mouse in a towel, cutting the tip of the tail with a scalpel, and milking blood from the tail into a heparinized capillary tube. Sample is discharged into a heparinized microtainer with gel separator and retained on ice. Plasma is obtained after centrifugation at 4° C. and glucose measured immediately. Remaining plasma is frozen until the completion of the experiment, when glucose and triglycerides are assayed in all samples. Animals are grouped based on initial glucose levels and body weights. Beginning the following morning, mice are dosed daily by oral gavage for 7 days. Treatments are test compounds (30 mg/kg), a positive control agent (30 mg/kg) or vehicle [1% carboxymethylcellulose (w/v)/0.25% Tween80 (w/v); 0.3 ml/mouse]. On day 7, mice are weighed and bled (tail vein) 3 hours after dosing. Twenty-four hours after the $7^{th}$ dose (i.e., day 8), animals are bled again (tail vein). Samples obtained from conscious animals on days 0, 7 and 8 are assayed for glucose. After the 24 hour bleed, animals are weighed and dosed for the final time. Three hours after dosing on day 8, animals are anesthetized by inhalation of isoflurane and blood obtained via cardiac puncture (0.5-0.7 ml). Whole blood is transferred to serum separator tubes, chilled on ice and permitted to clot. Serum is obtained after centrifugation at 4° C. and frozen until analysis for compound levels. After sacrifice by cervical dislocation, the liver, heart and epididymal fat pads are excised and weighed.

Glucose is measured calorimetrically using commercially purchased reagents. According to the manufacturers, the procedures are modified from published work (see, McGowan, M. W., Artiss, J. D., Strandbergh, D. R. & Zak, B. Clin Chem, 20:470-5 (1974) and Keston, A. Specific colorimetric enzymatic analytical reagents for glucose. Abstract of papers 129th Meeting ACS, 31C (1956).); and depend on the release of a mole of hydrogen peroxide for each mole of analyte, coupled with a color reaction first described by Trinder (Trinder, P. Determination of glucose in blood using glucose oxidase with an alternative oxygen acceptor. Ann Clin Biochem, 6:24 (1969)). The absorbance of the dye produced is linearly related to the analyte in the sample. The assays are further modified in our laboratory for use in a 96 well format. The commercially available standard for glucose, commercially available quality control plasma, and samples (2 or 5 µl/well) are measured in duplicate using 200 µl of reagent. An additional aliquot of sample, pipetted to a third well and diluted in 200 µl water, provided a blank for each specimen. Plates are incubated at room temperature for 18 minutes for glucose on a plate shaker and absorbance is read at 500 nm on a plate reader. Sample absorbances are compared to a standard curve (100-800 for glucose). Values for the quality control sample are always within the expected range and the coefficient of variation for samples is below 10%. All samples from an experiment are assayed at the same time to minimize interassay variability.

The results of the study, suggest compounds of the present invention that significantly reduce db/db mouse plasma glucose levels while resulting in body weight gains that are less than those observed for a known standard.

Evaluation of the Effects of Compounds of the Present Invention upon $A^y$ Mice Body Weight Fat Mass Glucose and Insulin Levels Female $A^y$ Mice Female $A^y$ mice are singly housed, maintained under standardized conditions (22° C., 12 h light:dark cycle), and provided free access to food and water throughout the duration of the study. At twenty weeks of age the mice are randomly assigned to vehicle control and treated groups based on body weight and body fat content as assessed by DEXA scanning (N=6). Mice are then dosed via oral gavage with either vehicle or a Compound of this invention (50 mg/kg) one hour after the initiation of the light cycle (for example, about 7 A.M.) for 18 days. Body weights are measured daily throughout the study. On day 14 mice are maintained in individual metabolic chambers for indirect calorimetry assessment of energy expenditure and fuel utilization. On day 18 mice are again subjected to DEXA scanning for post treatment measurement of body composition.

The results of p.o. dosing of compound for 18 days on body weight, fat mass, and lean mass are evaluated and suggest which compounds of this invention can be especially useful for maintaining desirable weight and/or promoting desired lean to fat mass.

Indirect calorimetry measurements revealed a significant reduction in respiratory quotient (RQ) in treated animals during the dark cycle [0.864±0.013 (Control) vs. 0.803±0.007 (Treated); p<0.001]. This reduction in RQ is indicative of an increased utilization of fat during the animals' active (dark) cycle. Additionally, treated animals display significantly higher rates of energy expenditure than control animals (17.40±0.49 vs. 13.62±0.26 kcal/kg/hr, respectively).

Male KK/$A^y$ Mice

Male KK/$A^y$ mice are singly housed, maintained under standardized conditions (22° C., 12 h light:dark cycle), and provided free access to food and water throughout the duration of the study. At twenty-two weeks of age the mice are randomly assigned to vehicle control and treated groups based on plasma glucose levels. Mice are then dosed via oral gavage with either vehicle or a Compound of this invention (30 mg/kg) one hour after the initiation of the light cycle (7 A.M.) for 14 days. Plasma glucose, triglyceride, and insulin levels are assessed on day 14.

The results of p.o. dosing of compound for 14 days on plasma glucose, triglycerides, and insulin are evaluated to identify compounds of this invention that may be especially desired.

Method to Elucidate the LDL-Cholesterol Total-Cholesterol and Triglyceride Lowering Effect of Compound 5(8)

Male Syrian hamsters (Harlan Sprague Dawley) weighing 80-120 g are placed on a high-fat cholesterol-rich diet for two to three weeks prior to use. Feed and water are provided ad libitum throughout the course of the experiment. Under these conditions, hamsters became hypercholesterolemic showing plasma cholesterol levels between 180-280 mg/dl. (Hamsters fed with normal chow had a total plasma cholesterol level between 100-150 mg/dl.) Hamsters with high plasma cholesterol (180 mg/dl and above) are randomized into treatment groups based on their total cholesterol level using the a commercially available program.

A Compound of this invention is dissolved in an aqueous vehicle (containing CMC with Tween 80) such that each hamster receives once a day approx. 1 ml of the solution by garvage at doses 3 and 30 mg/kg body weight. Fenofibrate (Sigma Chemical, prepared as a suspension in the same vehicle) is given as a known alpha-agonist control at a dose of 200 mg/kg, and the blank control is vehicle alone. Dosing is performed daily in the early morning for 14 days.

Quantification of Plasma Lipids:

On the last day of the test, hamsters are bled (400 ul) from the suborbital sinus while under isoflurane anesthesia 2 h after dosing. Blood samples are collected into heparinized microfuge tubes chilled in ice bath. Plasma samples are separated from the blood cells by brief centrifugation. Total cholesterol and triglycerides are determined by means of enzymatic assays carried out automatically in the Monarch equipment (Instrumentation Laboratory) following the manufacturer's precedure. Plasma lipoproteins (VLDL, LDL and HDL) are resolved by injecting 25 ul of the pooled plasma samples into an FPLC system eluted with phosphate buffered saline at 0.5 ml/min through a 6 HR 10/30 column maintained room temp. Detection and characterization of the isolated plasma lipids are accomplished by postcolumn incubation of the effluent with a Cholesterol/HP reagent (for example, Roche Lab System; infused at 0.12 ml/min) in a knitted reaction coil maintained at 37° C. The intensity of the color formed is proportional to the cholesterol concentration and is measured photometrically at 505 nm.

The effect of administration of a Compound of this invention for 14 days is studied for the percent reduction in LDL level with reference to the vehicle group. The LDL-lowering efficacy for especially desired compounds of this invention is markedly more potent than that of fenofibrate. Compounds of this invention that decrease LDL greater than or equal to 30% (thirty percent) compared to vehicle can be especially desired.

The total-cholesterol and triglyceride lowering effects of a Compound of this invention is also studied. The data for reduction in total cholesterol and triglyceride levels after treatment with a compound of this invention for 14 days is compared to the vehicle to suggest compounds that can be particularly desired. The effect of the known control is measured.

Method to Elucidate the Fibrinogen-Lowering Effect of PPARModulators

Zucker Fatty Rat Model:

The life phase of the study on fibrinogen-lowering effect of compounds of this invention is part of the life phase procedures for the antidiabetic studies of the same compounds. On the last (14th) day of the treatment period, with the animals placed under surgical anesthesia, ~3 ml of blood is collected, by cardiac puncture, into a syringe containing citrate buffer. The blood sample is chilled and centrifuged at 4° C. to isolate the plasma that is stored at −70° C. prior to fibrinogen assay.

Quantification of Rat Plasma Fibrinogen:

Rat plasma fibrinogen levels are quantified by using a commercial assay system consists of a coagulation instrument following the manufacturer's protocol. In essence, 100 ul of plasma is sampled from each specimen and a 1/20 dilution is prepared with buffer. The diluted plasma is incubated at 37° C. for 240 seconds. Fifty microliters of clotting reagent thrombin solution (provided by the instrument's manufacturer in a standard concentration) is then added. The instrument monitors the clotting time, a function of fibrinogen concentration quantified with reference to standard samples.

Results:

Compounds of this invention may be capable of lowering fibrinogen level in vivo. Compounds that lower fibrinogen level greater than vehicle can be especially desired.

Cholesterol and triglyceride lowering effects of compounds of this invention may also produced in Zucker rats.

Method to Elucidate the Anti-Body Weight Gain and Anti-Appetite Effects of Compounds of this Invention Fourteen-Day Study in Zucker Fatty Rat[1] or ZDF Rat[2] Models:

Male Zucker Fatty rats, non-diabetic (Charles River Laboratories, Wilmington, Mass.) or male ZDF rats (Genetic Models, Inc, Indianapolis, Ind.) of comparable age and weight are acclimated for 1 week prior to treatment. Rats are on normal chow and water is provided ad libitum throughout the course of the experiment.

α-agonists are dissolved in an aqueous vehicle such that each rat received once a day approximately 1 ml of the solution by garvage at doses 0.1, 0.3, 1 and 3 mg/kg body weight. Fenofibrate (Sigma Chemical, prepared as a suspension in the same vehicle) a known alpha-agonist given at doses of 300 mg/kg, as well as the vehicle are controls. Dosing is performed daily in the early morning for 14 days. Over the course of the experiment, body weight and food consumption are monitored. Using this assay, compounds of this invention can be identified that can be especially desired and may result in significant weight reduction.

Certain Features of the present invention may be preferred for pharmaceutical use. The following embodiments of the present invention and characteristics of compounds within the scope of the present invention are listed in tabular form and one or more may be independently combined to provide a variety of desired compounds and embodiments of the present invention. The following tabular list of embodiments is illustrative of the present invention and is in no way intended to limit the scope of the claimed invention.

A) A compound of the formula:

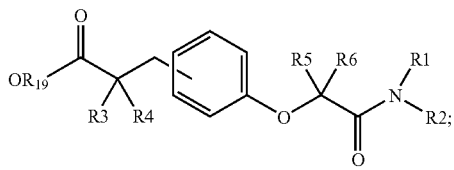

B) A compound of the formula:

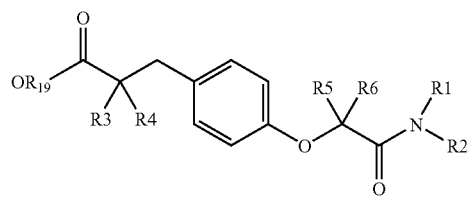

C) A compound of the formula:

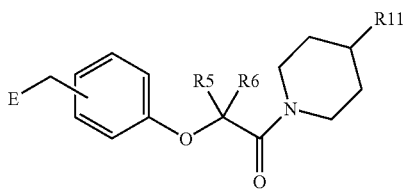

D) A compound of the formula:

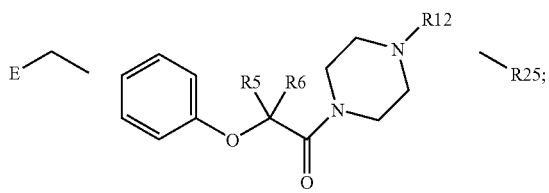

E) R2 is selected from the group consisting of

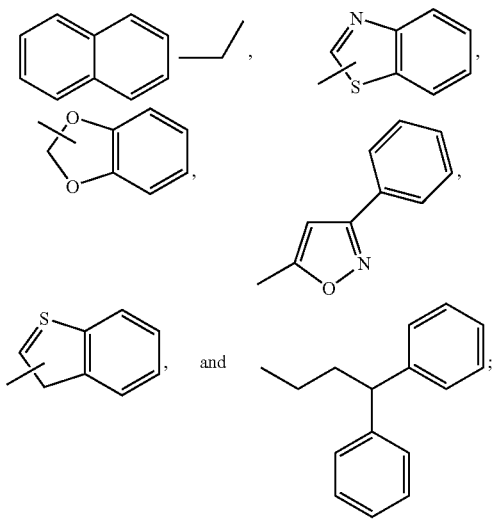

F) R2 is —CH(C(O)OCH$_3$)benzyl;

G) R6 is selected from the group consisting of hydrogen, $C_1$-$C_4$ alkl and aryl-$C_{0-4}$-alkyl, and which $C_1$-$C_4$ alkl and aryl-$C_{0-4}$-alkyl are each independently substituted with a group selected from R5';

H) R2 is arylalkyl wherein the aryl is phenyl and the alkyl is C2-C3 alkyl, and the phenyl is substituted with from one to three groups each independently selected from R2';

I) R1 is hydrogen;
J) R2 is aryl(C₂-C₃)alkyl which is unsubstituted or substituted with from one to three substituents each independently selected from R2';
K) R2 is arylalkyl substituted by C1-C2 alkyl;
L) R5 is H or methyl.
M) A compound of the formula:

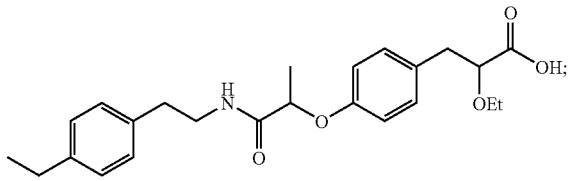

N) R6 is C₁-C₃ alkyl;
O) R6 is methyl;
P) E is C(R3)(R4)A;
Q) R5 is hydrogen or methyl;
R) R3 is C₁-C₃alkoxy;
S) E is C(R3)(R4)A and A is C(O)OR26; R26 is H or C₁-C₃alkyl;
T) A compound which is selected from the group consisting of:
(2S,1'R)-2-Ethoxy-3-(4-{1'-[2-(4-phenoxy-phenyl)-ethylcarbamoyl]-ethoxy}-phenyl)-propionic acid; (2S,1'R)-2-Ethoxy-3-(4-{1'-[2-(4-ethyl-phenyl)-ethylcarbamoyl]-ethoxy}-phenyl)-propionic acid; (2S,1'R)-2-ethoxy-3-(4-{1'-[2-(4-trifluoromethylphenyl)-ethylcarbamoyl]-ethoxy}-phenyl)-propionic acid;
(2S,1'R)-2-ethoxy-3-(4-{1'-[2-(2-ethoxy-phenyl)-ethylcarbamoyl]-ethoxy}-phenyl)-propionic acid;
(2S,1'R)-2-ethoxy-3-{4-[1'-(3-trifluoromethyl-benzylcarbamoyl)-ethoxy]-phenyl}-propionic acid;
(2S,1'R)-2-ethoxy-3-{4-[1'-(3-fluoro-5-trifluoromethyl-benzylcarbamoyl)-ethoxy]-phenyl}-propionic acid;
(2S,1'R)-3-(4-{1'-[(biphenyl-3-ylmethyl)-carbamoyl]-ethoxy}-phenyl)-2-ethoxy-propionic acid;
(2S,1R)-3-(4-{1'-[2-(3-chloro-phenyl)-ethylcarbamoyl]-ethoxy}-phenyl)-2-ethoxy-propionic acid;
(2S,1'R)-2-ethoxy-3-(4-{1'-[2-(3-fluoro-phenyl)-ethylcarbamoyl]-ethoxy}-phenyl)-propionic acid;
(2S,1'R)-2-ethoxy-3-(4-{1'-[2-(2-fluoro-phenyl)-ethylcarbamoyl]-ethoxy}-phenyl)-propionic acid;
(2S,1'R)-3-(4-{1'-[2-(2,4-dichloro-phenyl)-ethylcarbamoyl]-ethoxy}-phenyl)-2-ethoxy-propionic acid;
(2S,1'R)-3-(4-{1'-[2-(2,6-dichloro-phenyl)-ethylcarbamoyl]-ethoxy}-phenyl)-2-ethoxy-propionic acid;
(2S,1'R)-3-(4-{1'-[2-(2-chloro-phenyl)-ethylcarbamoyl]-ethoxy}-phenyl)-2-ethoxy-propionic acid; (2S,1'R)-3-(4-{1'-[2-(4-tert-butyl-phenyl)-ethylcarbamoyl]-ethoxy}-phenyl)-2-ethoxy-propionic acid;
(2S,1'R)-2-ethoxy-3-{4-[1'-(4-fluoro-benzylcarbamoyl)-ethoxy]-phenyl}-propionic acid;(2S,1'R)-2-ethoxy-3-{4-[1'-(4-trifluoromethyl-benzylcarbamoyl)-ethoxy]-phenyl}-propionic acid;
(2S,1'R)-3-{4-[1'-(4-tert-butyl-benzylcarbamoyl)-ethoxy]-phenyl}-2-ethoxy-propionic acid; (2S,1'R)-3-{4-[1'-(4-tert-butyl-phenylcarbamoyl)-ethoxy]-phenyl}-2-ethoxy-propionic acid;(2S,1'R)-3-{4-[1'-(4-trans-tert-butyl-cyclohexylcarbamoyl)-ethoxy]-phenyl}-2-ethoxy-propionic acid;
(2S)-3-{4-[1-(4-tert-butyl-cyclohexylcarbamoyl)-1-methyl-ethoxy]-phenyl}-2-methoxy-propionic acid;

(2S)-2-methoxy-3-(4-{1-methyl-1-[2-(4-phenoxy-phenyl)-ethylcarbamoyl]-ethoxy}-phenyl)-propionic acid;
(2S)-3-(4-{1-[2-(2-ethoxy-phenyl)-ethylcarbamoyl]-1-methyl-ethoxy}-phenyl)-2-methoxy-propionic acid;
2-methoxy-3-(4-{1-methyl-1-[2-(3-trifluoromethyl-phenyl)-ethylcarbamoyl]-ethoxy}-phenyl)-propionic acid;
(2S)-2-methoxy-3-{4-[1-methyl-1-(3-trifluoromethyl-benzylcarbamoyl)-ethoxy]-phenyl}-propionic acid; (2S)-3-(4-{1-[2-(2-chloro-phenyl)-ethylcarbamoyl]-1-methyl-ethoxy}-phenyl)-2-methoxy-propionic acid;
(2S)-3-(4-{1-[(biphenyl-3-ylmethyl)-carbamoyl]-1-methyl-ethoxy}-phenyl)-2-methoxy-propionic acid;
(2S)-3-(4-{1-[2-(2,5-dimethoxy-phenyl)-ethylcarbamoyl]-1-methyl-ethoxy}-phenyl)-2-methoxy-propionic acid;
(2S)-3-(4-{1-[2-(2-fluoro-phenyl)-ethylcarbamoyl]-1-methyl-ethoxy}-phenyl)-2-methoxy-propionic acid;
(2S)-2-ethoxy-3-(4-{1-methyl-1-[2-(3-trifluoromethyl-phenyl)-ethylcarbamoyl]-ethoxy}-phenyl)-propionic acid;
(2S)-2-ethoxy-3-{4-[1-(3-fluoro-5-trifluoromethyl-benzylcarbamoyl)-1-methyl-ethoxy]-phenyl}-propionic acid;
(2S)-3-(4-{1-[2-(2-chloro-phenyl)-ethylcarbamoyl]-1-methyl-ethoxy}-phenyl)-2-ethoxy-propionic acid; (2S)-3-(4-{1-[(biphenyl-3-ylmethyl)-carbamoyl]-1-methyl-ethoxy}-phenyl)-2-ethoxy-propionic acid;
(2S)-3-(4-{1-[2-(3-chloro-phenyl)-ethylcarbamoyl]-1-methyl-ethoxy}-phenyl)-2-ethoxy-propionic acid;
(2S)-3-(4-{1-[2-(2,5-dimethoxy-phenyl)-ethylcarbamoyl]-1-methyl-ethoxy}-phenyl)-2-ethoxy-propionic acid;
(2S)-2-ethoxy-3-(4-{1-[2-(2-fluoro-phenyl)-ethylcarbamoyl]-1-methyl-ethoxy}-phenyl)-propionic acid;
(2S)-3-{3-[1-(4-tert-butyl-cyclohexylcarbamoyl)-1-methyl-ethoxy]-phenyl}-2-methoxy-propionic acid;
(2S)-3-{3-[1-(3-fluoro-5-trifluoromethyl-benzylcarbamoyl)-1-methyl-ethoxy]-phenyl}-2-methoxy-propionic acid;
(2S)-3-(3-{1-[(biphenyl-3-ylmethyl)-carbamoyl]-1-methyl-ethoxy}-phenyl)-2-methoxy-propionic acid;
(2S)-3-(3-{1-[2-(3-chloro-phenyl)-ethylcarbamoyl]-1-methyl-ethoxy}-phenyl)-2-methoxy-propionic acid;
(2S)-2-methoxy-3-{4-[(1-phenyl-ethylcarbamoyl)-methoxy]-phenyl}-propionic acid;
(2S)-3-(3-{1-[2-(2,4-dichloro-phenyl)-ethylcarbamoyl]-1-methyl-ethoxy}-phenyl)-2-methoxy-propionic acid;
(2S)-3-(3-{1-[2-(2,6-dichloro-phenyl)-ethylcarbamoyl]-1-methyl-ethoxy}-phenyl)-2-methoxy-propionic acid;
(2S)-3-(4-{1-[2-(2,4-dichloro-phenyl)-ethylcarbamoyl]-1-methyl-ethoxy}-phenyl)-2-methoxy-propionic acid;
(2S)-3-(4-{1-[2-(2,4-dichloro-phenyl)-ethylcarbamoyl]-1-methyl-ethoxy}-phenyl)-2-ethoxy-propionic acid;
(2S)-3-(4-{1-[2-(2,6-dichloro-phenyl)-ethylcarbamoyl]-1-methyl-ethoxy}-phenyl)-2-ethoxy-propionic acid;
(2S)-2-ethoxy-3-(4-{1-[2-(4-ethyl-phenyl)-ethylcarbamoyl]-1-methyl-ethoxy}-phenyl)-propionic acid;
(2S)-2-ethoxy-3-(4-{1-[2-(2-ethoxy-phenyl)-ethylcarbamoyl]-1-methyl-ethoxy}-phenyl)-propionic acid;
2-Ethoxy-3-{4-[1-(3-trifluoromethyl-benzylcarbamoyl)-ethoxy]-phenyl}-propionic acid;
2-Ethoxy-3-{4-[1-(5-fluoro-3-trifluoromethyl-benzylcarbamoyl)-ethoxy]-phenyl}-propionic acid;
2-Ethoxy-3-{4-[1-(3-phenyl-benzylcarbamoyl)-ethoxy]-phenyl}-propionic acid;
2-Ethoxy-3-{4-[1-(4-phenoxy-phenylethylcarbamoyl)-ethoxy]-phenyl}-propionic acid;
2-Ethoxy-3-{4-[1-(3-trifluoromethyl-phenylethylcarbamoyl)-ethoxy]-phenyl}-propionic acid;
3-(4-{1-[2-(2,6-Dichloro-phenyl)-ethylcarbamoyl]-ethoxy}-phenyl)-2-ethoxy-propionic acid;

2-Ethoxy-3-(4-{1-[2-(4-ethyl-phenyl)-ethylcarbamoyl]-ethoxy}-phenyl)-propionic acid;
2-Ethoxy-3-(4-{1-[2-(4-ethyl-phenyl)-ethylcarbamoyl]-ethoxy}-phenyl)-propionic acid;
3-(4-{Cyclohexyl-[2-(4-ethyl-phenyl)-ethylcarbamoyl]-methoxy}-phenyl)-2-ethoxy-propionic acid;
2-Ethoxy-3-(4-{1-[2-(4-ethyl-phenyl)-ethylcarbamoyl]-2-phenyl-ethoxy}-phenyl)-propionic acid; and
(2S,1'R)-2-ethoxy-3-{4-[1'-(2-thiophen-2-yl-ethylcarbamoyl)-ethoxy]-phenyl}-propionic acid; and pharmaceutically acceptable salts thereof;

U) A compound selected from the group consisting of
(2S,1'R)-3-{4-[1'-(4-tert-butyl-cyclohexylcarbamoyl)-ethoxy]-phenyl}-2-ethoxy propionic acid;
(2S,1'R)-2-ethoxy-3-(4-{1'-[(thiophen-2-ylmethyl)-carbamoyl]-ethoxy}-phenyl)-propionic acid;
(2S,1'R)-2-ethoxy-3-{4-[1'-(2-thiophen-2-yl-ethylcarbamoyl)-ethoxy]-phenyl}-propionic acid; and
pharmaceutically acceptable salts thereof;

V) A compound selected from the group consisting of
(2S,1'R)-2-ethoxy-3-[4-(1'-heptylcarbamoyl-ethoxy)-phenyl]-propionic acid;
(2S)-3-[3-(1-heptylcarbamoyl-1-methyl-ethoxy)-phenyl]-2-methoxy-propionic acid;
(2S)-2-ethoxy-3-[4-(1-heptylcarbamoyl-1-methyl-ethoxy)-phenyl]-propionic acid;
2-Ethoxy-3-(4-{1-[2-(4-ethyl-phenyl)-ethylcarbamoyl]-propoxy}-phenyl)-propionic acid;
2-Ethoxy-3-(4-{1-[2-(4-phenoxy-phenyl)-ethylcarbamoyl]-propoxy}-phenyl)-propionic acid; and
pharmaceutically acceptable salts thereof;

W) A compound selected from the group consisting of
(2S)-3-(4-{2-[4-(4-fluoro-benzoyl)-piperidin-1-yl]-2-oxo-ethoxy}-phenyl)-2-methoxy-propionic acid;
(2S)-3-(4-{2-[4-(4-chloro-benzoyl)-piperidin-1-yl]-2-oxo-ethoxy}-phenyl)-2-methoxy-propionic acid;
(2S)-3-[4-(2-{4-[bis-(4-fluoro-phenyl)-methyl]-piperazin-1-yl}-2-oxo-ethoxy)-phenyl]-2-methoxy-propionic acid;
(2S)-3-(4-{2-[4-(2-fluoro-phenyl)-piperazin-1-yl]-2-oxo-ethoxy}-phenyl)-2-methoxy-propionic acid;
2S)-3-[4-(2-{4-[(4-chloro-phenyl)-phenyl-methyl]-piperazin-1-yl}-2-oxo-ethoxy)-phenyl]-2-methoxy-propionic acid;
(2S)-3-(4-{2-[4-(4-acetyl-phenyl)-piperazin-1-yl]-2-oxo-ethoxy}-phenyl)-2-methoxy-propionic acid;
(2S)-3-[4-(2-{4-[(4-chloro-phenyl)-phenyl-methyl]-piperazin-1-yl}-2-oxo-ethoxy)-phenyl]-2-methoxy-propionic acid;
(2S)-3-{4-[2-(4-benzhydryl-piperazin-1-yl)-2-oxo-ethoxy]-phenyl}-2-methoxy-propionic acid;
(2S)-3-(4-{2-[4-(4-fluoro-benzyl)-piperazin-1-yl]-2-oxo-ethoxy}-phenyl)-2-methoxy-propionic acid;
(2S)-3-{4-[2-(3,4-dihydro-1H-isoquinolin-2-yl)-2-oxo-ethoxy]-phenyl}-2-methoxy-propionic acid;

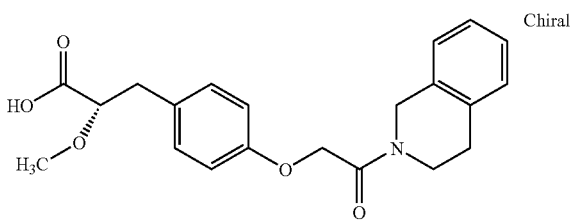

(2S)-3-(4-{2-[4-(4-fluoro-phenyl)-piperazin-1-yl]-2-oxo-ethoxy}-phenyl)-2-methoxy-propionic acid;
(2S)-2-methoxy-3-4-{[2-(2-methoxy-phenyl)-ethylcarbamoyl]-methoxy}-phenyl)-propionic acid;
(2S)-3-(4-{2-[4-(3-chloro-phenyl)-piperazin-1-yl]-2-oxo-ethoxy}-phenyl)-2-methoxy-propionic acid;
(2S)-3-(4-{2-[4-(4-chloro-benzyl)-piperazin-1-yl]-2-oxo-ethoxy}-phenyl)-2-methoxy-propionic acid; 2S)-2-methoxy-3-{4-[2-oxo-2-(4-p-tolyl-piperazin-1-yl)-ethoxy]phenyl}-propionic acid;
2S)-2-methoxy-3-(4-{2-oxo-2-[4-(4-trifluoromethyl-phenyl)-piperazin-1-yl]-ethoxy}-phenyl)-propionic acid; and
a pharmaceutically acceptable salt thereof.

X) A compound selected from the group consisting of
(2S)-3-(4-{[benzyl-(1-phenyl-ethyl)-carbamoyl]-methoxy}-phenyl)-2-methoxy-propionic acid

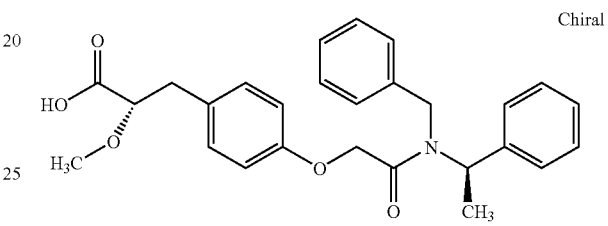

(2S)-3-(4-{[ethyl-(2-fluoro-benzyl)-carbamoyl]-methoxy}-phenyl)-2-methoxy-propionic acid;
(2S)-3-[4-({ethyl-[2-(4-methoxy-phenyl)-1-methyl-ethyl]-carbamoyl}-methoxy)-phenyl]-2-methoxy-propionic acid;
(2S)-3-(4-{[ethyl-(3-methyl-benzyl)-carbamoyl]-methoxy}-phenyl)-2-methoxy-propionic acid;
(2S)-2-methoxy-3-{4-[(methyl-naphthalen-1-ylmethyl-carbamoyl)-methoxy]-phenyl}-propionic acid;
(2S)-3-(4-{[butyl-(1-phenyl-ethyl)-carbamoyl]-methoxy}-phenyl)-2-methoxy-propionic acid;
(2S)-3-(4-{[butyl-(1-phenyl-ethyl)-carbamoyl]-methoxy}-phenyl)-2-methoxy-propionic acid;
(2S)-2-methoxy-3-(4-{[methyl-(1-phenyl-ethyl)-carbamoyl]-methoxy}-phenyl)-propionic acid;
(2S)-3-(4-{[benzyl-(2-ethoxycarbonyl-ethyl)-carbamoyl]-methoxy}-phenyl)-2-methoxy-propionic acid; and
pharmaceutically acceptable salts there.

Y) A compound as Claimed by Claim 1 wherein the compound is selected from the group consisting of:
(2S)-3-(4-{[benzyl-(2-ethoxycarbonyl-ethyl)-carbamoyl]-methoxy}-phenyl)-2-methoxy-propionic acid;
S)-3-{4-[(benzyl-phenethyl-carbamoyl)-methoxy]-phenyl}-2-methoxy-propionic acid;
(2S)-2-methoxy-3-{4-[(1-methoxycarbonyl-2-phenyl-ethylcarbamoyl)-methoxy]-phenyl}-propionic acid;
(2S)-3-(4-{[benzyl-(2-ethoxycarbonyl-ethyl)-carbamoyl]-methoxy}-phenyl)-2-methoxy-propionic acid;
(2S)-3-(4-{[(benzo[1,3]dioxol-5-ylmethyl)-carbamoyl]-methoxy}-phenyl)-2-methoxy-propionic acid;
(2S)-3-{4-[(6-fluoro-benzothiazol-2-ylcarbamoyl)-methoxy]-phenyl}-2-methoxy-propionic acid;
(2S)-2-methoxy-3-{4-[(1-naphthalen-1-yl-ethylcarbamoyl)-methoxy]-phenyl}-propionic acid;
(2S)-2-methoxy-3-(4-{[(naphthalen-1-ylmethyl)-carbamoyl]-methoxy}-phenyl)-propionic acid;
(2S)-3-(4-{[2-(2,6-dichloro-benzylsulfanyl)-ethylcarbamoyl]-methoxy}-phenyl)-2-methoxy-propionic acid;

(2S)-3-[4-({[(4-chloro-phenyl)-phenyl-methyl]-carbamoyl}-methoxy)-phenyl]-2-methoxy-propionic acid;
(2S)-3-{4-[(3,3-diphenyl-propylcarbamoyl)-methoxy]-phenyl}-2-methoxy-propionic acid;
2-methoxy-2-methyl-3-(4-{[2-(4-phenoxy-phenyl)-ethylcarbamoyl]-methoxy}-phenyl)-propionic acid;
(2S)-2-methoxy-3-(4-{[3-(methyl-phenyl-amino)-propylcarbamoyl]-methoxy}-phenyl)-propionic acid;
(2S)-2-methoxy-3-(4-{[3-(methyl-phenyl-amino)-propylcarbamoyl]-methoxy}-phenyl)-propionic acid;
(2S)-2-methoxy-3-{4-[(1-methoxycarbonyl-2-phenyl-ethylcarbamoyl)-methoxy]-phenyl}-propionic acid;
(2S)-2-methoxy-3-{4-[(2-pyridin-2-yl-ethylcarbamoyl)-methoxy]-phenyl}-propionic acid;
(2S)-E-3-{4-[(4-tert-butyl-cyclohexylcarbamoyl)-methoxy]-phenyl}-2-methoxy-propionic acid;
(2S)-Z-3-{4-[(4-tert-butyl-cyclohexylcarbamoyl)-methoxy]-phenyl}-2-methoxy-propionic acid;
(2S)-3-(4-cyclobutylcarbamoylmethoxy-phenyl)-2-methoxy-propionic acid;
(2S)-2-methoxy-3-{4-[(1-methyl-3-phenyl-propylcarbamoyl)-methoxy]-phenyl}-propionic acid;
(2S)-3-{4-[(5-tert-butyl-[1,3,4]thiadiazol-2-ylcarbamoyl)-methoxy]-phenyl}-2-methoxy-propionic acid;
(2S)-3-{4-[(5-tert-butyl-[1,3,4]thiadiazol-2-ylcarbamoyl)-methoxy]-phenyl}-2-methoxy-propionic acid;
(2S)-3-{4-[(4-tert-butyl-thiazol-2-ylcarbamoyl)-methoxy]-phenyl}-2-methoxy-propionic acid;
3-{4-[(5-cyclopropyl-[1,3,4]thiadiazol-2-ylcarbamoyl)-methoxy]-phenyl}-2-methoxy-propionic acid;
(2S)-2-methoxy-3-(4-{[2-(4-phenoxy-phenyl)-ethylcarbamoyl]-methoxy}-phenyl)-propionic acid;
(2S)-3-{4-[(1,3-dimethyl-butylcarbamoyl)-methoxy]-phenyl}-2-methoxy-propionic acid;
(2S)-2-methoxy-3-{4-[(1-methyl-hexylcarbamoyl)-methoxy]-phenyl}-propionic acid;
(2S)-2-methoxy-3-{4-[(1-methyl-butylcarbamoyl)-methoxy]-phenyl}-propionic acid;
(2S)-2-methoxy-3-{4-[(3-methyl-butylcarbamoyl)-methoxy]-phenyl}-propionic acid;
(2S)-3-{4-[(2,2,3,3,4,4,4-heptafluoro-butylcarbamoyl)-methoxy]-phenyl}-2-methoxy-propionic acid;
(2S)-3-(4-cyclopentylcarbamoylmethoxy-phenyl)-2-methoxy-propionic acid;
3-{3-[(4-cis-tert-butyl-cyclohexylcarbamoyl)-methoxy]-phenyl}-2-methoxy-propionic acid; and
pharmaceutically acceptable salts thereof;
Z) A compound

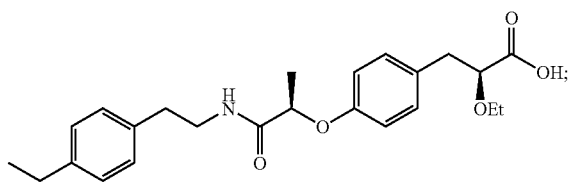

and pharmaceutically acceptable salts thereof;
AA) A compound that is the hemipiperazine salt;
BB) R5 is methyl and R6 is hydrogen;
CC) R1 is hydrogen;
DD) R2 is arylalkyl wherein arylalkyl is unsubstituted or substitued with from one to three substituents each independently selected from the group consisting of R2';
EE) R2 is arylalkyl;
FF) R2 is arylalkyl and the aryl group is phenyl;
GG) E is C(R3)(R4)A, and R3 is hydrogen and R4 is alkoxy;
HH) R4 is ethoxy;
II) A is COOH;
JJ) R4 is halo, $C_1$-$C_5$ alkyl, $C_1$-$C_5$ alkoxy, $C_3$-$C_6$ cycloalkyl, aryl $C_0$-$C_4$ alkyl, $C_{1-4}$alkoxyaryl, and phenyl, wherein said $C_1$-$C_5$ alkyl, $C_1$-$C_5$ alkoxy, $C_3$-$C_6$ cycloalkyl, aryl $C_0$-$C_4$ alkyl, $C_{1-4}$alkoxyaryl, and phenyl, are each unsubstituted or each independently substituted with from one to three groups each independently selected from R4'; or R3 and R4 are combined to form a $C_3$-$C_6$ cycloalkyl;
KK) R4 is selected from the group consisting of $C_1$-$C_5$ alkoxy, $C_3$-$C_6$ cycloalkyl, aryl $C_0$-$C_4$ alkyl, $C_{1-4}$alkoxyaryl, and phenyl, wherein said $C_1$-$C_5$ alkoxy, $C_3$-$C_6$ cycloalkyl, aryl $C_0$-$C_4$ alkyl, $C_{1-4}$alkoxyaryl, and phenyl are each unsubstituted or each independently substituted with from one to three groups each independently selected from R4'; or R3 and R4 are combined to form a $C_3$-$C_6$ cycloalkyl;
LL) R2 is arylC2alkyl;
MM) aryl is phenyl;
NN) A compound of this invention is formulated as a tablet or capsule;
OO) A compound of this invention is used to treat diabetes;
PP) A compound of this invention is used to treat Syndrome X;
QQ) A compound of this invention is used to treat elevated lipids;
RR) A compound of this invention is a pharmaceutically acceptable salt;
In one preferred class of compounds of the invention:
SS) R2 is substituted arylalkyl and R1 is hydrogen;
TT) R2 is aryalklyl, R1 is hydrogen, R5 is hydrogen, E is C(R3)(R4)A, and A is COOR14, said arylalkyl is unsubstituted or substituted with a from one to three substituents each independently selected from the group consisting of R2';
UU) R2 is arylaklyl, R1 is hydrogen, R5 is hydrogen, E is C(R3)(R4)A, R4 is C1-C3alkoxy, and A is COOR14, said arylalkyl is unsubstituted or substituted with a from one to three substituents each independently selected from the group consisting of R2'
VV) R2 is aryl$C_1$-$C_3$alkyl, R1 is hydrogen, R5 is hydrogen, E is C(R3)(R4)A, R4 is C1-C3alkoxy, and A is COOR14, said arylalkyl is unsubstituted or substituted with a from one to three substituents each independently selected from the group consisting of R2';
WW) R2 is substituted aryl$C_1$-$C_3$alkyl wherein the substitution is from 1-2 each independently selected from the group consisting of $C_1$-$C_3$ alkyl, halo, and $C_1$-$C_3$alkoxy, R1 is hydrogen, R5 is hydrogen, E is C(R3)(R4)A, R4 is $C_1$-$C_3$alkoxy, and A is COOR14;
XX) R2 is substituted aryl$C_1$-$C_3$alkyl wherein the substitution is from 1-2 each independently selected from the group consisting of $C_1$-$C_3$ alkyl and $C_1$-$C_3$alkoxy, R1 is hydrogen, R5 is hydrogen, E is C(R3)(R4)A, R4 is $C_1$-$C_3$alkoxy, and A is COOR14;
YY) R1 is selected from the group consisting of hydrogen, C1-C4 alkyl, and arylC0-C4alkyl, R2 is arylC0-C4alkyl, heteroarylC0-C4alkyl;
ZZ) R2 is arylC0-C4 alkyl, C1-C8 alkyl, heteroarylC0-C4alkyl, C3-C6cycloalkyl, C0-C4alkylC(O)heteroC1-C8alkyl, arylheteroC1-C8alkyl, wherein the arylC0-C4 alkyl, C1-C8 alkyl, heteroarylC0-C4alkyl, C3-C6cycloalkyl, C0-C4alkylC(O)heteroC1-C8alkyl, arylheteroC1-C8alkyl are each independently unsubstituted or each independently substituted with from one to three substituents each independently selected from the group consisting of phenyl, halophenyl, phenoxy, halo, haloC1-C4alkyl, C1-C4alkoxy, and C3-C6cyclalkyl;

AAA) R1 and R2 together form a piperidine, a piperazine or a dihydroisoquinoline group which piperidine, a piperazine or a dihydroisoquinoline are each independently unsubstituted or each independently subtituted with from one to three substituents selected from the group consisting of C1-C4 alkyl, phenyl, halophenyl, trifluormethylphenyl, methylphenyl, methoxyphenyl, acetylphenyl, benzyl, halobenzyl, benzoyl, halobenzoyl, trifluormethylbenzoyl, methylbenzoyl, methoxybenzoyl, acetyl benzoyl, biphenylmethylene, (pheny)(halophenyl)methylene, and bihalophenylmethylene.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:
1. A Compound of the structural formula I:
Formula I

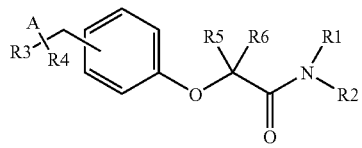

(a) R1 is hydrogen,
(b) R2' is selected from a group consisting of $C_1$-$C_5$ alkyl, $C_3$-$C_6$ cycloalkyl, $C_1$-$C_5$alkoxy, aryl$C_0$-$C_2$alkoxy, halo$C_1$-$C_3$alkyl, halo, aryl, —C(O)$C_1$-$C_5$alkyl, —C(O)-aryl, halo$C_1$-$C_5$alkyloxy, aryl$C_1$-$C_5$alkyl, and biaryl$C_1$-$C_5$alkyl; and which —C(O)-aryl is unsubstituted or substituted with from one to three substituents each independently selected from the group consisting of halo, $C_1$-$C_5$ alkyl, halo$C_1$-$C_5$ alkyl, $C_1$-$C_5$ alkoxy, and —C(O)$C_1$-$C_5$alkyl; and which $C_1$-$C_5$ alkyl, aryl$C_1$-$C_5$alkyl, biaryl$C_1$-$C_5$alkyl, and aryl are each independently unsubstituted or substituted with from one to three substituents each independently selected from the group consisting of halo, $C_1$-$C_5$alkyl, aryl, halo$C_1$-$C_5$ alkyl, trihalo$C_1$-$C_3$alkyl, $C_1$-$C_5$alkoxy, and aryl$C_1$-$C_5$alkyl; and which aryl is unsubstituted or substituted with from one to three substituents each independently selected from the group consisting of halo, $C_1$-$C_8$alkyl, aryl, halo$C_1$-$C_5$alkyl, trihalo$C_1$-$C_3$alkyl, $C_1$-$C_5$alkoxy, and aryl$C_1$-$C_5$alkyl;
(c) R2 is selected from the group consisting of $C_1$-$C_8$ alkyl, $C_3$-$C_6$ cycloalkyl, aryl-$C_{0-4}$-alkyl, amino$C_1$-$C_4$alkyl, $C_3$-$C_6$ cycloalkylaryl-$C_{0-2}$-alkyl, arylhetero$C_1$-$C_8$alkyl, $C_{0-4}$-alkyl-C(O)heteroC$_4$-C$_8$alkyl, —CH(C(O)OCH$_3$)benzyl, and —CH$_2$—C(O)—R15"-R16", and which $C_1$-$C_8$ alkyl, $C_3$-$C_6$ cycloalkyl, aryl-$C_{0-4}$-alkyl, amino$C_1$-$C_4$alkyl, $C_3$-$C_6$ cycloalkylaryl-$C_{0-2}$-alkyl, arylheteroC$_1$-C$_8$alkyl, $C_{0-4}$-alkyl-C(O)heteroC$_1$-C$_8$alkyl, and —CH$_2$—C(O)—R15"-R16" are each independently unsubstituted or substituted with from one to three substituents each independently selected from the group consisting of R2';
(d) R15" is O or NH;
(e) R16" is $C_1$-$C_2$ alkyl or benzyl which $C_1$-$C_2$ alkyl and benzyl are each unsubstituted or substituted with from one to three substituents each independently selected from the group consisting of R16';
(f) R7' and R7" are each independently selected from the group consisting of $C_1$-$C_4$alkyl and $C_1$-$C_4$ haloalkyl;
(g) n and m are each independently selected from the group consisting of 0, 1, 2 and 3;
(h) A is selected from the group consisting of $(CH_2)_m$COOR14, $C_1$-$C_3$alkylnitrile, carboxamide, sulfonamide, acylsulfonamide and tetrazole, and which sulfonamide, acylsulfonamide and tetrazole are each independently unsubstituted or substituted with from one to three substituents each independently selected from the group consisting of A';
(i) A' is a group consisting of $C_1$-$C_4$alkyl, $C_1$-$C_4$ haloalkyl, heteroaryl, and aryl, and wherein heteroaryl and aryl are each independently unsubstituted or substituted with from one to three substituents each independently selected from the group consisting of halo, $C_1$-$C_5$ alkyl, $C_1$-$C_5$ haloalkyl, $C_1$-$C_5$ alkoxy, and —C(O)$C_1$-$C_5$ alkyl;
(j) R3 is selected from the group consisting of H, $C_1$-$C_5$ alkyl, $C_1$-$C_5$ alkenyl, and $C_1$-$C_6$ alkoxy;
(k) R4 is selected from the group consisting of H, halo, $C_1$-$C_5$ alkyl, $C_1$-$C_6$ alkoxy, $C_3$-$C_6$ cycloalkyl, aryl $C_0$-$C_4$ alkyl, and $C_{0-4}$alkoxyaryl, and which $C_1$-$C_5$ alkyl, $C_1$-$C_5$ alkoxy, $C_3$-$C_6$ cycloalkyl, aryl $C_0$-$C_4$ alkyl, and $C_{0-4}$alkoxyaryl are each independently unsubstituted or each independently substituted with from one to four substituents each independently selected from R4'; or R3 and R4 are combined to form a $C_3$-$C_6$ cycloalkyl;
(l) R5 and R6 are each independently selected from the group consisting of hydrogen, $C_1$-$C_8$ alkyl, aryl-$C_{0-4}$-alkyl, heteroaryl-$C_{0-4}$-alkyl, $C_3$-$C_6$ cycloalkylaryl-$C_{0-2}$-alkyl, $C_3$-$C_6$ cycloalkyl-$C_{0-2}$-alkyl, and —CH$_2$—C(O)—R17-R18, and which $C_1$-$C_8$ alkyl, aryl-$C_{0-4}$-alkyl, heteroaryl-$C_{0-4}$-alkyl, $C_3$-$C_6$ cycloalkylaryl-$C_{0-2}$-alkyl, $C_3$-$C_6$ cycloalkyl-$C_{0-2}$-alkyl, and —CH$_2$—C(O)—R17-R18 are each independently unsubstituted or substituted with from one to four substituents each independently selected from the group consisting of R5';
(m) R4', R5', and R13" are each independently a group consisting of C1-C5 alkyl, C1-C5 alkoxy, C1-C5 haloalkyl, C1-C5 haloalkoxy, nitro, cyano, CHO, hydroxy, $C_1$-$C_4$ alkanoic acid, phenyl, aryloxy, SO$_2$R7', SR7", aryl$C_0$-$C_2$alkoxy, C1-C6alkylcarboxamido, and COOH;
(n) R16' is a group consisting of halo, $C_1$-$C_8$alkyl, aryl, haloalkyl, trihalo$C_1$-$C_3$alkyl, $C_1$-$C_5$alkoxy, and aryl$C_1$-$C_5$alkyl;
(o) R17 and R18 are each independently selected from $C_1$-$C_8$ alkyl, aryl-$C_{0-4}$-alkyl, heteroaryl-$C_{0-4}$-alkyl, $C_3$-$C_6$ cycloalkylaryl-$C_{0-2}$-alkyl, and $C_3$-$C_6$ cycloalkyl-$C_{0-2}$-alkyl;
(p) R14 is selected from the group consisting of hydrogen, C1-C4alkyl, aryl, and arylmethyl, and which C1-C4alkyl are each independently unsubstituted or independently substituted with from one to three substituents each independently selected from the group consisting of R13' and which arylmethyl and aryl are each independently unsubstituted or independently substituted with from one to three substituents each independently selected from the group consisting of R14';

(q) R13' is a group consisting of $C_1$-$C_5$ alkyl, $C_3$-$C_6$ cycloalkyl, $C_1$-$C_5$ haloalkyl, $C_1$-$C_5$ alkoxy, aryloxy, halo, aryl, —C(O)$C_1$-$C_5$alkyl, —C(O)-aryl, halo$C_1$-$C_5$alkyloxy, aryl$C_1$-$C_5$ alkyl, and $C_1$-$C_5$ alkylbiaryl, and which —C(O)aryl, aryl, aryl$C_1$-$C_5$ alkyl, and $C_1$-$C_5$ alkylbiaryl are each independently unsubstituted or substutited with from one to three substituents each independently selected from the group consisting of R13"; and (r) R14' is a group consisting of halo, C1-C8alkyl, $C_1$-$C_5$ haloalkyl, $C_1$-$C_5$ alkoxy, and aryl$C_0$-$C_4$alkyl; or (s) a pharmaceutically acceptable salt thereof.

2. A compound as claimed by claim 1 of the structural Formula II:

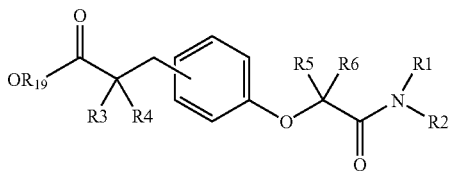

wherein R19 is selected from the group consisting of hydrogen, C1-C4alkyl, aryl, and arylmethyl, wherein the alkyl, aryl and arylmethyl are each unsubstituted or substituted with from one to three substituents each independently selected from R14'.

3. A compound as claimed by claim 2 that is of the following structural formula III:

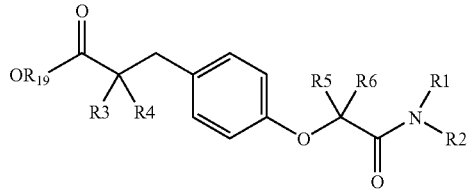

wherein R19 is selected from the group consisting of hydrogen, C1-C4alkyl, aryl, and arylmethyl, wherein the alkyl, aryl and arylmethyl are each unsubstituted or substituted with from one to three substituents each independently selected from R14'.

4. A compound as claimed by claim 1 wherein R1 is hydrogen.

5. A compound as claimed by of claim 4 wherein R2 is selected from the group consisting of aryl$C_0$-$C_4$alkyl, $C_1$-$C_8$ alkyl, heteroaryl$C_0$-$C_4$alkyl, $C_3$-$C_6$ cycloalkyl, $C_0$-$C_4$alkyl-C(O)-hetero$C_1$-$C_8$ alkyl, arylhetero$C_1$-$C_8$alkyl, wherein each of said R2 is unsubstituted or substituted by one or two substituents each independently selected from the group consisting of phenyl, halophenyl, phenoxy, halo, halo$C_1$-$C_4$ alkyl, $C_1$-$C_4$alkoxy, and $C_3$-$C_6$ cycloalkyl.

6. A compound as claimed by claim 5 wherein R2 is aryl$C_0$-$C_4$alkyl wherein the aryl is phenyl or napthyl, and the $C_0$-$C_4$alkyl is selected from the group consisting of methyl, ethyl and not present, that is $C_0$ alkyl.

7. A compound as claimed by of claim 5 wherein the R2 group is substituted with one or two substituents each independently selected from the group consisting of methyl, ethyl, t-butyl, fluorine, chlorine, bromine, trifluoromethyl, methoxyl, ethoxyl, phenyl, and phenoxyl.

8. A compound as claimed by claim 1 wherein R2 is —CH(C(O)OCH$_3$)benzyl.

9. A compound as claimed by claim 1 or claim 4 wherein R6 is selected from the group consisting of hydrogen, $C_1$-$C_4$ alkyl, and aryl-$C_{0-4}$-alkyl, wherein the alkyl and arylalkyl are each independently substituted with from one to three substituents each independently selected from the group consisting of R5'.

10. A compound as claimed by claim 9 wherein R5 is H or methyl.

11. A compound as claimed by any one of claims 1 or claim 10 wherein R6 is $C_1$-$C_3$ alkyl.

12. A compound as claimed by claim 11, wherein R6 is methyl.

13. A compound as claimed by claim 1 wherein R5 is hydrogen or methyl, R6 is $C_1$-$C_3$ alkyl, and R3 is $C_1$-$C_3$alkoxy.

14. A compound as claimed by claim 1 wherein A is C(O)OR26; R26 is H or $C_1$-$C_3$alkyl.

15. A compound as claimed by claim 1 which is selected from the group consisting of:

(2S,1'R)-2-Ethoxy-3-(4-{1'-[2-(4-phenoxy-phenyl)-ethylcarbamoyl]-ethoxy}-phenyl)-propionic acid; (2S,1'R)-2-Ethoxy-3-(4-{1'-[2-(4-ethyl-phenyl)-ethylcarbamoyl]-ethoxy}-phenyl)-propionic acid; (2S,1'R)-2-ethoxy-3-(4-{1'-[2-(4-trifluoromethyl-phenyl-ethylcarbamoyl]-ethoxy}-phenyl)-propionic acid;

(2S,1'R)-2-ethoxy-3-(4-{1'-[2-(2-ethoxy-phenyl)-ethylcarbamoyl]-ethoxy}-phenyl)-propionic acid;

(2S,1'R)-2-ethoxy-3-{4-[1'-(3-trifluoromethyl-benzylcarbamoyl)-ethoxy]-phenyl}-propionic acid;

(2S,1'R)-2-ethoxy-3-{4-[1'-(3-fluoro-5-trifluoromethyl-benzylcarbamoyl)-ethoxy]-phenyl}-propionic acid;

(2S,1'R)-3-(4-{1'-[(biphenyl-3-ylmethyl)-carbamoyl]-ethoxy}-phenyl)-2-ethoxy-propionic acid;

(2S,1'R)-3-(4-{1'-[2-(3-chloro-phenyl)-ethylcarbamoyl]-ethoxy}-phenyl)-2-ethoxy-propionic acid;

(2S,1'R)-2-ethoxy-3-(4-{1'-[2-(3-fluoro-phenyl)-ethylcarbamoyl]-ethoxy}-phenyl)-propionic acid;

(2S,1'R)-2-ethoxy-3-(4-{1'-[2-(2-fluoro-phenyl)-ethylcarbamoyl]-ethoxy}-phenyl)-propionic acid;

(2S,1'R)-3-(4-{1'-[2-(2,4-dichloro-phenyl)-ethylcarbamoyl]-ethoxy}-phenyl)-2-ethoxy-propionic acid;

(2S,1'R)-3-(4-{1'-[2-(2,6-dichloro-phenyl)-ethylcarbamoyl]-ethoxy}-phenyl)-2-ethoxy-propionic acid;

(2S,1'R)-3-(4-{1'-[2-(2-chloro-phenyl)-ethylcarbamoyl]-ethoxy}-phenyl)-2-ethoxy-propionic acid; (2S,1'R)-3-(4-{1'-[2-(4-tert-butyl-phenyl)-ethylcarbamoyl]-ethoxy}-phenyl)-2-ethoxy-propionic acid;

(2S,1'R)-2-ethoxy-3-{4-[1'-(4-fluoro-benzylcarbamoyl)-ethoxy]-phenyl}-propionic acid; (2S,1'R)-2-ethoxy-3-{4-[1'-(4-trifluoromethyl-benzylcarbamoyl)-ethoxy]-phenyl}-propionic acid;

(2S,1'R)-3-{4-[1'-(4-tert-butyl-benzylcarbamoyl)-ethoxy]-phenyl}-2-ethoxy-propionic acid; (2S,1'R)-3-{4-[1'-(4-tert-butyl-phenylcarbamoyl)-ethoxy]-phenyl}-2-ethoxy-propionic acid; (2S,1'R)-3-{4-[1'-(4-trans-tert-butyl-cyclohexylcarbamoyl)-ethoxy]-phenyl}-2-ethoxy-propionic acid;

(2S)-3-{4-[1-(4-tert-butyl-cyclohexylcarbamoyl)-1-methyl-ethoxy]-phenyl}-2-methoxy-propionic acid;

(2S)-2-methoxy-3-(4-{1-methyl-1-[2-(4-phenoxy-phenyl)-ethylcarbamoyl]-ethoxy}-phenyl)-propionic acid;
(2S)-3-(4-{1-[2-(2-ethoxy-phenyl)-ethylcarbamoyl]-1-methyl-ethoxy}-phenyl)-2-methoxy-propionic acid;
2-methoxy-3-(4-{1-methyl-1-[2-(3-trifluoromethyl-phenyl)-ethylcarbamoyl]-ethoxy}-phenyl)-propionic acid;
(2S)-2-methoxy-3-{4-[1-methyl-1-(3-trifluoromethyl-benzylcarbamoyl)-ethoxy]-phenyl}-propionic acid;
(2S)-3-(4-{1-[2-(2-chloro-phenyl)-ethylcarbamoyl]-1-methyl-ethoxy}-phenyl)-2-methoxy-propionic acid;
(2S)-3-(4-{1-[(biphenyl-3-ylmethyl)-carbamoyl]-1-methyl-ethoxy}-phenyl)-2-methoxy-propionic acid;
(2S)-3-(4-{1-[2-(2,5-dimethoxy-phenyl)-ethylcarbamoyl]-1-methyl-ethoxy}-phenyl)-2-methoxy-propionic acid;
(2S)-3-(4-{1-[2-(2-fluoro-phenyl)-ethylcarbamoyl]-1-methyl-ethoxy}-phenyl)-2-methoxy-propionic acid;
(2S)-2-ethoxy-3-(4-{1-methyl-1-[2-(3-trifluoromethyl-phenyl)-ethylcarbamoyl]-ethoxy}-phenyl)-propionic acid;
(2S)-2-ethoxy-3-{4-[1-(3-fluoro-5-trifluoromethyl-benzylcarbamoyl)-1-methyl-ethoxy]-phenyl}-propionic acid;
(2S)-3-(4-{1-[2-(2-chloro-phenyl)-ethylcarbamoyl]-1-methyl-ethoxy}-phenyl)-2-ethoxy-propionic acid;
(2S)-3-(4-{1-[(biphenyl-3-ylmethyl)-carbamoyl]-1-methyl-ethoxy}-phenyl)-2-ethoxy-propionic acid;
(2S)-3-(4-{1-[2-(3-chloro-phenyl)-ethylcarbamoyl]-1-methyl-ethoxy}-phenyl)-2-ethoxy-propionic acid;
(2S)-3-(4-{1-[2-(2,5-dimethoxy-phenyl)-ethylcarbamoyl]-1-methyl-ethoxy}-phenyl)-2-ethoxy-propionic acid;
(2S)-2-ethoxy-3-(4-{1-[2-(2-fluoro-phenyl)-ethylcarbamoyl]-1-methyl-ethoxy}-phenyl)-propionic acid;
(2S)-3-{3-[1-(4-tert-butyl-cyclohexylcarbamoyl)-1-methyl-ethoxy]-phenyl}-2-methoxy-propionic acid;
(2S)-3-{3-[1-(3-fluoro-5-trifluoromethyl-benzylcarbamoyl)-1-methyl-ethoxy]-phenyl}-2-methoxy-propionic acid;
(2S)-3-(3-{1-[(biphenyl-3-ylmethyl)-carbamoyl]-1-methyl-ethoxy}-phenyl)-2-methoxy-propionic acid;
(2S)-3-(3-{1-[2-(3-chloro-phenyl)-ethylcarbamoyl]-1-methyl-ethoxy}-phenyl)-2-methoxy-propionic acid;
(2S)-2-methoxy-3-{4-[(1-phenyl-ethylcarbamoyl)-methoxy]-phenyl}-propionic acid;
(2S)-3-(3-{1-[2-(2,4-dichloro-phenyl)-ethylcarbamoyl]-1-methyl-ethoxy}-phenyl)-2-methoxy-propionic acid;
(2S)-3-(3-{1-[2-(2,6-dichloro-phenyl)-ethylcarbamoyl]-1-methyl-ethoxy}-phenyl)-2-methoxy-propionic acid;
(2S)-3-(4-{1-[2-(2,4-dichloro-phenyl)-ethylcarbamoyl]-1-methyl-ethoxy}-phenyl)-2-methoxy-propionic acid;
(2S)-3-(4-{1-[2-(2,4-dichloro-phenyl)-ethylcarbamoyl]-1-methyl-ethoxy}-phenyl)-2-ethoxy-propionic acid;
(2S)-3-(4-{1-[2-(2,6-dichloro-phenyl)-ethylcarbamoyl]-1-methyl-ethoxy}-phenyl)-2-ethoxy-propionic acid;
(2S)-2-ethoxy-3-(4-{1-[2-(4-ethyl-phenyl)-ethylcarbamoyl]-1-methyl-ethoxy}-phenyl)-propionic acid;
(2S)-2-ethoxy-3-(4-{1-[2-(2-ethoxy-phenyl)-ethylcarbamoyl]-1-methyl-ethoxy}-phenyl)-propionic acid;
2-Ethoxy-3-{4-[1-(3-trifluoromethyl-benzylcarbamoyl)-ethoxy]-phenyl}-propionic acid;
2-Ethoxy-3-{4-[1-(5-fluoro-3-trifluoromethyl-benzylcarbamoyl)-ethoxy]-phenyl}-propionic acid;
2-Ethoxy-3-{4-[1-(3-phenyl-benzylcarbamoyl)-ethoxy]-phenyl}-propionic acid;
2-Ethoxy-3-{4-[1-(4-phenoxy-phenylethylcarbamoyl)-ethoxy]-phenyl}-propionic acid;
2-Ethoxy-3-{4-[1-(3-trifluoromethyl-phenylethylcarbamoyl)-ethoxy]-phenyl}-propionic acid;
3-(4-{1-[2-(2,6-Dichloro-phenyl)-ethylcarbamoyl]-ethoxy}-phenyl)-2-ethoxy-propionic acid;
2-Ethoxy-3-(4-{1-[2-(4-ethyl-phenyl)-ethylcarbamoyl]-ethoxy}-phenyl)-propionic acid;
2-Ethoxy-3-(4-{1-[2-(4-ethyl-phenyl)-ethylcarbamoyl]-ethoxy}-phenyl)-propionic acid;
3-(4-{Cyclohexyl-[2-(4-ethyl-phenyl)-ethylcarbamoyl]-methoxy}-phenyl)-2-ethoxy-propionic acid; and
2-Ethoxy-3-(4-{1-[2-(4-ethyl-phenyl)-ethylcarbamoyl]-2-phenyl-ethoxy}-phenyl)-propionic acid;

or pharmaceutically acceptable salts thereof.

16. A compound as claimed by claim 1 wherein the compound is selected from the group consisting of (2S,1'R)-3-{4-[1'-(4-tert-butyl-cyclohexylcarbamoyl)-ethoxy]-phenyl}-2-ethoxy-propionic acid; or pharmaceutically acceptable salts thereof.

17. A compound as claimed by claim 1 wherein the compound is

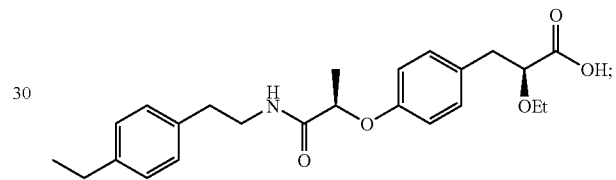

or a pharmaceutically acceptable salt thereof.

18. A pharmaceutical composition, comprising a pharmaceutically acceptable carrier and at least one compound as claimed by claim 1 or a pharmaceutically acceptable salt thereof.

19. A method of treating diabetes mellitus in a mammal, comprising the step of administering to the mammal a therapeutically effective amount of at least one compound of claim 1 or a pharmaceutically acceptable salt thereof.

20. A method of treating Syndrome X in a mammal, comprising the step of administering to the mammal a therapeutically effective amount of at least one compound of claim 1 or a pharmaceutically acceptable salt thereof.

21. A compound or pharmaceutically acceptable salt thereof according to claim 1 for use as a medicine.

22. A compound of the formula

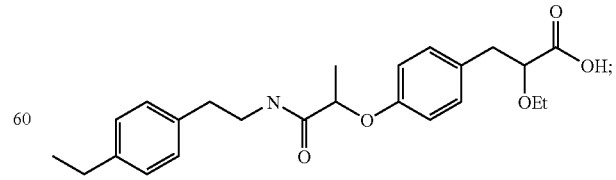

or a pharmaceutically acceptably salt thereof.

23. A compound as claimed by claim 1 that is of the formula:

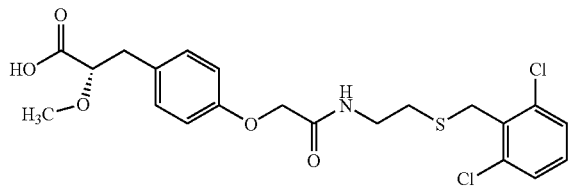

or a pharmaceutically acceptable salt thereof.

24. A compound as claimed by any one of claims 1, or 23 wherein the compound is a pharmaceutically acceptable salt.

25. A compound of claim 1 that is (2S)-3-(4-{[2-(2,6-dichloro-benzylsulfanyl)-ethylcarbamoyl]-methoxy}-phenyl)-2-methoxy-propionic acid.

26. A pharmaceutical composition comprising a pharmaceutically acceptable carrier and at least one compound as claimed by claim 23 or 24.

* * * * *

UNITED STATES PATENT AND TRADEMARK OFFICE
CERTIFICATE OF CORRECTION

PATENT NO.         : 7,220,880 B2
APPLICATION NO.    : 10/517581
DATED              : May 22, 2007
INVENTOR(S)        : Ferritto Crespo Rafael It is certified that error appears in the above-identified patent and that said Letters Patent is hereby corrected as shown below:

1. Column 109 line 51 claim 1 (b)
    Delete: group consisting of halo, $C_1$-$C_5$alkyl, aryl, halo $C_1$-$C_5$
    Insert: group consisting of halo, $C_1$-$C_8$alkyl, aryl, halo$C_1$-$C_5$ 2. Column 109 line 61 claim 1 (c)
    Delete: ero$C_1$-$C_8$alkyl, $C_{0-4}$-alkyl-C(O)hetero$C_4$-$C_8$alkyl,
    Insert: ero$C_1$-$C_8$alkyl, $C_{0-4}$-alkyl-C(O)hetero$C_1$-$C_8$alkyl, 3. Column 111 line 10 claim 1 (q)
    Delete: substutited with from one to three substituents each
    Insert: substituted with from one to three substituents each 4. Column 111 line 56 claim 5
    Delete: 5. A compound as claimed by of claim 4 wherein R2 is
    Insert: 5. A compound as claimed by claim 4 wherein R2 is 5. Column 112 line 1 claim 7
    Delete: 7. A compound as claimed by of claim 5 wherein the R2
    Insert: 7. A compound as claimed by claim 5 wherein the R2

6. Column 112 line 31 claim 15
    Delete: ethoxy-3-(4-{1'-[2-(4-trifluoromethyl-phenyl-
    Insert: ethoxy-3-(4-{1'-[2-(4-trifluoromethyl-phenyl)-

UNITED STATES PATENT AND TRADEMARK OFFICE
CERTIFICATE OF CORRECTION

PATENT NO. : 7,220,880 B2
APPLICATION NO. : 10/517581
DATED : May 22, 2007
INVENTOR(S) : Ferritto Crespo Rafael It is certified that error appears in the above-identified patent and that said Letters Patent is hereby corrected as shown below:

7. Column 116 line 8 claim 26
　　Delete: claimed by claim 23 or 24.
　　Insert: claimed by claim 23 or 25.

Signed and Sealed this

Thirtieth Day of October, 2007

JON W. DUDAS
*Director of the United States Patent and Trademark Office*